(12) United States Patent
Gelfand et al.

(10) Patent No.: US 7,745,125 B2
(45) Date of Patent: Jun. 29, 2010

(54) 2'-TERMINATOR RELATED PYROPHOSPHOROLYSIS ACTIVATED POLYMERIZATION

(75) Inventors: David H. Gelfand, Oakland, CA (US); Keith A. Bauer, San Rafael, CA (US); Amar P. Gupta, Danville, CA (US); Veeraiah Bodepudi, San Ramon, CA (US); John Niemiec, San Leandro, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 469 days.

(21) Appl. No.: 11/583,606

(22) Filed: Oct. 18, 2006

(65) Prior Publication Data

US 2007/0154914 A1 Jul. 5, 2007

Related U.S. Application Data

(63) Continuation-in-part of application No. 10/879,494, filed on Jun. 28, 2004, and a continuation-in-part of application No. 10/879,493, filed on Jun. 28, 2004.

(51) Int. Cl.
 *C12Q 1/68* (2006.01)
(52) U.S. Cl. ......................................................... 435/6
(58) Field of Classification Search ........................ None
 See application file for complete search history.

(56) References Cited

U.S. PATENT DOCUMENTS

| | | | |
|---|---|---|---|
| 3,338,882 | A | 8/1967 | Wechter |
| 4,458,066 | A | 7/1984 | Caruthers et al. |
| 4,469,863 | A | 9/1984 | Ts'o et al. |
| 4,594,320 | A | 6/1986 | Fujishima |
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,466,786 | A | 11/1995 | Buhr et al. |
| 5,532,130 | A | 7/1996 | Alul |
| 5,547,835 | A | 8/1996 | Köster |
| 5,602,240 | A | 2/1997 | De Mesmaeker et al. |
| 5,637,684 | A | 6/1997 | Cook et al. |
| 5,644,048 | A | 7/1997 | Yau |
| 5,750,673 | A | 5/1998 | Martin |
| 5,914,396 | A | 6/1999 | Cook et al. |
| 5,939,292 | A | 8/1999 | Gelfand et al. |
| 5,990,303 | A | 11/1999 | Seela |
| 6,147,200 | A | 11/2000 | Manoharan et al. |
| 6,184,364 | B1 | 2/2001 | Pieken et al. |
| 6,495,671 | B1 | 12/2002 | Manoharan et al. |
| 6,531,584 | B1 | 3/2003 | Cook et al. |
| 6,699,668 | B1 | 3/2004 | Schmidt et al. |
| 6,921,812 | B1 | 7/2005 | Prakash et al. |
| 2001/0041794 | A1 | 11/2001 | Bischofberger et al. |
| 2004/0023240 | A1 | 2/2004 | Marliere et al. |
| 2007/0154914 | A1 | 7/2007 | Gelfand et al. |

FOREIGN PATENT DOCUMENTS

| | | |
|---|---|---|
| CH | 518950 | 2/1972 |
| DE | 3803021 A1 | 8/1989 |
| EP | 0063879 A2 | 4/1982 |
| EP | 2007008997 | 10/2007 |
| JP | 52090693 | 2/1977 |
| JP | 03178985 | 8/1991 |
| JP | 09316093 | 12/1997 |
| WO | WO 99/13103 A1 | 3/1999 |
| WO | WO 00/63366 A2 | 10/2000 |
| WO | WO 01/62975 A2 * | 8/2001 |
| WO | WO 01/90121 A2 | 11/2001 |
| WO | WO 01/96354 A1 | 12/2001 |
| WO | WO 02/057425 A2 | 7/2002 |
| WO | WO 03/004603 A2 | 1/2003 |
| WO | 2005005667 A2 | 1/2005 |
| WO | 2005005667 A3 | 1/2005 |
| WO | WO 2005/005667 A2 | 1/2005 |
| WO | 2005118608 A2 | 12/2005 |
| WO | 2005118608 A3 | 12/2005 |
| WO | 2007075967 A2 | 7/2007 |
| WO | 2007075967 A3 | 7/2007 |
| WO | WO 2004/021075 | 7/2007 |

OTHER PUBLICATIONS

Carroll et al. ("Inhibition of hepatitis C virus RNA replication by 2'-modified nucleoside analogs" J Biol Chem. Apr. 4, 2003;278(14):11979-84. Epub Jan 27, 2003).*
Arion et al. (Biochemistry. Nov. 10, 1998;37(45):15908-17).*
D'Abramo et al. (J Mol Biol. Mar. 12, 2004;337(1):1-14).*
Deval et al. (Antimicrob Agents Chemother. Aug. 2007;51(8):2920-8).*

(Continued)

*Primary Examiner*—Christopher M. Babic
(74) *Attorney, Agent, or Firm*—Townsend and Townsend and Crew LLP

(57) ABSTRACT

The present invention provides reaction mixtures that include blocked oligonucleotides comprising 2'-terminator nucleotides. The blocked oligonucleotides are rendered extendible when the 2'-terminator nucleotides are removed from the oligonucleotides, e.g., via pyrophosphorolysis. The reaction mixtures can be used in various nucleic acid polymerization and/or amplification assays, among many other applications. In addition to reaction mixtures, the invention also provides related methods and reaction mixtures.

32 Claims, 14 Drawing Sheets

OTHER PUBLICATIONS

Messens, E., et al. (1968) "The Synthesis of Nucleoside 2' (3')—Phosphate 5'—Triphosphates," *FEBS Letters*, vol. 1, No. 5: 326-328.

Zhang, Jia, et al., 2005 "Proofreading genotyping assays mediated by high fidelity exo + DNA polymerases", Trends in Biotechnology, 23(2):92-96.

Adams et al.; "Nucleotide sequence from the coat protein cistron of R17 bacteriophage RNA"; 1969, *Nature*, vol. 223, No. 10, pp. 1009-1014.

Beaucage et al.; "The Functionalization of Oligonucleotides via Phosphoramidite Derivative"; 1993, *Tetrahedron*, vol. 49, No. 10, pp. 1925-1963.

Beaucage et al.; "Deoxynucleoside Phosphoramidites—A New Class of Key Intermediates for Deoxypolynucleotide Synthesis"; 1981, *Tetrahedron Letters*, vol. 22, pp. 1859-1862.

Benett, G. et al.; "Guanosine Tetraphosphate and Its Analogs. Chemical Synthesis of Guanonie 3'5'-Dipyrophosphate, Deoxyguanosine 3', 5' -Dipyrophosphate, Guanosine 2', 5'—Bis (methylenediphosphonate), and Guanosine 3', 5'-Bis(methylenediphosphonate)"; 1976, *Biochemistry*, vol. 15, No. 21, pp. 4623-4628

Brill et al.; "Synthesis of Oligodeoxynucleoside Phosphorodithioates via Thiomid"; 1989, *Journal of American Chemistry Society*, vol. 111, pp. 2321-2323.

Brown et al.; "Chemical synthesis and Cloning of a Tyrosine tRNA Gene"; 1979, *Methods in Enzmology*, vol. 68, pp. 109-151.

Brownlee et al.; "Molecular Structure: Nucelotide Sequence of 5S-ribosomal RNA from *Escherichia coli*"; 1967, *Nature*, vol. 215, Vol. 102, pp. 735-736.

Burgess, K. et al.; "Synthesis of Nucleoside Triphosphates"; 2000, Chem. Rev., vol. 100, pp. 2047-2059.

Carlsson et al.; "Screening for Genetic Mutations", 1996, *Nature*, vol. 380, p. 207.

Carroll, S. et al.; "Only a Small Fraction of Purified of Purified Hepatitus C RNA-Dependent RNA Polymerase is Catalytically Competent: Implications for Viral Replication and in Vitro Assays"; 2000, *Biochemistry*, vol. 39, pp. 8243-8249.

Carroll et al.; "Inhibition of Hepatitis C Virus RNA Replication by 2'-Modified Nucleoside Analogs"; 2003, *The Journal of Biological Chemistry*, vol. 278, No. 14, pp. 11979-11984.

Cheng, C. et al.; "Phosphorylation of Adenosine with Trimetaphosphate Under Simulated Prebiotic Conditions"; 2001, *Origins of Life and Evolution of the Biosphire*, vol. 32, pp. 219-224.

Crimmins, M. et al.; "Solid-Phase Synthesis of Carbocyclic Nucleosides"; 2000, *American Chemical Society*, vol. 2, No. 8, pp. 1065-1067.

Daluge, S. et al.; "1592U89, a Novel Carbocyclic Nucleoside Analog with Potent, Selective Anti-Human Immunodeficiency Virus Activity"; 1997, *Antimicrobial Agents and Chemotherapy*, vol. 41, No. 5, pp. 1082-1093.

Denpcy, et al.; "Synthesis of a Thymidyl Pentamer of Deoxyribonucleic Guanidine and Binding Studies with DNA Homopolynucleotides"; 1995, *Proceedings of the National Academy of Sciences*, vol. 92, pp. 6097-6101.

Egholm et al.; "Peptide nucleic acids (PNA). Oligonucleotide analogs with an achiral peptide backbone"; 1992, *Journal of American Chemistry Society*, vol. 114, pp. 1895-1897.

Egholm et al.; "PNA hybridizes to complementary oligonucleotides obeying the Watson-Crick hydrogen-bonding rules"; 1993, *Nature*, vol. 365, pp. 566-568.

Etaix, E. et al.; "phosphorylation of Nucleosides in Aqueous Solution Using Trimetaphosphate: Formation of Nucleoside Triphosphates"; 1978, *Journal of Carbohydrates, Nucleosides, and Nucleotides*, vol. 5, No. 2, pp. 91-110.

Franchetti, P. et al.; "2'-C-Methyl Analogues of Selective Adenosine Receptor Agonists: Synthesis and Binding Studies"; 1998, *J. Med. Chem.*, vol. 41, pp. 1708-1715.

Gao et al.; 1994, Unusal conformation of a 3'-thioformacetal linkage in DNA duplex; 1994, *Journal of Biomolecular NMR*, vol. 4, pp. 17-34.

Gilbert et al.; "The nucleotide sequence of the lac operator"; 1973, *Proceedings of the National Academy of Sciences*, vol. 70, No. 12, pp. 3581-3584.

Grein et al.; "3-Deaza-and-7-Deazapurines: Duplex Stability of Oligonucleotides Containing Modified Adenine or Guanine Bases"; 1994, *Bioorganic Medicinal Chemistry Letters*, vol. 4, No. 8, pp. 971-976.

Hamel; "Derivatives of guanosine triphosphate with ribose 2'-hydroxyl substituents. Interactions with the protein synthetic enzymes of *Escherichia coli*"; 1976, *European Journal of Biochemistry*, vol. 70, No. 2, pp. 339-347.

Hamel; "Interactions of guanosine triphosphate analogues with elongation factor G of *Escherichia coli*"; 1976, *European Journal of Biochemistry*, vol. 63, No. 2, pp. 431-440.

Horn et al.; "Oligonucleotides with alternating anionic and cationic phosphoramidate linkages: Synthesis and hybridization of stereouniform isomers"; 1996, *Tetrahedron Letters*, vol. vol. 37, pp. 743-764.

Jenkins et al.; "The Biosynthesis of Carbocyclic"; 1995, *Chemical Society Review*, pp. 169-176.

Jung et al.; "Hybridization of Alternating Cationic Anionic Oligonucleotieds to RNA Segments"; 1994, *Nucleoside & Nucleotide*, vol. 13, No. 6-7, pp. 1597-1605.

Kiedrowski et al.; "Parabolic Growth of a Self-Replicating Hexadeoxynucleotide Bearing a 3'-5'-Phosphamidate Linkage"; 1991, *Angew. Chem. Int. Ed.*, vol. 30, pp. 423-426.

Kleiber, J. et al.; "Performance Characteristics of a Quantitative, Homogeneous TaqMan RT-PCR Test for HCV RNA"; 2000, *Journal of Molecular Diagnostics*, vol. 2, No. 3, pp. 158-166.

Lee et al.; "DNA sequencing with dye-labeled terminators and T& DNA polymerase: effect of dyes and dNTPs on incorporation of dye-terminators and probility analysis of termination fragments"; 1992, *Nucleic Acid Res.*, vol. 20, pp. 2471-2483.

Letsinger; "Phosphoramidate Analogs of Oligonucleotides"; 1970, *Journal of Organic Chemistry*, vol. 35, No. 11, pp. 3800-3803.

Letsinger; "Effects of pendant groups at phosphorus on binding properties of d-ApA analogues"; 1986, *Nucleic Acids Research*, vol. 14, pp. 3487-3499.

Letsinger; "Cationic oligonucleotides"; 1988, *Journal of American Chemistry Society*, vol. 10, pp. 4470-4471.

Mag et al.; "Synthesis and selective cleavage of an oligodeoxynucleotide containing a bridged internucleotide 5'-phosphorothioate linkage"; 1991, *Nucleic Acids Research*, vol. 19, No. 7, pp. 1437-1441.

Matteucci et al.; "Total solid-phase synthesis of porcine gut gastrin releasing peptide (GRP), a mammalian bombesin"; 1991, *Journal of American Chemistry Society*, vol. 103, pp. 3185-3191.

Maxam et al.; "A new method for sequencing DNA"; 1977, *Proceedings of the National Academy of Sciences*, vol. 74, pp. 560-564.

Meier et al.; "Peptide Nuclein Acids (PNAs)—Unusal Properties of Nonionic Oligonucleotide Analogs"; 1992, *Angew. Chem. Int. Ed.*, vol. 31, No. 8, pp. 1008-1010.

Meng, Q. et al.; "Automated Multiplex Assay System for Simultaneous Detection of Hepatitis B Virus DNA, Hepatitis C Virus DNA, and Human Immunodeficiency Virus Type 1 RNA"; 2001, *Journal of Clinical Microbiology*, vol. 39, No. 8, pp. 2937-2945.

Mesmaeker et al.; "Comparison of Rigid and Flexible Backbones in Antosense Oligonucleotides"; 1994, *Bioorganic & Medicinal Chemistry Letters*, vol. 4, No. 3, pp. 395-398.

Mohanty, B. et al.; "Polynucleotide phosphorylase functions both as a 3'—5" exonuclease and a poly (A) polymerase in *Escherichia coli*"; 2000, *Proceedings of the National Academy of Sciences*, vol. 97, No. 22, 11966-11971.

Moore et al.; "Synthesis of Nucleotide Analogues That Potently and Selectively Inhibit Humna DNA Primase"; 2002, *Biochemistry*, vol. 41, pp. 14066-14075.

Narang et al.; "Improved Phosphotriester Method for the Synthesis of Gene Fragments"; 1979, *Methods in Enzymology*, vol. 68, pp. 90-99.

Pauwels et al.; "Biological Activity of New 2-5A Analogs"; 1986, *Chemica Scripta*, vol. 26, pp. 141-145.

Saffhill, R. et al.; "Selective Phosphorylation of the cis-2', 3'—Diol of Unprotected Ribonucleosides with Trimetaphosphate in Aqueous Solution"; 1967, *J. Org. Chem.*, vol. 35, No. 9, pp. 2881-2883.

Sanger et al.; "Use of DNA polymerase I primed by a synthetic oligonucleotide to determine a nucleotide sequence in phage fl DNA"; *Proceedings of the National Academy of Sciences*, vol. 70, No. 4, pp. 1209-1213.

Sanger et al.; "DNA sequencing with chain-terminating inhibitors"; 1977, *Proceedings of the National Academy of Sciences*, vol. 74, No. 12, pp. 5463-5467.

Sanger et al.; "DNA sequencing with chain-terminating inhibitors"; 1992, *Milestones in Biotechnology*, pp. 104-108.

Sanghvi et al.; "Carbohydrate Modifications in Antisense Research"; 1994, *ASC Symposium Series 580*, Chapters 2 and 3.

Sauer et al.; "Facile method for automated genotyping of single nucleotide polymorphisms by mass spectrometry"; 2002, *Nucleic Acids Research*, vol. 30, No. 5, pp. e22.

Sawai; "Synthesis and Propties of Oligoadenylic Acids Containing 2'-5' Phosphoramide Linkage"; 1984, *Chemistry Letters*, pp. 805-808.

Seela et al.; "Oligonucleotides Containing Pyrazolo[3,4 d] pyrimidines: The influence of 7-Substituted 8-Aza-7-deaza-2'-deoxyguanosines on the Duplex Structure and Stability"; 1999, *Helvetica Chimic Acta*, vol. 82, pp. 1640-1655.

Seela et al.; "3-Deazaguanine $N^7$—and $N^9$ -(2' Deoxy—β—D-ribofuranosides): Building Blocks for Solid-Phase Synthesis and Oncorporation into Oligodeoxyribonucleotides"; 1991, *Helvetica Chimic Acta*, vol. 74, pp. 1790-1800.

Smith et al.; "Fluorescence detection in automated DNA sequence analysis"; 1986, *Nature*, vol. 321, pp. 674-679.

Sprinzl et al.; "Enzymatic Incorporation of ATP and CTP Analogues into the 3' End of tRNA"; 1977, *European Journal of Biochemistry*, vol. 81, pp. 579-589.

Von Kiedrowski, G. et al.; "Parabolic Growth of a Self-Replicating Hexadeoxynucleotide Bearing a 3'-5'—phosphoamidate Linkage"; 1991, *Angew. Chem. Int. Ed.*, vol. 30, No. 4, pp. 423-426.

Wu et al.; "Studies of nucleotide binding to the ribonucleic acid polymerase by a fluorescence technique"; 1969, *Biochemistry*, vol. 11, pp. 4450-4458.

Yamagata, Y. et al.; "Specific effect of Magnesium ion on 2', 3'-Cyclic amp Synthesis from Adenosine and Trimeta Phosphate in Aqueous Solution"; 1995, *Origins of Life and Evolution of the Biosphere*, vol. 25, pp. 47-52.

"Gene Characterization Kits"; 1988, Stratagene.

U.S. Appl. No. 10/879,493 filed Jun. 28, 2004.
U.S. Appl. No. 10/879,494 filed Jun. 28, 2004.
U.S. Appl. No. 60/519,661 filed Nov. 12, 2003.

\* cited by examiner

2'-TERMINATOR RELATED PYROPHOSPHOROLYSIS ACTIVATED POLYMERIZATION

CROSS-REFERENCES TO RELATED APPLICATIONS

This application is a continuation-in-part of U.S. patent application Ser. No. 10/879,494, entitled "SYNTHESIS AND COMPOSITIONS OF 2'-TERMINATOR NUCLEOTIDES", filed Jun. 28, 2004 and also a continuation-in-part of U.S. patent application Ser. No. 10/879,493, entitled "2'-TERMINATOR NUCLEOTIDE-RELATED METHODS AND SYSTEMS," filed Jun. 28, 2004, the disclosures of which are incorporated by reference.

FIELD OF THE INVENTION

The invention relates generally to nucleic acid chemistry and molecular biology. More specifically, the invention relates to nucleic acid polymerization and amplification involving 2'-terminators.

BACKGROUND OF THE INVENTION

Pyrophosphorolysis activated polymerization (PAP) is a process involving pyrophosphorolysis-mediated activation of pyrophosphorolysis-activatable primers hybridized with target or template nucleic acids followed by extension of the activated primers. Pyrophosphorolysis-activatable primers typically include terminator nucleotides, such as dideoxynucleotides (ddNMPs) at their 3'-termini. These terminator nucleotides must generally be enzymatically removed from such hybridized, blocked primers via pyrophosphorolysis reactions that consume pyrophosphate to produce the activated primers in order for primer extension to proceed. Since primer activation typically requires perfectly matched primers and target nucleic acids, these reactions generally produce limited, if any, non-specific products due, for example, to primer-dimer formation or other false priming artifacts. Exemplary applications of PAP include providing alternative methods for amplifying nucleic acids (e.g., as part of a rare allele detection process, a somatic mutation detection assay, etc.), among other applications.

As referred to above, certain pre-existing PAP-related approaches use ddNMP-terminated primers and efficient ddNMP-incorporating thermostable DNA polymerases (e.g., mutant enzymes that contain an "F to Y" mutation in "Helix O") to effect pyrophosphorolysis of primers with a 3-terminal ddNMP moiety in the presence of pyrophosphate ($PP_i$) after primer binding/annealing to template. These approaches generally have various disadvantages. For example, these techniques typically use very low, limiting concentrations of dNTPs, which reduces (slows down) the extension rate (number of nucleotides polymerized per second). More specifically, when a 3'-terminal ddNMP is released as a ddNTP in these reactions, the very low concentration of dNTPs (i.e., the "pool size") increases the likelihood of reincorporating the ever-increasing concentration of ddNTPs (resulting from successive rounds of PAP) prior to full-length primer extension (required for efficient PCR). This reincorporation is generally undesired, requiring additional PAP to remove the incorporated ddNMP and further contributes to incomplete primer extension and compromises the efficiency of full-length primer extension products in each cycle. Moreover, many of these pre-existing PAP approaches are capable of generating only very short amplicons, e.g., in some cases even shorter than primer dimers. Thus, the PCR cycle efficiency of these previous approaches is generally impaired, typically requiring many cycles to detect low abundance targets.

From the foregoing, it is apparent that additional PAP-related methods are desirable. The present invention provides PAP-related methods that utilize 2'-terminator nucleotides, as well as a variety of additional features that will be apparent upon a complete review of the following disclosure.

SUMMARY OF THE INVENTION

The present invention relates to nucleic acid polymerization and amplification. In certain embodiments, for example, the PAP-related methods provided herein involve the serial coupling of pyrophosphorolysis and polymerization. These methods can be used, e.g., for SNP analysis and rare somatic mutation detection, among many other applications. Aside from PAP-related methods, the invention also provides related reaction mixtures and systems.

To illustrate, the methods and other aspects described herein enhance the general specificity of oligonucleotide-mediated synthesis reactions. For example, analogous to other "hot start" methods (e.g., reversible, chemically-modified enzymes, aptamer- or antibody-mediated "hot start"), "zeroth cycle extension" (pre-PCR) is reduced or eliminated. Unlike these other methods, primer activation is effected at each and every new oligonucleotide-mediated synthesis step. This improves the overall specificity of the reaction, minimizing the generation of unwanted side products. Accordingly, the detection of low copy and even single copy sequences is improved. In addition, the performance in multiplex (where several or many different target are being amplified) amplification reactions is also improved by reducing or eliminating the generation of unintended and undesired, non-specific synthesis products, e.g., primer dimers in the case of PCR.

In one aspect, the invention provides a reaction mixture that includes at least one oligonucleotide (e.g., a primer nucleic acid, a probe nucleic acid, etc.) comprising a 2'-terminator nucleotide (e.g., at a 3'-terminus). In certain embodiments, the oligonucleotide comprises the formula:

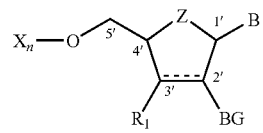

where Z is O or $CH_2$; B is at least one homocyclic ring, at least one heterocyclic ring, at least one aryl group, or combinations thereof; BG is a blocking group; $R_1$ is H, OH, a hydrophilic group, or a hydrophobic group; X is a nucleotide or a nucleotide analog; n is an integer greater than 0; and, ----- represents a single or double bond. Optionally, the oligonucleotide comprises at least one label. In certain embodiments, at least one nucleotide position in the oligonucleotide corresponds to a polymorphic nucleotide position in a target nucleic acid. In some of these embodiments, for example, the 2'-terminator nucleotide corresponds to the polymorphic nucleotide position in the target nucleic acid.

The reaction mixture typically includes additional reagents according to the particular application in which the reaction mixture is utilized. In some embodiments, for example, additional reagents are selected from, e.g., a first biocatalyst comprising a nucleotide removing activity (e.g., a pyrophosphorolysis activity and/or a nuclease activity), a second biocatalyst comprising a nucleotide incorporating activity, a target nucleic acid comprising at least a subsequence that is at least partially complementary to the oligonucleotide, an amplicon, a primer nucleic acid, a probe nucleic acid (e.g., a hybridization probe, a 5'-nuclease probe, a hairpin probe, etc.), an additional nucleotide (e.g., an extendible nucleotide, a terminator nucleotide, a ribonucleoside triphosphate, a deoxyribonucleoside triphosphate, etc.), an additional oligonucleotide (e.g., a primer nucleic acid, a probe nucleic acid, etc.), a soluble light emission modifier, a cosolvent, an intercalating agent, a clinical specimen, a sample, a buffer, a salt, a metal ion, pyrophosphate, glycerol, dimethyl sulfoxide, poly rA, and the like. In some embodiments, the target nucleic acid, the amplicon, the primer nucleic acid, the probe nucleic acid, the additional nucleotide, and/or the additional oligonucleotide comprises at least one label. In certain embodiments, the buffer comprises N-[Tris(hydroxymethyl)methyl]glycine at a concentration of at least 90 mM (e.g., about 95 mM, about 100 mM, about 105 mM, etc.).

In some embodiments, the first biocatalyst comprises a nucleotide incorporating activity (i.e., in addition to the nucleotide removing activity). The nucleotide incorporating activity of the first and/or the second biocatalyst typically comprises a polymerase activity and/or a ligase activity. Optionally, the first and/or the second biocatalyst comprises a nuclease activity. To further illustrate, the first and/or second biocatalyst optionally comprises an enzyme selected from, e.g., a polymerase, a terminal transferase, a reverse transcriptase, a polynucleotide phosphorylase, a ligase, an AP endonuclease, and a telomerase. In certain embodiments, the first and/or second biocatalyst comprises a CS5 DNA polymerase that includes one or more mutations at amino acid positions selected from the group consisting of: G46, L329, Q601, D640, I669, S671, and E678. In some of these embodiments, for example, the mutations comprise a G46E mutation, an L329A mutation, a Q601R mutation, a D640G mutation, an I669F mutation, an S671F mutation, and/or an E678G mutation.

The 2'-terminator nucleotides utilized in the oligonucleotides described herein include various embodiments. In some embodiments, for example, the 2'-terminator nucleotide comprises a 2'-monophosphate-3'-hydroxyl nucleoside. To further illustrate, in certain embodiments the 2'-terminator nucleotide comprises the formula:

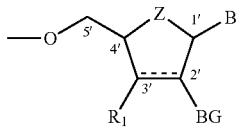

where $R_1$ is H, OH, a hydrophilic group, or a hydrophobic group; B is at least one homocyclic ring, at least one heterocyclic ring, at least one aryl group, or combinations thereof; BG is a blocking group; Z is O or $CH_2$; and ----- represents a single or double bond. Moreover, the 2'-terminator nucleotide is typically non-extendible by one or more nucleotide incorporating biocatalysts selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZO5R polymerase, a E615G Taq DNA polymerase, a Thermus flavus polymerase, a TMA-25 polymerase, a E678G TMA-25 polymerase, a TMA-30 polymerase, a E678G TMA-30 polymerase, a Tth DNA polymerase, a Thermus species SPS-17 polymerase, a E615G Taq polymerase, a Thermus ZO5R polymerase, a T7 DNA polymerase, a Komberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a E. coli RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide analog-incorporating DNA polymerase, a ribonucleotide incorporating DNA polymerase, and the like.

In another aspect, the invention provides a method of removing a nucleotide from an oligonucleotide. The method includes incubating at least one target nucleic acid with: at least a first biocatalyst comprising a nucleotide removing activity (e.g., a pyrophosphorolysis activity and/or a nuclease activity), and at least one oligonucleotide (e.g., a primer nucleic, a probe nucleic acid, etc.) comprising a 2'-terminator nucleotide (e.g., at a 3'-terminus), which oligonucleotide is at least partially complementary to at least a first subsequence of the target nucleic acid, under conditions whereby the first biocatalyst removes at least the 2'-terminator nucleotide from the oligonucleotide to produce a removed 2'-terminator nucleotide and a shortened oligonucleotide, thereby removing the nucleotide from the oligonucleotide. In some embodiments, the method includes incubating the target nucleic acid with the first biocatalyst, the oligonucleotide, and pyrophosphate, which pyrophosphate is added to the removed 2'-terminator nucleotide.

In some exemplary embodiments, the target nucleic acid comprises at least one polymorphic nucleotide position, and the method comprises detecting removal of the 2'-terminator nucleotide from the oligonucleotide, which removal correlates with the oligonucleotide comprising at least one nucleotide position that corresponds to the polymorphic nucleotide position. In these embodiments, the 2'-terminator nucleotide typically corresponds to the polymorphic nucleotide position. In certain embodiments, the oligonucleotide comprises at least one label, and the method comprises detecting a detectable signal emitted from the label. In some of these embodiments, the label comprises a donor moiety and/or an acceptor moiety and the detectable signal comprises light emission, and the method comprises incubating the target nucleic acid with the first biocatalyst, the oligonucleotide, and at least one soluble light emission modifier and detecting the light emission from the donor moiety and/or the acceptor moiety. Optionally, the 2'-terminator nucleotide comprises the donor moiety and/or the acceptor moiety.

To further illustrate, in certain embodiments the first biocatalyst comprises a nucleotide incorporating activity (i.e., in addition to the nucleotide removing activity), and the method comprises incubating the target nucleic acid with the first biocatalyst, the shortened oligonucleotide, and at least one additional nucleotide under conditions whereby the first biocatalyst incorporates the additional nucleotide at a terminus of the shortened oligonucleotide to produce an extended oligonucleotide. Optionally, the method comprises incubating the target nucleic acid with at least a second biocatalyst comprising a nucleotide incorporating activity, the shortened oligonucleotide, and at least one additional nucleotide under conditions whereby the second biocatalyst incorporates the additional nucleotide at a terminus of the shortened oligonucleotide to produce an extended oligonucleotide. To illustrate, the nucleotide incorporating activity typically includes a polymerase activity and/or a ligase activity. The first and/or second biocatalyst typically comprises an enzyme selected from, e.g., a polymerase, a terminal transferase, a reverse transcriptase, a polynucleotide phosphorylase, a ligase, an AP endonuclease, a telomerase, and the like.

In certain embodiments, the first and/or second biocatalyst comprises a CS5 DNA polymerase comprising one or more mutations at amino acid positions selected from, e.g., G46, L329, Q601, D640, I669, S671, and E678. In some of these embodiments, the mutations comprise a G46E mutation, an L329A mutation, a Q601R mutation, a D640G mutation, an I669F mutation, an S671F mutation, and/or an E678G mutation.

In some embodiments, one or more nucleotides of the oligonucleotide extend beyond a terminus of the target nucleic acid when the oligonucleotide and the target nucleic acid hybridize to form a hybridized nucleic acid. In some embodiments, at least one additional oligonucleotide comprises the additional nucleotide. The additional nucleotide comprises an extendible nucleotide and/or a terminator nucleotide. In certain embodiments, the additional nucleotide comprises at least one label, and the method comprises detecting a detectable signal emitted from the label. For example, the label optionally comprises a donor moiety and/or an acceptor moiety and the detectable signal comprises light emission, and the method comprises incubating the target nucleic acid with at least one soluble light emission modifier and detecting the light emission from the label.

To further illustrate, the method optionally includes incubating the target nucleic acid with at least one probe nucleic acid that comprises at least one label, which probe nucleic acid is at least partially complementary to at least a second subsequence of the target nucleic acid, and detecting a detectable signal emitted from the label of the probe nucleic acid or a fragment thereof. In some embodiments, the detectable signal comprises light emission, and the method further comprises incubating the target nucleic acid with at least one soluble light emission modifier and detecting the light emission from the label. For example, the probe nucleic acid optionally comprises a 5'-nuclease probe and the first and/or second biocatalyst extends the shortened oligonucleotide in a 5' to 3' direction and comprises a 5' to 3' exonuclease activity. Optionally, the probe nucleic acid comprises a hybridization probe and/or a hairpin probe.

In certain embodiments, the target nucleic acid comprises at least one polymorphic nucleotide position, and the method comprises detecting extension of the shortened oligonucleotide, which extension correlates with the extended oligonucleotide comprising at least one nucleotide position that corresponds to the polymorphic nucleotide position. In some of these embodiments, the 2'-terminator nucleotide corresponds to the polymorphic nucleotide position.

In another aspect, the invention provides a system that includes (a) at least one container or support comprising an oligonucleotide that comprises a 2'-terminator nucleotide. The system also includes at least one of: (b) at least one thermal modulator configured to thermally communicate with the container or the support to modulate temperature in the container or on the support; (c) at least one fluid transfer component that transfers fluid to and/or from the container or the support; and, (d) at least one detector configured to detect detectable signals produced in the container or on the support. In some embodiments, the system includes at least one controller operably connected to: the thermal modulator to effect modulation of the temperature in the container or on the support, the fluid transfer component to effect transfer of the fluid to and/or from the container or on the support, and/or the detector to effect detection of the detectable signals produced in the container or on the support.

DETAILED DESCRIPTION

I. Definitions

Figure 1:
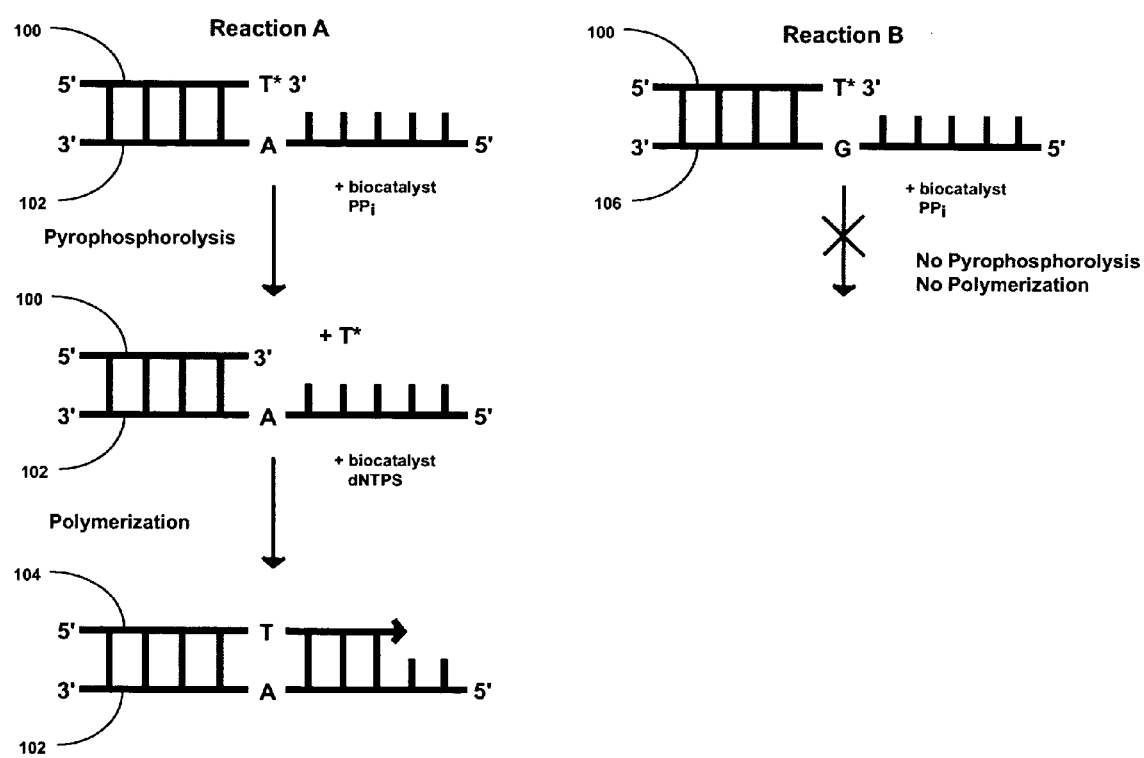
FIG. 1 schematically depicts a single nucleotide polymorphism (SNP) detection assay according to one embodiment of the invention.

Before describing the present invention in detail, it is to be understood that this invention is not limited to particular methods, reaction mixtures, or systems, which can vary. As used in this specification and the appended claims, the singular forms "a," "an," and "the" also include plural referents unless the context clearly provides otherwise. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology, and grammatical variants thereof, will be used in accordance with the definitions set forth below.

A "2'-terminator nucleotide" refers to a nucleotide analog that comprises a blocking group (BG) at the 2'-position of the sugar moiety of the nucleotide. A "blocking group" refers to a chemical group or moiety that typically prevents the extension of a nucleic acid (i.e., a 2'-terminator nucleotide is typically non-extendible by one or more nucleotide incorporating biocatalysts). That is, once a 2'-terminator nucleotide is incorporated into a nucleic acid (e.g., at a 3'-terminal end of the nucleic acid), the blocking group prevents further extension of a nucleic acid by at least one nucleotide incorporating biocatalyst selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZO5R polymerase, a E615G Taq DNA polymerase, a *Thermus flavus* polymerase, a TMA-25 polymerase, a TMA-30 polymerase, a Tth DNA polymerase, a *Thermus* specie SPS-17 polymerase, a E615G Taq polymerase, a *Thermus* ZO5R polymerase, a T7 DNA polymerase, a Komberg DNA polymerase I, a Kienow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a *E. coli* RNA polym erase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like. An exemplary blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. Other 2'-terminator nucleotides are also described further herein and in, e.g., U.S. patent application Ser. No. 10/879,494, entitled "SYNTHESIS AND COMPOSITIONS OF 2'-TERMINATOR NUCLEOTIDES," filed Jun. 28, 2004 by Bodepudi et al., and Ser. No. 10/879,493, entitled "2'-TERMINATOR NUCLEOTIDE-RELATED METHODS AND SYSTEMS," filed Jun. 28, 2004 by Gelfand et al., which are both incorporated by reference.

A "5'-nuclease probe" refers to a labeled oligonucleotide that is capable of producing a detectable signal change upon being cleaved. To illustrate, in certain embodiments a 5'-nuclease probe comprises two labeling moieties and emits radiation of increased intensity after one of the labels is cleaved or otherwise separated from the oligonucleotide. In some of these embodiments, for example, the 5'-nuclease probe is labeled with a 5' terminus quencher moiety and a reporter moiety at the 3' terminus of the probe. In certain embodiments, 5'-nuclease probes are labeled at one or more positions other than, or in addition to, these terminal positions. When the probe is intact, energy transfer typically occurs between the labeling moieties such that the quencher moiety at least in part quenches the fluorescent emission from the acceptor moiety. During an extension step of a polymerase chain reaction, for example, a 5'-nuclease probe bound to a template nucleic acid is cleaved by the 5' to 3' nuclease activity of, e.g., a Taq polymerase or another polymerase having this activity such that the fluorescent emission from the acceptor moiety is no longer quenched. To further illustrate, in certain embodiments 5'-nuclease probes include regions of self-complementarity such that the probes are capable of forming hairpin structures under selected conditions. In these embodiments, 5'-nuclease probes are also referred to herein as "hairpin probes." Exemplary 5'-nuclease probes that can be adapted for use with the methods described herein are also described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference.

An "acceptor moiety" or "acceptor" refers to a moiety that is capable of accepting or absorbing energy transferred from an energy source. In some embodiments, acceptor moieties are also capable of emitting energy (e.g., light, heat, etc.) upon absorbing sufficient amounts of transferred energy. In these embodiments, acceptors are also known as "reporter moieties" or as "reporters". Exemplary acceptor moieties include, but are not limited to, various fluorophores, such as LightCycler®-Red 610 (LC-Red 610), LC-Red 640, LC-Red 670, LC-Red 705, JA-270, CY5, CY5.5, among many others.

An "alcohol group" refers to an organic group that includes at least one hydroxy group.

An "aldehyde group" refers to an organic group that includes the formula CHO.

An "alkenyl group" refers to a linear, branched, or cyclic unsaturated hydrocarbon moiety that comprises one or more carbon-carbon double bonds. Exemplary alkenyl groups include ethenyl, 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2- butenyl, 2-ethyl-3-butenyl, 1,1,2-trimethyl-2-propenyl, 1-ethyl-1-methyl-2-propenyl, 1-ethyl-2-methyl-2-propenyl, and the like. An alkenyl group typically comprises about 1-20 carbon atoms and more typically comprises about 2-15 carbon atoms. Alkenyl groups can be substituted or unsubstituted.

An "alkenylamine group" refers to an amino group that comprises at least one alkenyl group.

An "alkoxy group" refers to an alkyl group that comprises an oxygen atom and includes, e.g., methoxy, ethoxy, propoxy, butoxy, pentoxy, heptyloxy, octyloxy, and the like.

An "alkyl group" refers to a linear, branched, or cyclic saturated hydrocarbon moiety and includes all positional isomers, such as methyl, ethyl, propyl, isopropyl, butyl, pentyl, hexyl, heptyl, octyl, nonyl, 1-methylethyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, n-hexyl, cyclohexyl, n-heptyl, n-octyl, 2-ethylhexyl, n-nonyl, n-decyl and the like. An alkyl group typically comprises about 1-20 carbon atoms and more typically comprises about 2-15 carbon atoms. Alkyl groups can be substituted or unsubstituted.

An "alkylamine group" refers to an amino group that comprises at least one alkyl group.

An "alkynyl group" refers to a linear, branched, or cyclic unsaturated hydrocarbon moiety that comprises one or more carbon-carbon triple bonds. Representative alkynyl groups include, e.g., 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl 1-ethyl-1-methyl-2-propynyl, and the like. An alkynyl group typically comprises about 1-20 carbon atoms and more typically comprises about 2-15 carbon atoms. Alkynyl groups can be substituted or unsubstituted.

An "alkynylamine group" refers to an amino group that comprises at least one alkynyl group.

An "amplicon" refers to a molecule made by copying or transcribing another molecule, e.g., as occurs in transcription, cloning, and/or in a polymerase chain reaction ("PCR") (e.g., strand displacement PCR amplification (SDA), duplex PCR amplification, etc.) or other nucleic acid amplification technique. Typically, an amplicon is a copy of a selected nucleic acid (e.g., a template or target nucleic acid) or is complementary thereto.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using RT-PCR is a form of amplification. Furthermore, the generation of multiple RNA molecules from a single DNA molecule during the process of transcription is also a form of amplification.

An "aryl group" refers to a substituent group of atoms or moiety that is derived from an aromatic compound. Exemplary aryl groups include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

An "aryloxy group" refers an aryl group that comprises an oxygen atom and includes, e.g., phenoxy, chlorophenoxy, methylphenoxy, methoxyphenoxy, butylphenoxy, pentylphenoxy, benzyloxy, and the like.

A "biocatalyst" refers to a catalyst that acts to reduce the activation energy of a chemical reaction involving other compounds or "substrates" in a biological system (e.g., an in vitro biological system, in vivo biological system, etc.). Biocatalysts can have one or more catalytic activities, such as nucleotide removing activities (e.g., pyrophosphorolysis activity, nuclease activity (e.g., endonuclease and/or exonuclease activity), etc.) and/or nucleotide incorporating activities (e.g., polymerase activity, ligase activity, reverse transcriptase activity, etc.).

A "complement" in the context of nucleic acids refers to a nucleic acid, or a segment thereof, that can combine in an antiparallel association or hybridize with at least a subsequence of a nucleic acid. The antiparallel association can be intramolecular, e.g., in the form of a hairpin loop within a nucleic acid, or intermolecular, such as when two or more single-stranded nucleic acids hydridize with one another. Certain bases not commonly found in natural nucleic acids may be included in the nucleic acids referred to herein and include, for example, hypoxanthine, 7-deazaguanine, among many others. Complementarity need not be perfect; stable duplexes or triplexes, for example, may contain mismatched base pairs or unmatched bases. That is, antiparallel associations, whether intramolecular or intermolecular, can occur under certain conditions when nucleic acids are only "partially complementary". Those skilled in the art of nucleic acid chemistry can determine, e.g., duplex or triplex stability by empirically considering a number of variables, such as the length of a region of complementarity, base composition and sequence in a region of complementarity, ionic strength, melting temperature ($T_m$), and incidence of mismatched base pairs.

The term "carboxylic acid group" refers to an organic group that includes the formula COOH.

The term "correlates" refers to establishing a relationship between two or more things. In certain embodiments, for example, the detection of primer extension in a given reaction indicates that the target nucleic acid has a particular polymorphism.

The term "corresponding" means identical to or complementary to a designated nucleotide position or sequence of nucleotides in a nucleic acid. The exact application of the term will be evident to one of skill in the art by the context in which the term is used.

A "donor moiety" refers a moiety that is capable of transferring, emitting, or donating one or more forms of excitation energy to one or more acceptor moieties.

An "ester group" refers to a class of organic compounds that includes the general formula RCOOR', where R and R' are independently selected from an alkyl group, an alkenyl group, an alkynyl group, an aryl group, or combinations thereof.

An "ether group" refers to a linear, branched, or cyclic moiety that comprises two carbon atoms attached to a single oxygen atom. Exemplary ether groups include, e.g., methoxymethyl, methoxyethyl, methoxypropyl, ethoxyethyl, and the like.

An "extendible nucleotide" refers to a nucleotide to which at least one other nucleotide can be added or covalently bonded, e.g., in a reaction catalyzed by a biocatalyst once the extendible nucleotide is incorporated into a nucleotide polymer. Examples of extendible nucleotides include deoxyribonucleotides and ribonucleotides. An extendible nucleotide is typically extended by adding another nucleotide at a 3'-position of the sugar moiety of the extendible nucleotide.

The term "extending" in the context of nucleic acids refers a process in which one or more nucleotides are added to, or otherwise incorporated into, a given nucleic acid.

An "extended oligonucleotide" refers to an oligonucleotide (e.g, a primer nucleic acid) to which one or more additional nucleotides have been added or otherwise incorporated (e.g., covalently bonded to).

A "halo group" refers to a group that comprises a halogen atom, such as F, Cl, Br, or I.

A "hairpin probe" refers to an oligonucleotide that can be used to effect target nucleic acid detection and that includes at least one region of self-complementarity such that the probe is capable of forming a hairpin or loop structure under selected conditions. Typically, hairpin probes include one or more labeling moieties. In one exemplary embodiment, quencher moieties and reporter moieties are positioned relative to one another in the hairpin probes such that the quencher moieties at least partially quench light emissions from the reporter moieties when the probes are in hairpin confirmations. In contrast, when the probes in these embodiments are not in hairpin confirmations (e.g., when the probes are hybridized with target nucleic acids), light emissions the acceptor reporter moieties are generally detectable. Hairpin probes are also known as molecular beacons in some of these embodiments. Hairpin probes can also function as 5'-nuclease probes or hybridization probes in certain embodiments.

A "heterocyclic ring" refers to a monocyclic or bicyclic ring that is either saturated, unsaturated, or aromatic, and which comprises one or more heteroatoms independently selected from nitrogen, oxygen and sulfur. A heterocyclic ring may be attached to the sugar moiety, or analog thereof, of a nucleotide of the invention via any heteroatom or carbon atom. Exemplary heterocyclic rings include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, quinazolinyl, and the like.

A "homocyclic ring" refers to a saturated or unsaturated (but not aromatic) carbocyclic ring, such as cyclopropane, cyclobutane, cyclopentane, cyclohexane, cycloheptane, cyclohexene, and the like.

A "hybridization probe" refers an oligonucleotide that includes at least one labeling moiety that can be used to effect target nucleic acid detection. In some embodiments, hybridization probes function in pairs. In some of these embodiments, for example, a first hybridization probe of a pair includes at least one donor moiety at or proximal to its 3'-end, while the second hybridization probe of the pair includes at least one acceptor moiety (e.g., LC-Red 610, LC-Red 640, LC-Red 670, LC-Red 705, JA-270, CY5, or CY5.5) at or proximal to its 5'-end. The probes are typically designed such that when both probes hybridize with a target or template nucleic acid (e.g., during a PCR), the first hybridization probe binds to the 5'-end side or upstream from the second hybridization probe and within sufficient proximity for energy transfer to occur between the donor and acceptor moieties to thereby produce a detectable signal. Typically, the second hybridization probe also includes a phosphate or other group on its 3'-end to prevent extension of the probe during a PCR.

Nucleic acids "hybridize" or "anneal" in a base-pairing interaction of one polynucleotide with another polynucleotide (typically an antiparallel polynucleotide) that results in formation of a duplex or other higher-ordered structure, typically termed a hybridization complex. The primary interaction between the antiparallel polynucleotides is typically base specific, e.g., A/T and G/C, by Watson/Crick and/or Hoogsteen-type interactions. It is not a requirement that two polynucleotides have 100% complementarity over their full length to achieve hybridization. In some aspects, a hybridization complex can form from intermolecular interactions, or alternatively, can form from intramolecular interactions. Hybridization occurs due to a variety of well-characterized forces, including hydrogen bonding, solvent exclusion, and base stacking. An extensive guide to nucleic hybridization may be found in Tijssen, *Laboratory Techniques in Biochemistry and Molecular Biology-Hybridization with Nucleic Acid Probes*, part I, chapter 2, "Overview of principles of hybridization and the strategy of nucleic acid probe assays," Elsevier (1993).

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include donor moieties, acceptor moieties, fluorescent labels, non-fluorescent labels, calorimetric labels, chemiluminescent labels, bioluminescent labels, radioactive labels, mass-modifying groups, antibodies, antigens, biotin, haptens, and enzymes (including, e.g., peroxidase, phosphatase, etc.).

A "light emission modifier" refers to a substance that noncovalently associates with a nucleic acid in a mixture and that changes the detectable emission of radiation from a radiation source associated with the nucleic acid when the substance is proximal to the radiation source. In some embodiments, for example, certain light emission modifiers described herein reduce or quench the emission of light that would otherwise be emitted (e.g., a baseline emission of light) from oligonucleotides that include at least one light-emitting moiety (e.g., 5'-nuclease probes, etc.) when the light emission modifiers are contacted with those oligonucleotides. Light emission modifiers are typically soluble and in these embodiments are also referred to as "soluble quenchers" or "soluble light emission modifiers". In addition, the extent that a light emission modifier modifies the emission of light from a given oligonucleotide is typically proportional to the length of that oligonucleotide. For example, if the oligonucleotide is cleaved in a 5'-nuclease reaction, a particular light emission modifier will generally modify the emission of light from labeled fragments of the oligonucleotide to a lesser extent that from the intact oligonucleotide. Exemplary light emission modifiers include various diazine and thiazines dyes, which are described further herein and in, e.g., U.S. patent application Ser. No. 11/474,062, entitled "LIGHT EMISSION MODIFIERS AND THEIR USES IN NUCLEIC ACID DETECTION, AMPLIFICATION AND ANALYSIS," filed Jun. 23, 2006 by Gupta et al., which is incorporated by reference.

A "mixture" refers to a combination of two or more different components. A "reaction mixture" refers a mixture that comprises molecules that can participate in and/or facilitate a given reaction or assay. To illustrate, an amplification reaction mixture generally includes a solution containing reagents necessary to carry out an amplification reaction, and typically contains primers, a biocatalyst (e.g., a nucleic acid polymerase, a ligase, etc.), dNTPs, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and that reaction components are combined prior to the reaction to create a complete reaction mixture. Furthermore, it will be understood by one of skill in the art that reaction components are packaged separately for commercialization and that useful commercial kits may contain any subset of the reaction or assay components, which includes the biomolecules of the invention.

A "moiety" or "group" refers to one of the portions into which something, such as a molecule, is or can be divided (e.g., a functional group, substituent group, or the like). For example, an oligonucleotide described herein includes at least one donor moiety and/or at least one acceptor moiety in certain embodiments.

The term "mutation" refers to a nucleic acid that has been altered in its nucleic acid sequence or an encoded protein product of a nucleic acid that has been altered in its amino acid sequence relative to an unaltered or native form of the nucleic acid or encoded protein product. Such alterations include, for example, point mutations or substitutions, deletions and insertions.

A "non-extendible" nucleotide refers to a nucleotide, which upon incorporation into a nucleic acid prevents further extension of the nucleic acid, e.g., by at least one biocatalyst.

The term "nucleic acid" or "polynucleotide" refers to a polymer that can be corresponded to a ribose nucleic acid (RNA) or deoxyribose nucleic acid (DNA) polymer, or an analog thereof. This includes polymers of nucleotides such as RNA and DNA, as well as modified forms thereof, peptide nucleic acids (PNAs), locked nucleic acids (LNA™s), and the like. In certain embodiments, a nucleic acid can be a polymer that includes multiple monomer types, e.g., both RNA and DNA subunits. A nucleic acid can be or can include, e.g., a chromosome or chromosomal segment, a vector (e.g., an expression vector), an expression cassette, a naked DNA or RNA polymer, the product of a polymerase chain reaction (PCR), an oligonucleotide, a probe, a primer, etc. A nucleic acid can be, e.g., single-stranded, double-stranded, triple-stranded, etc and is not limited to any particular length. Unless otherwise indicated, a particular nucleic acid sequence optionally comprises or encodes complementary sequences, in addition to any sequence explicitly indicated.

Nucleic acids are not limited to molecules having naturally occurring polynucleotide sequences or structures, naturally occurring backbones, and/or naturally occurring internucleotide linkages. For example, nucleic acids containing one or more carbocyclic sugars are also included within this definition (Jenkins et al. (1995) *Chem. Soc. Rev.* pp 169-176, which is incorporated by reference). To further illustrate, although a nucleic acid will generally contain phosphodiester bonds, in some cases nucleic acid analogs are included that have alternate backbones. These include, without limitation, phosphoramide (Beaucage et al. (1993) *Tetrahedron* 49(10): 1925 and the references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26:1419), phosphorothioate (Mag et al. (1991) *Nucleic Acids Res.* 19:1437 and U.S. Pat. No. 5,644,048), phosphorodithioate (Briu et al. (1989) *J. Am. Chem. Soc.* 111:2321), O-methylphophoroamidite linkages (Eckstein, *Oligonucleotides and Analogues: A Practical Approach*, Oxford University Press (1992)), and peptide nucleic acid backbones and linkages (Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207), which references are each incorporated by reference. Other analog nucleic acids include those with positively charged backbones (Denpcy et al. (1995) *Proc. Natl. Acad. Sci. USA* 92:6097); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; *Tetrahedron Lett.* 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which are each incorporated by reference. Several nucleic acid analogs are also described in, e.g., Rawls, *C & E News Jun.* 2, 1997 page 35, which is incorporated by reference. Modifications of the ribose-phosphate backbone may be done to facilitate the addition of additional moieties, such as labeling moieties, or to alter the stability and half-life of such molecules in physiological environments.

In addition to naturally occurring heterocyclic bases that are typically found in nucleic acids (e.g., adenine, guanine, thymine, cytosine, and uracil), nucleic acid analogs also include those having non-naturally occurring heterocyclic or other modified bases. To illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like. Many non-naturally occurring bases are also described in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference.

Additional examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2. 1]BICYCLO NUCLEOSIDES," by Kochkine et al. that published May 15, 2003, which are each incorporated by reference.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g., a ribose sugar, etc.), a derivative of a sugar moiety, or a functional equivalent of a sugar moiety (e.g., an analog, such as carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. To illustrate, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like. A "thermostable enzyme" refers to an enzyme that is stable to heat, is heat resistant, and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known to persons skilled in the art and are exemplified in U.S. Pat. No. 4,683,202, entitled "PROCESS FOR AMPLIFYING NUCLEIC ACID SEQUENCES," issued Jul. 28, 1987 to Mullis and U.S. Pat. No. 4,683,195, entitled "PROCESS FOR AMPLIFYING, DETECTING, AND/OR-CLONING NUCLEIC ACID SEQUENCES," issued Jul. 28, 1987 to Mullis et al., which are both incorporated by reference. See also, U.S. Pat. No. 4,965,188, which is also incorporated by reference. To further illustrate, a "thermostable polymerase" refers to an enzyme that is suitable for use in a temperature cycling reaction, such as a polymerase chain reaction ("PCR"). For a thermostable polymerase, enzymatic activity refers to the catalysis of the combination of the nucleotides in the proper manner to form primer extension products that are complementary to a template nucleic acid.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "polymorphism" or "polymorphic nucleotide position" refers to a site or sites of a nucleic acid that might have one of a plurality of genotypes. The polymorphism can be any polymorphism known to those of skill in the art including possible mutations, insertions or deletions. The polymorphism can be at one site of the nucleic acid or at multiple sites of the nucleic acid. For the purposes of the present invention "a polymorphism" can refer to a polymorphism that is at one site of a nucleic acid or to one particular site of a multiple-site polymorphism. In certain embodiments, the polymorphism need not be well known or even known to those of skill in the art. The polymorphism can simply be any difference between a control nucleic acid and a target nucleic acid.

A "primer nucleic acid" or "primer" is a nucleic acid that can hybridize to a target or template nucleic acid and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide). Although other primer nucleic acid lengths are optionally utilized, they typically comprise hybridizing regions that range from about 8 to about 100 nucleotides in length. Short primer nucleic acids generally require cooler temperatures to form sufficiently stable hybrid complexes with template nucleic acids. A primer nucleic acid that is at least partially complementary to a subsequence of a template nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include donor moieties, acceptor moieties, quencher moieties, radioisotopes, electron-dense reagents, enzymes (as commonly used in performing ELISAs), biotin, or haptens and proteins for which antisera or monoclonal antibodies are available. Many of these and other labels are described further herein and/or are otherwise known in the art. One of skill in the art will recognize that, in certain embodiments, primer nucleic acids can also be used as probe nucleic acids.

The term "probe nucleic acid" or "probe" refers to a labeled or unlabeled oligonucleotide capable of selectively hybridizing to a target or template nucleic acid under suitable conditions. Typically, a probe is sufficiently complementary to a specific target sequence contained in a nucleic acid sample to form a stable hybridization duplex with the target sequence under a selected hybridization condition, such as, but not limited to, a stringent hybridization condition. A hybridization assay carried out using a probe under sufficiently stringent hybridization conditions permits the selective detection of a specific target sequence. The term "hybridizing region" refers to that region of a nucleic acid that is exactly or substantially complementary to, and therefore capable of hybridizing to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site for attaching the probe sequence to a solid support. A probe of the invention is generally included in a nucleic acid that comprises one or more labels (e.g., donor moieties, acceptor moieties, and/or quencher moieties), such as a 5'-nuclease probe, a hybridization probe, a fluorescent resonance energy transfer (FRET) probe, a hairpin probe, or a molecular beacon, which can also be utilized to detect hybridization between the probe and target nucleic acids in a sample. In some embodiments, the hybridizing region of the probe is completely complementary to the target sequence. However, in general, complete complementarity is not necessary (i.e., nucleic acids can be partially complementary to one another); stable hybridization complexes may contain mismatched bases or unmatched bases. Modification of the stringent conditions may be necessary to permit a stable hybridization complex with one or more base pair mismatches or unmatched bases. Sambrook et al., *Molecular Cloning: A Laboratory Manual,* 3rd Ed., Cold Spring Harbor Laboratory Press, Cold Spring Harbor, N.Y. (2001), which is incorporated by reference, provides guidance for suitable modification. Stability of the target/probe hybridization complex depends on a number of variables including length of the oligonucleotide, base composition and sequence of the oligonucleotide, temperature, and ionic conditions. One of skill in the art will recognize that, in general, the exact complement of a given probe is similarly useful as a probe. One of skill in the art will also recognize that, in certain embodiments, probe nucleic acids can also be used as primer nucleic acids.

The term "pyrophosphorolysis" refers to the removal of one or more nucleotides from a nucleic acid in the presence of pyrophosphate ($PP_i$) to generate one or more nucleoside triphosphates.

A "quencher moiety" or "quencher" refers to a moiety that is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Certain quenchers may re-emit the energy absorbed from, e.g., a fluorescent dye in a signal characteristic for that quencher and thus, a quencher can also be an acceptor moiety. This phenomenon is generally known as fluorescent resonance energy transfer or FRET. Alternatively, a quencher may dissipate the energy absorbed from a fluorescent dye in a form other than light, such as heat. Molecules commonly used in FRET applications include, for example, fluorescein, FAM, JOE, rhodamine, R6G, TAMRA, ROX, DABCYL, and EDANS. Whether a fluorescent dye is an acceptor or a quencher is defined by its excitation and emission spectra, and the fluorescent dye with which it is paired. For example, FAM is most efficiently excited by light with a wavelength of 488 nm, and emits light with a spectrum of 500 to 650 nm, and an emission maximum of 525 nm. FAM is a suitable donor moiety for use with, e.g., TAMRA as a quencher, which has at its excitation maximum 514 nm. Exemplary non-fluorescent or dark quenchers that dissipate energy absorbed from a fluorescent dye include the Black Hole Quenchers™ marketed by Biosearch Technologies, Inc. (Novato, Calif., USA). The Black Hole Quenchers™ are structures comprising at least three radicals selected from substituted or unsubstituted aryl or heteroaryl compounds, or combinations thereof, in which at least two of the residues are linked via an exocyclic diazo bond (see, e.g., International Publication No. WO 01/86001, entitled "DARK QUENCHERS FOR DONOR-ACCEPTOR ENERGY TRANSFER," published Nov. 15, 2001 by Cook et al., which is incorporated by reference). Exemplary quenchers are also provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

A "silyl group" refers to a class of compounds that includes the general formula $SiRR_1R_2$, where R, $R_1$, and $R_2$ are independently an H, an alkyl group, an alkenyl group, an alkynyl group, an aryl group, or a combination of such groups.

A "subsequence" refers to any portion of an entire biopolymer sequence, such as a nucleic acid sequence.

A "system" in the context of analytical instrumentation refers a group of objects and/or devices that form a network for performing a desired objective.

A "target" refers to a biomolecule (e.g., a nucleic acid, etc.), or portion thereof, that is to be amplified, detected, and/or otherwise analyzed.

A "terminator nucleotide" refers to a nucleotide, which upon incorporation into a nucleic acid substantially prevents further extension of the nucleic acid, e.g., by at least one nucleotide incorporating biocatalyst.

A "thioether group" refers to a linear, branched, or cyclic moiety that comprises two carbon atoms attached to a single sulfur atom and includes, e.g., methylthiomethyl, methylthioethyl, methylthiopropyl, and the like.

II. Introduction

The present invention relates to various applications for oligonucleotides that include 2'-terminator nucleotides typically at their 3'-termini and accordingly are blocked. That is, the 2'-terminator nucleotides generally prevent extension by one or more of the biocatalysts referred to herein. These blocked oligonucleotides, however, are generally "activatable" in that they can be extended if the 2'-terminator nucleotides are removed. In some embodiments, for example, the oligonucleotides described herein are activated via pyrophosphorolysis, which is simply the reverse reaction of nucleic acid polymerization. More specifically, in the presence of pyrophosphate, 2'-terminator nucleotides can be removed from duplex nucleic acids to produce nucleoside triphosphate and 3'-termini shortened oligonucleotides, which can be extended in polymerization reactions. The serial coupling of pyrophosphorolysis and polymerization in PAP-related applications generally provides for improved specificity relative to processes lacking pyrophosphorolysis activation, because non-specific amplification under PAP conditions necessitates both mismatch pyrophosphorolysis and misincorporation by the biocatalyst, which is a rare event. Moreover, the proofreading 3'-5' exonuclease activity of certain enzymatic biocatalysts described herein surprisingly does not remove the blocking groups from the primers described herein (i.e., activate the primers), either when the primers are in solution or annealed to corresponding template nucleic acids. Accordingly, the proofreading activity of these enzymes typically provides higher fidelity synthesis of primer extension products than various pre-existing PAP-related approaches that utilize enzymes lacking proofreading activity. As exemplified in this disclosure, the blocked oligonucleotides described herein can be used in essentially any polymerization or amplification process, including SNP analysis and rare somatic mutation detection, among many other applications that will be apparent to persons of skill in the art.

As mentioned above, the PAP-related approaches described herein (e.g., involving ribonucleotide-incorporating thermoactive and/or thermostable DNA polymerases) generally improve the specificity of oligonucleotide-mediated synthesis reactions relative to pre-existing approaches. Further, relatively high, and not kinetically-limiting, concentrations of dNTPs and NTPs are generally permissible. This typically leads to faster extension rates by not "starving" the enzyme for substrate unlike many previous PAP-related approaches. In addition, this also generally means that the likelihood of reincorporation of a pyrophosphorolysis-released 2'-terminator triphosphate is much lower. Furthermore, the enzymes referred to herein typically have fast extension rates with dNTPs (and NTPs). This shortens the necessary extension time, increases the efficiency of full-length primer extension, and increases the PCR efficiency of these methods. Details relating to these enzymes are also described in, e.g., Ser. No. 60/852,882, entitled "MUTANT DNA POLYMERASES AND RELATED METHODS", filed Oct. 18, 2006 by Bauer et al., which is incorporated by reference. Moreover, the blocked primers referred to herein are economically and easily prepared. In particular, the synthesis of these blocked oligonucleotides is also described in, e.g., Ser. No. 11/583,605, entitled "SYNTHESIS AND COMPOSITIONS OF NUCLEIC ACIDS COMPRISING 2'-TERMINATOR NUCLEOSIDES", filed Oct. 18, 2006 by Bodepudi et al., which is incorporated by reference.

To further illustrate, FIG. 1 schematically illustrates an exemplary single nucleotide polymorphism (SNP) detection assay. As shown in Reaction A, primer nucleic acid 100 is hybridized with template nucleic acid 102. Primer 100 is blocked, because it includes a 2'-terminator nucleotide (T*) at its 3' terminus. In addition, the position of the 2'-terminator nucleotide of primer 100 corresponds to a polymorphic position in template 102 and in the instance shown, is complementary to the nucleotide in that position (A). In the presence of pyrophosphate ($PP_i$) and a biocatalyst having pyrophosphorolysis activity, a pyrophosphorolysis reaction proceeds such that the 2'-terminator nucleotide is removed to thereby activate primer 100. As further shown, activated primer 100 is then extended in the presence of a biocatalyst (e.g., a nucleic acid polymerase, etc.) and dNTPs (or mixtures dNTPs and NTPs (i.e., ribonucleotides)) of in a polymerization reaction to produce extended primer 104, which correlates with template 102 having allele A at the polymorphic position. Extended primer 104 can be detected using essentially any available detection technique, including the use of 5'-nuclease probes, hairpin probes, hybridization probes, mass spectrometry, or the like. To further illustrate, in certain embodiments T* is labeled with a reporter moiety. In some of these embodiments, another position in primer 100 is labeled with a quencher moiety within sufficient proximity to the reporter moiety to quench light emission from the reporter moiety. In these embodiments, if pyrophosphorolysis proceeds (e.g., as shown in Reaction A of FIG. 1), then light emission from the reporter moiety will be detectable as T* is removed from primer 100 and sufficiently separated from the quencher moiety. In contrast to Reaction A, the 2'-terminator nucleotide of primer 100 is not complementary to the nucleotide (G) at the polymorphic position in template nucleic acid 106 in Reaction B. As a consequence of this mismatch, little, if any, pyrophosphorolysis or polymerization occurs even in the presence of a biocatalyst and $PP_i$ and accordingly, little, if any, primer extension takes place. Many other variations of this PAP-related process can also be utilized with the pyrophosphorolysis-activatable oligonucletides described herein. Some additional representative illustrations of these are described further below.

Aside from various methods, the invention also provides reaction mixtures that include pyrophosphorolysis-activatable oligonucletides and related systems. These and many other features of the present invention are described below, including in the examples.

III. 2'-Terminator Nucleotides

The present invention relates to methods, reaction mixtures, systems and other aspects that involve the use of oligonucleotides that include 2'-terminator nucleotides (i.e., 2'-terminator blocked oligonucleotides). Oligonucleotide synthesis and related nucleic acid synthesis reagents are described further below. To illustrate, the nucleotides utilized in various embodiments of the invention typically include a hydroxyl group at a 3'-position of an intact sugar ring and a blocking group (e.g., a negatively charged blocking group, a bulky blocking group, and/or the like) at a 2'-position of the sugar moiety. Certain biocatalysts described herein comprise the ability to extend primer nucleic acids with these 2'-terminator nucleotides in a template directed manner. Upon incorporation of a 2'-terminator nucleotide at a 3'-terminal end of a primer nucleic acid, the nucleic acid is typically rendered non-extendible by the biocatalyst. In addition, some biocatalysts include the ability to remove 2'-terminator nucleotides from oligonucleotides, e.g., via pyrophosphorolysis. Additional details relating to 2'-terminator nucleotides, 2'-terminator blocked oligonucleotides, synthesis, and/or related biocatalysts are also described in, e.g., Ser. No. 60/852,882, entitled "MUTANT DNA POLYMERASES AND RELATED METHODS", filed Oct. 18, 2006 by Bauer et al., Ser. No. 11/583,605, entitled "SYNTHESIS AND COMPOSITIONS OF NUCLEIC ACIDS COMPRISING 2'-TERMINATOR NUCLEOSIDES", filed Oct. 18, 2006 by Bodepudi et al., U.S. patent application Ser. No. 10/879,493, entitled "2'-TERMINATOR NUCLEOTIDE-RELATED METHODS AND SYSTEMS," filed Jun. 28, 2004 by Gelfand et al., and U.S. patent application Ser. No. 10/879,494, entitled "SYNTHESIS AND COMPOSITIONS OF 2'-TERMINATOR NUCLEOTIDES," filed Jun. 28, 2004 by Bodepudi et al., which are each incorporated by reference.

The 2'-terminator nucleotides utilized in the methods and other aspects of the invention generally include the formula:

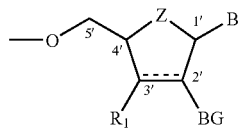

in which $R_1$ is H, OH, a hydrophilic group, or a hydrophobic group; B is at least one homocyclic ring, at least one heterocyclic ring (with or without exocyclic heteroatoms), at least one aryl group, or combinations thereof; BG is a blocking group; Z is O or $CH_2$; and -----represents a single or double bond. In some embodiments, these nucleosides and nucleotides are labeled. Further, these 2'-terminator nucleotides generally comprise 1, 2, 3, or more phosphate groups attached at the 5' position. In one embodiment, for example, a 2'-terminator nucleotide comprises a 2'-monophosphate-3'-hydroxyl-5'-triphosphate nucleoside.

Figure 2A:
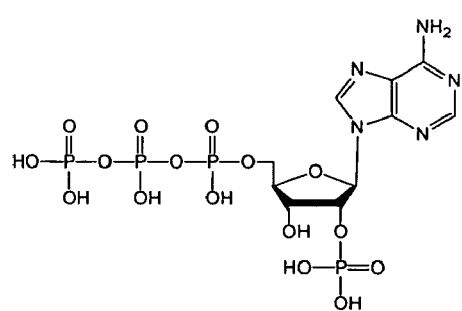
FIGS. 2A-D schematically illustrate exemplary 2'-terminator nucleotides.
Figure 2B:
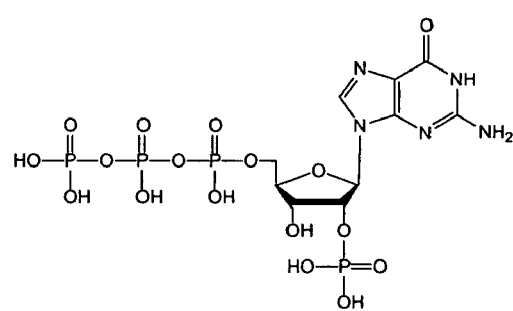
Figure 2C:
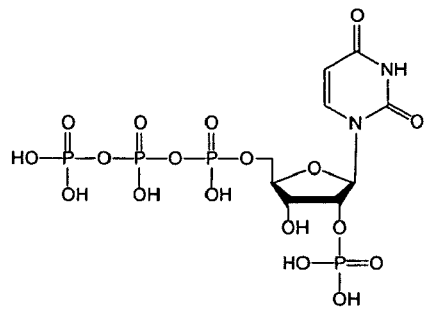
Figure 2D:
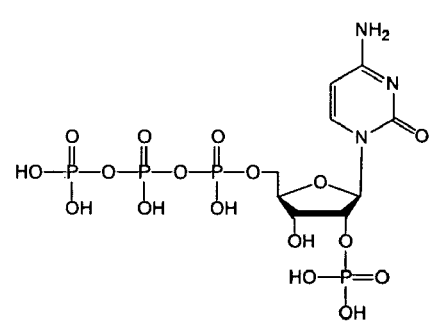
Figure 3A:
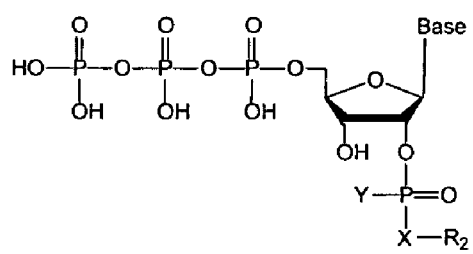
FIGS. 3A and B schematically show some embodiments of 2'-terminator nucleotides.
Figure 3B:
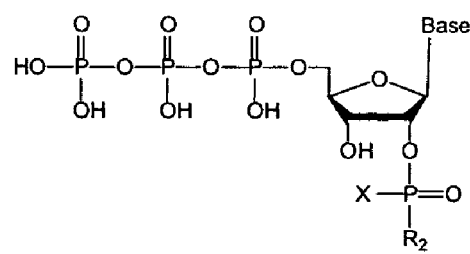

FIGS. 2A-D schematically illustrate certain embodiments of 2'-terminator nucleotides. In particular, FIG. 2A schematically shows an adenosine tetraphosphate terminator nucleotide, FIG. 2B schematically depicts a guanosine tetraphosphate terminator nucleotide, FIG. 2C schematically illustrates a uridine tetraphosphate terminator nucleotide, and FIG. 2D schematically shows a cytidine tetraphosphate terminator nucleotide.

A. Bases

Essentially any heterocyclic ring or aryl group (i.e., as the base or B group) that can base pair with another nucleic acid, e.g., via a hydrogen bond or through a base stacking mechanism is optionally included at the 1' position of the sugar moiety of a 2'-terminator nucleoside or nucleotide. Accordingly, no attempt is made herein to describe all of the possible groups that can be utilized. However, certain representative B groups are provided below for purposes of illustration. In some embodiments, for example, B comprises the formula:

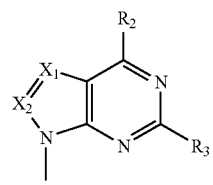

where $X_1$ and $X_2$ are independently selected from $CR_8$ and N; $R_2$ is H, OH, or $NR_4R_5$; $R_3$ is H, OH, or $NR_6R_7$; $R_4$, $R_5$, $R_6$, and $R_7$ are independently selected from H, an alkyl group, an alkenyl group, a benzyl group, an aryl group, an aryloxy group, and combinations thereof; and $R_8$ is H, a halo group, an alkyl group, an alkenyl group, an alkynyl group, an alkyl amine group, an alkenyl amine group, an alkynyl amine group, an alkyl alcohol group, an alkenyl alcohol group, an alkynyl alcohol group, unsubstituted polyethylene glycol, or substituted polyethylene glycol.

In other embodiments, B comprises the formula:

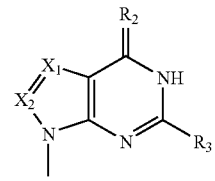

where $X_1$ and $X_2$ are independently selected from CH and N; $R_2$ is O or S; $R_3$ is H, OH, or $NR_4R_5$; and $R_4$ and $R_5$ are independently selected from H, an alkyl group, an alkenyl group, a benzyl group, an aryl group, and combinations thereof.

In some embodiments, B comprises the formula:

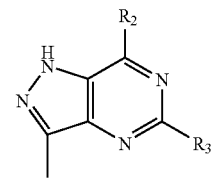

where $R_2$ is H, OH, or $NR_4R_5$; $R_3$ is H, OH, or $NR_6R_7$; and $R_4$, $R_5$, $R_6$, and $R_7$ are independently selected from H, an alkyl group, an alkenyl group, an alkynyl group, a benzyl group, an aryl group, and combinations thereof.

In some embodiments, B comprises the formula:

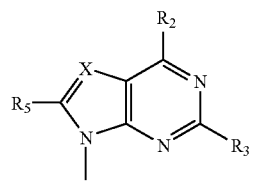

where X is CH or N; $R_2$ and $R_3$ are independently selected from H, OH, and $NHR_4$; $R_4$ is H, an alkyl group, an alkenyl group, a benzyl group, an aryl group, or combinations thereof; and, $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

In other embodiments, B comprises the formula:

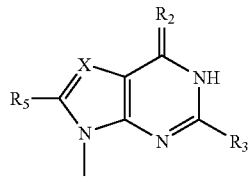

where X is CH or N; $R_2$ is O or S; $R_3$ is H, OH, or $NHR_4$; $R_4$ is H, an alkyl group, an alkenyl group, a benzyl group, an aryl group, or combinations thereof; and $R_5$ is OH, $NH_2$, SH, a halo group, an ether group, a thioether group, an alkyl group, an alkenyl group, an alkynyl group, an alkylamine group, an alkenylamine group, an alkynylamine group, or combinations thereof.

In certain embodiments, B comprises the formula:

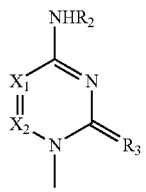

where $X_1$ and $X_2$ are independently selected from CH and N; $R_2$ is selected from H, an alkyl group, an alkenyl group, a benzyl group, an aryl group, an aryloxy group, or combinations thereof; and $R_3$ is O or S.

In other embodiments, B comprises the formula:

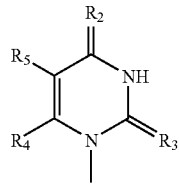

where $R_2$ and $R_3$ are independently selected from O and S; and $R_4$ and $R_5$ are independently selected from H, $NH_2$, SH, OH, an alkyl group, an alkenyl group, an alkynyl group, a benzyl group, an aryl group, an aryloxy group, an alkoxy group, a halo group, and combinations thereof.

In some embodiments, B comprises the formula:

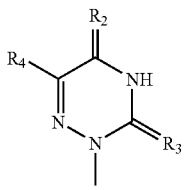

where $R_2$ and $R_3$ are independently selected from O and S; and $R_4$ is H, $NH_2$, SH, OH, an alkyl group, an alkenyl group, a benzyl group, an aryl group, an aryloxy group, an alkoxy group, a halo group, or combinations thereof.

In other embodiments, B comprises the formula:

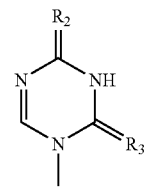

where $R_2$ and $R_3$ are independently selected from O and S.

In some embodiments, B comprises the formula:

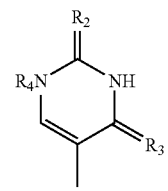

where $R_2$ and $R_3$ are independently selected from O and S, and $R_4$ is H, an alkyl group, an alkenyl group, or an alkynyl group.

In other embodiments, B comprises the formula:

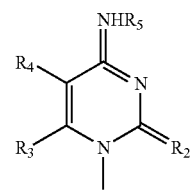

where $R_2$ is O or S; $R_3$ and $R_4$ are independently selected from H, $NH_2$, SH, OH, COOH, $COOCH_3$, $COOCH_2CH_3$, CHO, $NO_2$, CN, an alkyl group, an alkenyl group, an alkynyl group, a benzyl group, an aryl group, an aryloxy group, an alkoxy group, a halo group, and combinations thereof; and $R_5$ is an alkyl group, an alkenyl group, an aryl group, a benzyl group, or combinations thereof.

B. Blocking Groups

The blocking groups (BG) utilized at the 2' position of the sugar moiety also include various embodiments. In some embodiments, for example, BG is a negatively charged group and/or a bulky group. To further illustrate, BG is optionally selected from, e.g., CN, $NO_2$, $N_3$, a halo group, an ether group, an alkyl ether group, an aryl ether group, an aldehyde group, a carboxylic acid group, an ester group, an amino group, $OCH_3$, $OCH_2COOH$, an O-silylether group, a keto group, an O-lactone group, an O-alkyl group, an O-cyclic alkyl group, an O-alkenyl group, an O-alkynl group, a carbamate group, an imide group, an amide group, and combinations thereof. More specifically, BG optionally comprises the formula:

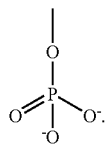

In other embodiments, BG comprises the formula:

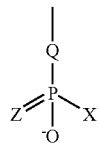

where Q is O, S, or NH; X is H, OH, CH$_3$, BH$_3$, F, or SeH; and Z is O, S, or Se. FIG. 2B schematically depicts one nucleotide comprising a blocking group having this formula. To further illustrate, BG optionally comprises the formula:

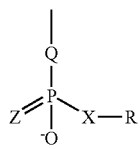

where Q is O, S, or NH; X is O, S, or NH; Z is O, S, or Se; and R is an alkyl group, an alkenyl group, or an alkynyl group. FIG. 2A schematically depicts one 2'-terminator nucleotide comprising a blocking group having this formula. In another exemplary embodiment, BG comprises the formula:

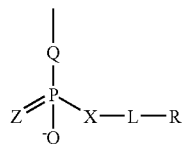

where Q is O, S, or NH; X is O, S, or NH; Z is O, S, or Se; L is —CONH(CH$_2$)$_n$NH—, —CO(CH$_2$)$_n$NH—, or —CONH (CH$_2$CH$_2$O)$_n$CH$_2$CH$_2$NH—; n is an integer greater than 0; and R is NH$_2$, SH, COOH, a quencher moiety, a reporter moiety, biotin, or a affinity moiety.

IV. Synthesis Of 2'-Terminator Nucleosides and Nucleotides

The 2'-terminator nucleosides and nucleotides included in the oligonucleotides utilized as described herein can be synthesized using various methods. For example, one method of producing a labeled, non-extendible nucleotide includes attaching at least one phosphate group to a 5'-position of a sugar moiety of a nucleoside (e.g., a ribonucleoside, a carbocyclic nucleoside, etc.), and attaching at least one blocking group to a 2'-position of the sugar moiety of the nucleoside. Exemplary blocking groups and bases that are optionally included in the nucleosides utilized in this method are described herein. The method also includes attaching at least one label to the sugar moiety, the blocking group, and/or a base of the nucleoside. Suitable labels are described further below.

To further illustrate, one method of producing a 2'-monophosphate nucleoside that is optionally utilized includes reacting a nucleotide comprising the formula:

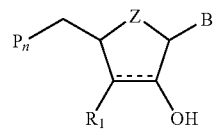

where P is at least one phosphate group; n is an integer greater than 0; R$_1$ is H, OH, a hydrophilic group, or a hydrophobic group; B is at least one homocyclic ring, at least one heterocyclic ring, at least one aryl group, or combinations thereof; Z is O or CH$_2$; and ----represents a single or double bond; with trisodium trimetaphosphate (NaPO$_3$)$_3$ under conditions effective to produce the 2'-monophosphate nucleoside. In certain embodiments, for example, the nucleotide comprises two phosphate groups, whereas in others, the nucleotide comprises three phosphate or more groups. Effective conditions to produce the nucleotide generally include performing the reactions in solution at an alkaline pH. For example, the synthesis is typically performed at a pH greater than about 8.0, more typically at a pH greater than about 10.0, and still more typically at a pH greater than about 12.0 (e.g., at about 12.5, 13.0, 13.5, or 14.0). Various basic compounds can be used to adjust the pH of the reaction mixture including, e.g., KOH and NaOH among many others that are widely known in the art. The nucleotide is typically the limiting reagent. Although other temperature conditions are optionally utilized, these synthesis reactions are generally performed at or near room temperature (i.e., between about 20° C. and about 30° C., e.g., at about 23° C., 24° C., 25° C., 26° C., etc.). In addition, these reactions are generally allowed to proceed for at least about 4 hours, typically for at least about 6 hours, and even more typically for at least about 16 hours.

In addition, various regiospecific or at least regioselective synthetic pathways can also be utilized such that product purification is generally minimized, if not entirely eliminated. These synthetic pathways typically include the use of various protecting groups (e.g., TBDMS, SiR, TOM, BOC, etc.) at the 3'-position of sugar moieties. The synthesis of 2'-terminator nucleotides, including regiospecific synthesis pathways are also described in, e.g., U.S. patent application Ser. No. 10/879,494, entitled "SYNTHESIS AND COMPOSITIONS OF 2'-TERMINATOR NUCLEOTIDES," filed Jun. 28, 2004 by Bodepudi et al., which is incorporated by reference.

Various synthetic techniques that can be adapted for use in the synthesis protocols of the present invention are generally known and described in, e.g., March, *Advanced Organic Chemistry: Reactions, Mechanisms, and Structure*, 4$^{th}$ Ed., John Wiley & Sons, Inc. (1992), and Carey and Sundberg, *Advanced Organic Chemistry Part A: Structure and Mechanism*, 4th Ed., Plenum Press (2000), which are each incorporated by reference. Chemical starting materials and other reaction components useful in the synthesis of the nucleotides of the present invention are readily available from various commercial suppliers including, e.g., Sigma-Aldrich, Inc. (St Louis, Mo.).

V. Synthesis of Blocked Nucleic Acids Comprising 2'-Terminator Nucleosides

The synthesis of blocked oligonucleotides that include 2'-terminator nucleosides can be accomplished using various types of nucleic acid synthesis reagents. To illustrate, oligonucleotides may be synthesized enzymatically, e.g., using a nucleotide incorporating biocatalyst (e.g., a DNA polymerase, a ligase, etc.) or by chemical synthesis, e.g., using a phosphoramidite method or a phosphite-triester method (Herdewijn, *Oligonucleotide Synthesis: Methods and Applications*, Humana Press (2005), Gait (Ed.), *Oligonucleotide Synthesis*, Oxford University Press (1984), Vorbruggen et al., *Handbook of Nucleoside Synthesis*, John Wiley & Sons, Inc. (2001), and Hermanson, *Bioconjugate Techniques*, Elsevier Science (1996), which are each incorporated by reference). Labels can be introduced during enzymatic synthesis utilizing, e.g., labeled nucleoside triphosphate monomers (e.g., labeled extendible nucleotides, labeled 2'-terminator nucleotides, etc.), or introduced during chemical synthesis using labeled non-nucleotide or nucleotide phosphoramidites, or may be introduced subsequent to synthesis. The synthesis of 2'-terminator blocked oligonucleotides is also described in, e.g., Ser. No. 11/583,605, entitled "SYNTHESIS AND COMPOSITIONS OF NUCLEIC ACIDS COMPRISING 2'-TERMINATOR NUCLEOSIDES", filed Oct. 18, 2006 by Bodepudi et al., which is incorporated by reference. The synthesis of blocked oligonucleotides is also described further below in the examples.

An exemplary procedure for enzymatically synthesizing labeled oligonucleotides includes denaturing a template or target nucleic acid and annealing a pair of primers to the template. In some embodiments, a mixture of deoxynucleoside triphosphates (e.g., dGTP, dATP, dCTP, and dTTP) is added to the reaction mixture in which at least a fraction of one of the deoxynucleotides is labeled as described herein. Next, a nucleotide incorporating catalyst, such as a DNA polymerase enzyme is generally added to the reaction mixture under conditions in which the enzyme is active. A labeled oligonucleotide is formed by the incorporation of the labeled deoxynucleotides during polymerase strand synthesis. The DNA polymerase utilized in this method is generally thermostable, and the reaction temperature is typically cycled between denaturation and extension temperatures to effect the synthesis of labeled complementary strands of the target nucleic acid by PCR (Edwards et al. (Eds.), *Real-Time PCR: An Essential Guide*, Horizon Scientific Press (2004), Innis et al. (Eds.), *PCR Strategies*, Elsevier Science & Technology Books (1995), and Innis et al. (Eds.), *PCR Protocols*, Academic Press (1990), which are each incorporated by reference. Thereafter, the desired amplicon is separated from other components of the reaction mixture using various purification techniques known to persons of skill in the art. The amplicon can then be denatured and annealed to the template nucleic acid under conditions in which 2'-terminator nucleotides are incorporated at the 3' ends of the individual amplicon strands to produce the desired blocked oligonucleotides. Alternatively, oligonucleotides (synthesized enzymatically or chemically) comprising 2'-terminator nucleosides can be ligated to the amplicon strands to produce the desired blocked oligonucleotides. Other variations of these enzymatic approaches to blocked oligonucleotide synthesis will be apparent to persons of skill in the art.

Blocked oligonucleotides made using chemical synthesis are generally produced using a phosphoramidite method, although other approaches are also optionally utilized. Phosphoramidite-based synthesis is commonly performed with growing oligonucleotide chains attached to solid supports, so that excess reagents, which are in the liquid phase, can be easily removed by filtration. This eliminates the need for other purification steps between cycles.

To briefly describe an exemplary solid-phase oligonucleotide synthesis cycle that utilizes a phosphoramidite method, a solid support including a protected nucleotide monomer is typically initially treated with acid (e.g., trichloroacetic acid) to remove a 5'-hydroxyl protecting group, freeing the hydroxyl for a subsequent coupling reaction. An activated intermediate is then generally formed by simultaneously adding a protected phosphoramidite nucleoside monomer and a weak acid (e.g., tetrazole) to the reaction. The weak acid protonates the nitrogen of the phosphoramidite forming a reactive intermediate. Nucleoside addition to the growing nucleic acid chain is generally completed within 30 seconds. Thereafter, a capping step is typically performed to terminate any oligonucleotide chains that did not undergo nucleoside addition. Capping can be performed with, e.g., acetic anhydride, 1-methylimidazole, or the like. The internucleotide linkage is then converted from the phosphite to the more stable phosphotriester by oxidation using, e.g., iodine as an oxidizing agent and water as the oxygen donor. Following oxidation, the hydroxyl protecting group is typically removed with a protic acid (e.g., trichloroacetic acid or dichloroacetic acid) and the cycle is repeated until chain elongation is complete. After synthesis, the synthesized oligonucleotide is generally cleaved from the solid support using a base, such as ammonium hydroxide, or t-butyl amine. The cleavage reaction also removes any phosphate protecting groups (e.g., cyanoethyl). Finally, protecting groups on exocyclic amines of the bases and hydroxyl protecting groups on the labeling moiety or moieties are removed by treating the oligonucleotide solution under basic conditions at an elevated temperature (e.g., upto about 55° C.).

Descriptions of the chemistry used to form oligonucleotides by phosphoramidite methods are also provided in, e.g., U.S. Pat. No. 4,458,066, entitled "PROCESS FOR PREPARING POLYNUCLEOTIDES," issued Jul. 3, 1984 to Caruthers et al., and U.S. Pat. No. 4,415,732, entitled "PHOSPHORAMIDITE COMPOUNDS AND PROCESSES," issued Nov. 15, 1983 to Caruthers et al., which are both incorporated by reference.

Any of the phosphoramidite nucleoside monomers may be labeled as desired. In certain embodiments, if the 5'-terminus of the oligonucleotide is to be labeled, a labeled non-nucleotidic phosphoramidite may be used during the final condensation step. If an internal position of the oligonucleotide is to be labeled, a labeled nucleotidic phosphoramidite can be used during any of the condensation steps. In addition, following synthesis, oligonucleotides can also be labeled at essentially number of positions (Eckstein et al. (Eds.), *Oligonucleotides and Analogues: A Practical Approach*, Oxford University Press (1992), Chu et al. (1983) "Derivatization of unprotected polynucleotides," *Nucleic Acids Res.* 11(18): 6513-6529, and U.S. Pat. No. 5,118,800, entitled "Oligonucleotides possessing a primary amino group in the terminal nucleotide," issued Jun. 2, 1992 to Smith et al., which are each incorporated by reference). To further illustrate, oligonucleotides may also be labeled on their phosphodiester backbone (Eckstein et al. (1992), supra) or at the 3'-terminus (Nelson et al. (1992) "Oligonucleotide labeling methods. 3. Direct labeling of oligonucleotides employing a novel, non-nucleosidic, 2-aminobutyl-1,3-propanediol backbone," *Nucleic Acids Res.* 20(23):6253-6259, U.S. Pat. No. 5,401,837, entitled "Method for labeling the 3' terminus of a synthetic oligonucleotide using a unique multifunctional controlled pore glass (MF-CPG) reagent in solid phase oligonucleotide synthesis," issued Mar. 28, 1995 to Nelson, and U.S. Pat. No. 5,141,813, entitled "Multifunctional controlled pore glass reagent for solid phase oligonucleotide synthesis," issued Aug. 25, 1992 to Nelson, which are each incorporated by reference).

In certain embodiments, modified nucleotides are included in the blocked oligonucleotides described herein. To illustrate, the introduction of modified nucleotide substitutions into oligonucleotide sequences can, e.g., alter the melting temperature of the oligonucleotides as desired. In some embodiments, this can yield greater sensitivity relative to corresponding unmodified oligonucleotides even in the presence of one or more mismatches in sequence between the target nucleic acid and the particular oligonucleotide. Exemplary modified nucleotides that can be substituted or added in oligonucleotides include, e.g., C5-ethyl-dC, C5-methyl-dC, C5-ethyl-dU, 2,6-diaminopurines, C5-propynyl-dC, C7-propynyl-dA, C7-propynyl-dG, C5-propargylamino-dC, C5-propargylamino-dU, C7-propargylamino-dA, C7-propargylamino-dG, 7-deaza-2-deoxyxanthosine, pyrazolopyrimidine analogs, pseudo-dU, nitro pyrrole, nitro indole, 2'-0-methyl Ribo-U, 2'-0-methyl Ribo-C, an 8-aza-dA, an 8-aza-dG, a 7-deaza-dA, a 7-deaza-dG, N4-ethyl-dC, and N6-methyl-dA. To further illustrate, other examples of modified oligonucleotides include those having one or more LNA™ monomers. Nucleotide analogs such as these are also described in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbaek, D K). Additional oligonucleotide modifications are referred to herein, including in the definitions provided above.

The oligonucletides (e.g., primers, probes, etc.) utilized as described herein can be designed using essentially any approach know to persons of skill in the art. To illustrate, examples of techniques that are optionally adapted for use in designing oligonucletide are described in, e.g., Chen et al. (2003) "Primer Design Assistant (PDA): a web-based primer design tool" *Nucleic Acids Res.* 31(13):3751-3754, Miura et al. (2005) "A novel strategy to design highly specific PCR primers based on the stability and uniqueness of 3'-end subsequences" *Bioinformatics* 21(24):4363-4370, Hyyro et al. (2005) "Genome-wide selection of unique and valid oligonucleotides" *Nucleic Acids Res.* 33(13):e115, and Weckx et al. (2005) "SNPbox: a modular software package for large-scale primer design" *Bioinformatics* 21(3): 385-387, which are each incorporated by reference.

VI. Labeling

The oligonucleotides (e.g., primers, probes, etc.) described herein are optionally labeled, e.g., to facilitate subsequent detection. In some embodiments, the nucleic acid synthesis reagents (e.g., phosphoramidite precursors of 2'-terminator nucleotides, phosphoramidite precursors of other nucleotides, etc.) are labeled prior to synthesis of the oligonucleotides. For example, a label is optionally attached, e.g., to a homocyclic ring, a heterocyclic ring, or an aryl group of a 2'-terminator nucleotide or other nucleotide (e.g., via $C^5$ of a pyrimidine, $N^4$ of cytidine, $N^7$ of a purine, $N^6$ of adenosine, $C^8$ of a purine, or another attachment site known in the art), e.g., through an amide, ester, thioester, ether, thioether, carbon-carbon, or other type of covalent bond. In addition, or alternatively, the label is attached to a sugar moiety (e.g., a ribose sugar, etc.), or an analog thereof (e.g., a carbocyclic ring, etc.), of a 2'-terminator nucleotide or other nucleotide (e.g., a dNTP or the like), and/or a phosphate group of a 2'-terminator nucleotide or other nucleotide, such as by a covalent bond that is an amide, ester, thioester, ether, thioether, carbon-carbon, or other bond. Covalent bonds are typically formed in reactions between electrophilic and nucleophilic groups of labels and nucleotides. In certain embodiments, labels and nucleotides are directly conjugated to one another (e.g., via single, double, triple or aromatic carbon-carbon bonds, or via carbon-nitrogen bonds, nitrogen-nitrogen bonds, carbon-oxygen bonds, carbon-sulfur bonds, phosphorous-oxygen bonds, phosphorous-nitrogen bonds, etc.). Optionally, a linker attaches the label to a 2'-terminator nucleotide or other nucleotide. A wide variety of linkers can be used or adapted for use in conjugating labels and nucleotides. Certain non-limiting illustrations of such linkers are referred to herein.

Essentially any label is optionally utilized to label the nucleotides and nucleosides utilized in the oligonucletides described herein. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional details relating to fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg., USA), Amersham Biosciences Corp. (Piscataway, N.J., USA), Applied Biosystems (Foster City, Calif., USA), etc. Other labels include, e.g., biotin, weakly fluorescent labels (Yin et al. (2003) *Appl Environ Microbiol.* 69(7): 3938, Babendure et al. (2003) *Anal. Biochem.* 317(1): 1, and Jankowiak et al. (2003) *Chem Res Toxicol.* 16(3):304), non-fluorescent labels, calorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6): 1725), non-fluorescent donor moieties (as described in, e.g., U.S. Provisional Patent Application No. 60/724,202, entitled "NON-FLUORESCENT ENERGY TRANSFER," filed Oct. 5, 2005 by Will et al.), and an alpha-methyl-PEG labeling reagent (as described in, e.g., U.S. patent application Ser. No. 10/719,257, entitled "DETECTABLE LABELED NUCLEOSIDE ANALOGS AND METHODS OF USE THEREOF" filed Nov. 21, 2003 by Bodepudi et al.), which references are each incorporated by reference.

In certain embodiments, the label comprises a radioisotope, such as $^3$H, $^{14}$C, $^{22}$Na, $^{32}$P, $^{33}$P, $^{35}$s, $^{42}$K, $^{45}$Ca, $^{59}$Fe, $^{125}$I, $^{203}$Hg, or the like. To further exemplify, the label also optionally includes at least one mass-modifying group. For example, the mass-modifying group is optionally selected from, e.g., deuterium, F, Cl, Br, I, S, $N_3$, XY, $CH_3$, $SPO_4$, $BH_3$, $SiY_3$, $Si(CH_3)_3$, $Si(CH_3)_2(C_2H_5)$, $Si(CH_3)(C_2H_5)_2$, $Si(C_2H_5)_3$, $(CH_2)_nNY_2$, $CH_2CONY_2$, $(CH_2)_nOH$, $CH_2F$, $CHF_2$, $CF_3$, and a phosphorothioate group, where X is O, NH, NY, S, NHC(S), OCO(CH)$_n$COO, NHCO(CH$_2$)$_n$COO, OSO$_2$O, OCO(CH$_2$)$_n$, NHC(S)NH, OCO(CH$_2$)$_n$S, OCO(CH$_2$)S, NC$_4$O$_2$H$_2$S, OPO(O-alkyl), or OP(O-alkyl); n is an integer from 1 to 20 inclusive; and, Y is H, deuterium, an alkyl group, an alkoxy group, an aryl group, a polyoxymethylene group, a monoalkylated polyoxymethylene group, a polyethylene imine group, a polyamide group, a polyester group, a alkylated silyl group, a heterooligo, a polyaminoacid, a heterooligo/polyaminoacid group, or a polyethylene glycol group. Additional details relating to nucleic acid labeling and sequence analysis are provided in, e.g., Sterky et al. (2000) "Sequence analysis of genes and genomes," *J. Biotech.* 76(2000): 1, Sensen (Ed.) *Biotechnology, Volume 5B, Genomics and Bioinformatics*, John Wiley & Sons, Inc. (2001), and Sensen (Ed.) *Essentials of Genomics and Bioinformatics*, John Wiley & Sons, Inc. (2002), which are each incorporated by reference.

A large variety of linkers are available for linking labels to nucleic acids and will be apparent to one of skill in the art. A linker is generally of a structure that is sterically and electronically suitable for incorporation into a nucleic acid. Linkers optionally include, e.g., ether, thioether, carboxamide, sulfonamide, urea, urethane, hydrazine, or other moieties. To further illustrate, linkers generally include between about one and about 25 nonhydrogen atoms selected from, e.g., C, N, O, P, Si, S, etc., and comprise essentially any combination of, e.g., ether, thioether, amine, ester, carboxamide, sulfonamide, hydrazide bonds and aromatic or heteroaromatic bonds. In some embodiments, for example, a linker comprises a combination of single carbon-carbon bonds and carboxamide or thioether bonds. Although longer linear segments of linkers are optionally utilized, the longest linear segment typically contains between about three to about 15 nonhydrogen atoms, including one or more heteroatoms.

Nonlimiting examples of linker moieties include substituted (e.g., functionalized) or unsubstituted groups, such as imidazole/biotin linkers, polymethylene groups, arylene groups, alkylarylene groups, arylenealkyl groups, arylthio groups, amido alkyl groups, alkynyl alkyl groups, alkenyl alkyl groups, alkyl groups, alkoxyl groups, thio groups, amino alkyl groups, morpholine derivatized phosphates, peptide nucleic acids (e.g., N-(2-aminoethyl)glycine, etc.), and the like. Certain of these and other linkers are described further in, e.g., U.S. Pat. No. 6,339,392 to Haugland et al., U.S. Pat. No. 5,047,519 to Hobbs, Jr. et al., U.S. Pat. No. 4,711,958 to Iizuka et al., U.S. Pat. No. 5,175,269 to Stavrianopoulos, U.S. Pat. No. 4,711,955 to Ward et al., U.S. Pat. No. 5,241,060 to Engelhardt et al., U.S. Pat. No. 5,328,824 to Ward et al., and U.S. Pat. Publication No. 2002/0151711 by Khan et al., which are each incorporated by reference. Additional details relating to nucleic acid labeling and linkers are provided in, e.g., Hermanson, *Bioconjugate Techniques*, Elsevier Science (1996), which is incorporated by reference. In certain embodiments, suitable linkers comprise photocleavable moieties, such as 2-nitrobenzyl moieties, alpha-substituted 2-nitrobenzyl moieties (e.g., 1-(2-nitrophenyl) ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Photocleavable linkers are described further in, e.g., U.S. Pat. Publication No. 2003/0099972 by Olejnik et al., which is incorporated by reference. In some embodiments, linkers include metals, such as platinum atoms. These are described further in, e.g., U.S. Pat. No. 5,714,327 to Houthoff et al., which is incorporated by reference. A number of linkers of varying lengths are commercially available from various suppliers including, e.g., Qiagen-Operon Technologies, Inc. (Alameda, Calif., USA), BD Biosciences Clontech (Palo Alto, Calif., USA), and Molecular BioSciences (Boulder, Colo., USA).

VII. Reaction Mixtures

The invention also provides many different reaction mixtures that can be used in a wide variety of applications, particularly where it is desirable to remove 2'-terminator nucleotides from nucleic acids, polymerize nucleotides, and/or amplify nucleic acids. In some embodiments, for example, reaction mixtures are utilized in performing homogeneous amplification/detection assays (e.g., real-time PCR monitoring), or detecting mutations or genotyping nucleic acids. In certain embodiments, multiple primers and/or probes are pooled together in reaction mixtures for use in applications that involve multiplex formats. Many of these applications are described further below or are otherwise referred to herein.

In addition to the blocked oligonucleotides described herein, reaction mixtures also generally include various reagents that are useful in performing, e.g., 2'-nucleotide removal from these oligonucleotides (e.g., to produce activated or extendible oligonucleotides), nucleotide polymerization, nucleic acid amplification and detection reactions (e.g., real-time PCR monitoring or 5'-nuclease assays), and the like. Exemplary types of these other reagents include, e.g., template or target nucleic acids (e.g., obtained or derived from essentially any source), pyrophosphate, light emission modifiers, biocatalysts (e.g., DNA polymerases, etc.), buffers, salts, amplicons, glycerol, metal ions (e.g., Mg$^{+2}$, etc.), dimethyl sulfoxide (DMSO), poly rA (e.g., as a carrier nucleic acid for low copy number targets), uracil N-glycosylase (UNG) (e.g., to protect against carry-over contamination). In some kinetic PCR-related applications, reaction mixtures also include probes that facilitate the detection of amplification products. Examples of probes used in these processes include, e.g., hybridization probes, 5'-nuclease probes, and/or hairpin probes. Nucleic acid amplification and detection as well as other methods are also described further below.

As referred to herein, in certain embodiments, various light emission modifiers are used in the reaction mixtures of the invention. Typically, light emission modifiers are soluble nucleic acid binding compounds that are capable of modifying the emission of light from labeled oligonucleotides, such as primers, 5'-nuclease probes, hybridization probes, hairpin probes, or the like to, e.g., reduce baseline or residual emissions of light from these labeled nucleic acids, among other applications. In some embodiments, for example, these light emission modifiers include various diazine and thiazine dyes. Exemplary diazine dyes that can be used as light emission modifiers include, e.g., azocarmine dyes (e.g., azocarmine A, azocarmine B (C$_{28}$H$_{17}$N$_3$O$_9$S$_3$Na$_2$), azocarmine G (C$_{28}$H$_{18}$N$_3$O$_6$S$_2$Na), etc.), phenazine dyes, oxazine dyes (e.g., Celestine blue (C$_{17}$H$_{18}$ClN$_3$O$_4$), etc.), diethylsafraninazodimethylaniline chloride (i.e., Janus Green B or Diazine Green 5 (C$_{30}$H$_{31}$N$_6$Cl)), and the like. To further illustrate, exemplary thiazine dyes that can be used as light emission modifiers include, e.g., methylene blue (C$_{16}$H$_{18}$ClN$_3$S), methylene green (C$_{16}$H$_{17}$ClN$_4$O$_2$S), thionin (C$_{12}$H$_{10}$ClN$_3$S), sym-dimethylthionin, toluidine blue O (C$_{15}$H$_{16}$N$_3$SCl), new methylene blue (C$_{18}$H$_{22}$ClN$_3$S), methylene violet bernthsen, azure A (C$_{14}$H$_{14}$ClN$_3$S), azure B (C$_{15}$H$_{16}$ClN$_3$S), azure C (C$_{13}$H$_{12}$ClN$_3$S), and the like. Light emission modifiers are also described in, e.g., U.S. patent application Ser. No. 11/474,062, entitled "LIGHT EMISSION MODIFIERS AND THEIR USES IN NUCLEIC ACID DETECTION, AMPLIFICATION AND ANALYSIS," filed Jun. 23, 2006 by Gupta et al., which is incorporated by reference.

Reaction mixtures are generally produced by combining selected nucleotides, primers, and/or probes, as described above, with quantities of the other reagents that are sufficient for performing the particular application that is selected. The quantities of reagents to be included in a given reaction mixture will be apparent to persons of skill in the art in view of the selected method to be performed. To illustrate, however, primer nucleic acids and extendible nucleotides (e.g., four dNTPs (dGTP, dCTP, dATP, dTTP)) are each typically present in a large molar excess in these reaction mixtures. In addition, any of the four extendible NTPs may be utilized with certain enzymes described herein Suitable extendible and/or terminator nucleotides are readily available from many different commercial suppliers including, e.g., Roche Diagnostics Corporation (Indianapolis, Ind., USA), Amersham Biosciences Corp. (Piscataway, N.J., USA), and Applied Biosystems (Foster City, Calif., USA).

The blocked oligonucleotides described herein are typically non-extendible by at least one biocatalyst selected from, e.g., a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZO5R polymerase (where R refers to a E678G mutation), a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* specie SPS-17 polymerase, a E615G Taq polymerase, a *Thermus* ZO5R polymerase (where R refers to a E678G mutation), a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, an RNA polymerase, a *E. coli* RNA polymerase, an SP6 RNA polymerase, a T3 RNA polymerase, a T4 DNA polymerase, a T7 RNA polymerase, an RNA polymerase II, a terminal transferase, a polynucleotide phosphorylase, a ribonucleotide incorporating DNA polymerase, and the like. Moreover, many of these biocatalysts include pyrophophorolysis activity and accordingly, can catalyze the removal of nucleotides from nucleic acids (e.g., 2'-terminator nucleotides from blocked oligonucleotides in certain embodiments). The sequences of certain of these biocatalysts are publicly available from various sources including, e.g., GenBank® and the like.

As indicated above, in some embodiments, the enzyme is modified. Exemplary modified enzymes include, e.g., a G46E E678G CS5 DNA polymerase, a G46E L329A E678G CS5 DNA polymerase, a G46E L329A D640G S671F CS5 DNA polymerase, a G46E L329A D640G S67 IF E678G CS5 DNA polymerase, a G46E E678G CS6 DNA polymerase, an E615G Taq DNA polymerase, and the like. These modified enzymes typically comprise mutations that enhance that incorporation of ribonucleotides, that enhance incorporation of 2'-modified analogs of ribonucleotides (e.g., 2'-terminator nucleotides), and/or that reduce or eliminate 5'-3' exonuclease activity, e.g., relative to an enzyme that lacks one or more of these mutations. Additional details relating to useful biocatalysts are also provided in, e.g., Ser. No. 60/852,882, entitled "MUTANT DNA POLYMERASES AND RELATED METHODS", filed Oct. 18, 2006 by Bauer et al., U.S. Pat. No. 5,939,292, entitled "THERMOSTABLE DNA POLYMERASES HAVING REDUCED DISCRIMINATION AGAINST RIBO-NTPS," which issued Aug. 17, 1999 to Gelfand et al., U.S. Pat. No. 4,889,818, entitled "PURIFIED THERMOSTABLE ENZYME," which issued Dec. 26, 1989 to Gelfand et al., U.S. Pat. No. 5,374,553, entitled "DNA ENCODING A THERMOSTABLE NUCLEIC ACID POLYMERASE ENZYME FROM THERMOTOGA MARITIMA," which issued Dec. 20, 1994 to Gelfand et al., U.S. Pat. No. 5,420,029, entitled "MUTATED THERMOSTABLE NUCLEIC ACID POLYMERASE ENZYME FROM THERMOTOGA MARITIMA," which issued May 30, 1995 to Gelfand et al., U.S. Pat. No. 5,455,170, entitled "MUTATED THERMOSTABLE NUCLEIC ACID POLYMERASE ENZYME FROM *THERMUS* SPECIES Z05," which issued Oct. 3, 1995 to Abramson et al., U.S. Pat. No. 5,466,591, entitled "5' TO 3' EXONUCLEASE MUTATIONS OF THERMOSTABLE DNA POLYMERASES," which issued Nov. 14, 1995 to Abramson et al., U.S. Pat. No. 5,618,711, entitled "RECOMBINANT EXPRESSION VECTORS AND PURIFICATION METHODS FOR *THERMUS THERMOPHILUS* DNA POLYMERASE," which issued Apr. 8, 1997 to Gelfand et al., U.S. Pat. No. 5,624,833, entitled "PURIFIED THERMOSTABLE NUCLEIC ACID POLYMERASE ENZYME FROM THERMOTOGA MARITIMA," which issued Apr. 29, 1997 to Gelfand et al., U.S. Pat. No. 5,674,738, entitled "DNA ENCODING THERMOSTABLE NUCLEIC ACID POLYMERASE ENZYME FROM *THERMUS* SPECIES Z05," which issued Oct. 7, 1997 to Abramson et al., U.S. Pat. No. 5,789,224, entitled "RECOMBINANT EXPRESSION VECTORS AND PURIFICATION METHODS FOR *THERMUS THERMOPHILUS* DNA POLYMERASE," which issued Aug. 4, 1998 to Gelfand et al., U.S. Pat. No. 5,795,762, entitled "5' TO 3' EXONUCLEASE MUTATIONS OF THERMOSTABLE DNA POLYMERASES," which issued Aug. 18, 1998 to Abramson et al., U.S. Pat. Application Publication No. US 2002/0012970, entitled "HIGH TEMPERATURE REVERSE TRANSCRIPTION USING MUTANT DNA POLYMERASES," which published Jan. 31, 2002 by Smith et al., U.S. Pat. Application Publication No. US 2004/0005599, entitled "THERMOSTABLE OR THERMOACTIVE DNA POLYMERASE MOLECULES WITH ATTENUATED 3'-5' EXONUCLEASE ACTIVITY", which published Jan. 8, 2004 by Schoenbrunner et al., and U.S. patent application Ser. No. 10/401,403, filed Mar. 26, 2003, which are each incorporated by reference.

The production of modified enzymes with, e.g., enhanced efficiency for incorporating 2'-terminator nucleotides or other desired properties may be accomplished by various processes including, e.g., site-directed mutagenesis, chemical modification, etc. More specifically, site-directed mutagenesis is generally accomplished by site-specific primer-directed mutagenesis. This technique is typically conducted using a synthetic oligonucleotide primer complementary to a single-stranded phage DNA to be mutagenized except for a limited mismatch representing the desired mutation. Briefly, the synthetic oligonucleotide is used as a primer to direct synthesis of a strand complementary to the plasmid or phage, and the resulting double-stranded DNA is transformed into a phage-supporting host bacterium. The resulting bacteria can be assayed by, for example, DNA sequence analysis or probe hybridization to identify those plaques carrying the desired mutated gene sequence. To further illustrate, many other approaches to modify nucleic acids, such as "recombinant PCR" methods can also be utilized.

In practicing aspects of the present invention (e.g., producing modified enzymes, performing amplification reactions, etc.), many conventional techniques in molecular biology and recombinant DNA are optionally utilized. These techniques are well known and are explained in, for example, *Current Protocols in Molecular Biology*, Volumes I, II, and III, 1997 (F. M. Ausubel ed.); Sambrook et al., 2001, *Molecular Cloning: A Laboratory Manual*, Third Edition, Cold Spring Harbor Laboratory Press, Cold Spring Harbor, N.Y.; Berger and Kimmel, *Guide to Molecular Cloning Techniques, Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis,* 1984 (M. L. Gait ed.); *Nucleic Acid Hybridization,* 1985, (Hames and Higgins); *Transcription and Translation,* 1984 (Hames and Higgins eds.); *Animal Cell Culture,* 1986 (R. I. Freshney ed.); *Immobilized Cells and Enzymes,* 1986 (IRL Press); Perbal, 1984, *A Practical Guide to Molecular Cloning*; the series, *Methods in Enzymology* (Academic Press, Inc.); *Gene Transfer Vectors for Mammalian Cells,* 1987 (J. H. Miller and M. P. Calos eds., Cold Spring Harbor Laboratory); and *Methods in Enzymology* Vol. 154 and Vol. 155 (Wu and Grossman, and Wu, eds., respectively), which are each incorporated by reference.

VIII. Pap-Related Methods

The invention also provides methods of using the blocked oligonucleotides described herein. In some embodiments, for example, these oligonucleotides are used to perform assays that involve the detection of target nucleic acids, e.g., to provide diagnostic, genetic, or other information about subjects from which these targets were derived. These aspects are also illustrated in the examples provided below.

The oligonucleotides described herein are optionally used or adapted for use in essentially any application that involves the removal of 2'-terminator nucleotides from these nucleic acids, e.g., via the process of pyrophosphorolysis. Examples of nucleic acid-related types of applications, include the analysis of the structure and conformation of nucleic acids, real-time PCR assays, and SNP detection (Myakishev et al. (2001) "High-throughput SNP genotyping by allele-specific PCR with universal energy-transfer-labeled primers," *Genome Res* 11:163-169, Lee et al. (1999) "Seven-color, homogeneous detection of six PCR products," *Biotechniques* 27:342-349, Thelwell et al. (2000) "Mode of action and application of Scorpion primers to mutation detection," *Nucleic Acids Res* 28:3752-3761, Whitcombe et al. (1999) "Detection of PCR products using self-probing amplicons and fluorescence," *Nat Biotechnol* 17:804-807, Heid et al. (1996) "Real time quantitative PCR," *Genome Res* 6:986-994, Nazarenko et al. (1997) "A closed tube format for amplification and detection of DNA based on energy transfer," *Nucleic Acids Res* 25:2516-2521, which are each incorporated by reference); detection of nucleic acid hybridization (Parkhurst et al. (1995) "Kinetic studies by fluorescence resonance energy transfer employing a double-labeled oligonucleotide: hybridization to the oligonucleotide complement and to single-stranded DNA," *Biochemistry* 34:285-292, Tyagi et al. (1996) "Molecular beacons: probes that fluoresce upon hybridization," *Nat Biotechnol* 14:303-308, Tyagi et al. (1998) "Multicolor molecular beacons for allele discrimination," *Nat Biotechnol* 16:49-53, Sixou et al. (1994) "Intracellular oligonucleotide hybridization detected by fluorescence resonance energy transfer (FRET)," *Nucleic Acids Res* 22:662-668, and Cardullo et al. (1988) "Detection of nucleic acid hybridization by nonradiative fluorescence resonance energy transfer," *Proc Natl Acad Sci USA* 85:8790-8794, which are each incorporated by reference); primer-extension assays for detecting mutations (Chen et al. (1997) "Fluorescence energy transfer detection as a homogeneous DNA diagnostic method," *Proc Natl Acad Sci USA* 94:10756-10761, which is incorporated by reference); and automated DNA sequencing (Woolley et al. (1995) "Ultra-high-speed DNA sequencing using capillary electrophoresis chips," *Anal Chem* 67:3676-3680, Hung et al. (1998) "Comparison of fluorescence energy transfer primers with different donor-acceptor dye combinations," *Anal Biochem* 255:32-38, and Ju et al. (1995) "Fluorescence energy transfer dye-labeled primers for DNA sequencing and analysis," *Proc Natl Acad Sci USA* 92:4347-4351, which are each incorporated by reference). Aspects relating to PAP, which can be adapted for use with the oligonucleotides described herein, are also described in, e.g., U.S. Pat. No. 7,033,763, entitled "PYROPHOSPHOROLYSIS ACTIVATED POLYMERIZATION (PAP)" issued Apr. 25, 2006 to Liu et al., U.S. Pat. No. 6,534,269, entitled "PYROPHOSPHOROLYSIS ACTIVATED POLYMERIZATION (PAP): APPLICATION TO ALLELE-SPECIFIC AMPLIFICATION AND NUCLEIC ACID SEQUENCE DETERMINATION" issued Mar. 18, 2003 to Liu et al., U.S. patent application Ser. No. 10/798,844, entitled "PYROPHOSPHOROLYSIS ACTIVATED POLYMERIZATION (PAP)" filed Mar. 12, 2004 by Liu et al., which are each incorporated by reference.

To further illustrate, examples of general types of nucleic acid analysis technologies that can be used or adapted for use to analyze target nucleic acids in or from, e.g., the reactions mixtures of the invention include various nucleic acid amplification assays. A common characteristic among nucleic acid amplification assays is that they are typically designed to amplify nucleic acid sequences that are specific for the organism being detected. Nucleic acid amplification tests generally have greater sensitivity than other approaches to nucleic acid analysis. This sensitivity, which is further improved with the use of the oligonucleotides described herein, is typically attributable to their ability to produce a positive signal from as little as a single copy of the target nucleic acid. Amplification methods that are optionally utilized or adapted to detect target nucleic acids include, e.g., various polymerase, ligase, or reverse-transcriptase mediated amplification methods, such as the polymerase chain reaction (PCR), the ligase chain reaction (LCR), and/or the reverse-transcription PCR (RT-PCR). Additional details regarding the use of these and other amplification methods and various approaches to sample preparation for these assays can be found in any of a variety of standard texts, including, e.g., Berger, Sambrook, Ausubel 1 and 2, and Innis, which are referred to above.

Various commercial nucleic acid amplification assays that are optionally adapted for use with the reagents and methods of the invention generally differ in their amplification methods and their target nucleic acid sequences. Examples of these commercial tests include hybridization probe assays (e.g., using the LightCycler® system) and the AMPLICOR® and COBAS AMPLICOR® assays (Roche Diagnostics Corporation, Indianapolis, Ind., USA), which use polymerase chain reactions (PCR); the LCx® test (Abbott Laboratories, Abbott Park, Ill., USA), which uses ligase chain reactions (LCR); the BDProbeTec™ ET test (Becton, Dickinson and Company, Franklin Lakes, N.J., USA), which uses strand displacement amplification (SDA); and the APTIMA™ assay (Gen-Probe, Inc., San Diego, Calif., USA), which uses transcription-mediated amplification (TMA). Nucleic acid amplification and detection is described further below.

In certain embodiments, for example, 5'-nuclease probes are utilized in various 5'-nuclease reactions. Many 5'-nuclease assays are well known to those of skill in the art. Examples of such reactions are also described in, e.g., U.S. Pat. No. 6,214,979, entitled "HOMOGENEOUS ASSAY SYSTEM," issued Apr. 10, 2001 to Gelfand et al., U.S. Pat.

No. 5,804,375, entitled "REACTION MIXTURES FOR DETECTION OF TARGET NUCLEIC ACIDS," issued Sep. 8, 1998 to Gelfand et al., U.S. Pat. No. 5,487,972, entitled "NUCLEIC ACID DETECTION BY THE 5'-3' EXONUCLEASE ACTIVITY OF POLYMERASES ACTING ON ADJACENTLY HYBRIDIZED OLIGONUCLEOTIDES," issued Jan. 30, 1996 to Gelfand et al., and U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., which are each incorporated by reference.

To briefly illustrate, in a 5'-nuclease reaction, a target nucleic acid is contacted with a primer and a probe (e.g., a 5'-nuclease probe) under conditions in which the primer and probe hybridize to a strand of the target nucleic acid. The target nucleic acid, primer and probe are also contacted with a nucleic acid polymerase having 5' to 3' nuclease activity. Nucleic acid polymerases possessing 5' to 3' nuclease activity can cleave the probe hybridized to the target nucleic acid downstream of the primer. The 3' end of the primer provides the initial binding site for the polymerase. The bound polymerase cleaves fragments from the probe upon encountering the 5' end of the probe.

The primer and probe can be designed so that they anneal in close proximity on the target nucleic acid such that binding of the nucleic acid polymerase to the 3' end of the primer puts it in contact with the 5' end of the probe in the absence of primer extension. The term "polymerization-independent cleavage" refers to this process. Alternatively, if the primer and probe anneal to more distantly spaced regions of the target nucleic acid, polymerization typically occurs before the nucleic acid polymerase encounters the 5' end of the probe. As the polymerization continues, the polymerase progressively cleaves fragments from the 5' end of the probe. This cleavage continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. Provided the primer and probe are adjacently bound to the nucleic acid, sequential rounds of probe annealing and cleavage of fragments can occur. Thus, a sufficient amount of fragments can be generated, making detection possible in the absence of polymerization.

In either process, a sample is provided which is thought to contain the target nucleic acid. The target nucleic acid contained in the sample may be first reverse transcribed into cDNA, if necessary, and then denatured, using any suitable denaturing method, including physical, chemical, or enzymatic methods, which are known to those of skill in the art. An exemplary physical approach to effect strand separation involves heating the nucleic acid until it is completely (>99%) denatured. Typical heat denaturation involves temperatures ranging from about 85° C. to about 105° C. (typically from about 85° C. to about 98° C., and more typically from about 85° C. to about 95° C.), for periods of time ranging from about 1 second to about 10 minutes (e.g., from few seconds to about 1 minute). As an alternative to denaturation, the nucleic acid may exist in a single-stranded form in the sample, such as when the sample comprises single-stranded RNA or DNA viruses.

The denatured target nucleic acid strand is typically incubated with a primer and a probe under hybridization conditions that permit the primer and probe to bind to the target nucleic acid strand. In some embodiments, two primers can be used to amplify the target nucleic acid. The two primers are typically selected so that their relative positions along the target nucleic acid are such that an extension product synthesized from one primer, when the extension product is separated from its template (complement), serves as a template for the extension of the other primer to yield a replicate strand of defined length.

Because the complementary strands are typically longer than either the probe or primer, the strands have more points of contact and thus a greater chance of binding to each other over a given period of time. Accordingly, a high molar excess of probe and primer is typically utilized to favor primer and probe annealing over template strand reannealing. In multiplexing formats, multiple probes are typically used in a single reaction vessel to simultaneously detect multiple target nucleic acids.

Primers are generally of sufficient length and complementarity so that they selectively bind to target nucleic acids under selected conditions to permit polymerization-independent cleavage or polymerization-dependent cleavage to proceed. The exact length and composition of the primer will depend on many factors, including temperature of the annealing reaction, source and composition of the primer, proximity of the probe annealing site to the primer annealing site, and ratio of primer:probe concentration. For example, depending on the complexity of the target sequence, the primer typically includes about 15-30 nucleotides, although it may contain more or fewer nucleotides.

The probe is generally annealed to its complementary target nucleic acid before the nucleic acid polymerase encounters that region of the target nucleic acid, thereby permitting the 5' to 3' nuclease activity of the enzyme to cleave fragments from the probe. To enhance the likelihood that the probe will anneal to the target nucleic acid before the polymerase reaches this region of hybridization, a variety of techniques may be utilized. For example, short primers generally require cooler temperatures to form sufficiently stable hybrid complexes with the nucleic acid. Therefore, the probe can be designed to be longer than the primer so that the probe preferentially anneals to the target nucleic acid at higher temperatures relative to primer annealing. To further illustrate, the nucleotide composition of the probe can be chosen to have greater G/C content and, consequently, greater thermal stability than the primer. Optionally, modified nucleotides may be incorporated into primers or probes to effect either greater or lesser thermal stability in comparison to primers or probes having only unmodified nucleotides. Exemplary modified nucleotides are described further above. The thermocycling parameters can also be varied to take advantage of the differential thermal stability of the probe and primer. For example, following a thermocycling denaturation step, an intermediate temperature may be introduced which permits probe binding, but not primer binding. Thereafter, the temperature can be further reduced to permit primer annealing. To preferentially favor binding of the probe before the primer, a high molar excess of probe to primer concentration can also be used. Such probe concentrations are typically in the range of about 2 to about 20 times higher than the respective primer concentration, which is generally about $0.5\text{-}5 \times 10^{-7}$ M.

Template-dependent extension of primers is generally catalyzed by a biocatalyst (e.g., a polymerase) in the presence of adequate amounts of the four deoxyribonucleoside triphosphates (DATP, dGTP, dCTP, and dTTP) or analogs in a reaction mixture that also includes appropriate salts, metal cations, and buffers. Reaction mixtures are described further above. Suitable biocatalysts are enzymes known to catalyze primer and template-dependent DNA synthesis and possess the 5' to 3' nuclease activity. Exemplary DNA polymerases of this type include *E. coli* DNA polymerase I, Tth DNA polymerase, *Bacillus stearothermophilus* DNA polymerase, Taq DNA polymerase, *Thermus* sp. ZO5 DNA polymerase, *Thermatoga maritima* DNA polymerase, *Thermatoga neopolitana* DNA polymerase, and *Thermosipho africanus* DNA polymerase as well as others referred to herein or otherwise known to those of skill in the art. The reaction conditions for catalyzing DNA synthesis with these DNA polymerases are well known in the art. Typically, the biocatalyst efficiently cleaves the probe and releases labeled fragments so that a detectable signal is directly or indirectly generated.

The products of the synthesis are generally duplex molecules that include the template strands and the primer extension strands. Byproducts of this synthesis are probe fragments, which can include a mixture of mono-, di- and larger nucleotide fragments. Repeated cycles of denaturation, probe and primer annealing, and primer extension and probe cleavage result in the exponential accumulation of the region defined by the primers and the exponential generation of labeled fragments. Sufficient cycles are run to achieve a detectable amount of probe fragments, which is generally several orders of magnitude greater than background signal.

In certain embodiments, PCR reactions are carried out as an automated process, which utilizes a thermostable enzyme. In this process the reaction mixture is cycled through a denaturing step, a probe and primer annealing step, and a synthesis step in which cleavage and displacement occur concurrently with primer dependent template extension. In some embodiments, the methods described herein are performed using a system. Such systems are described in greater detail below. Optionally, thermal cyclers, such as those commercially available from, e.g., Applied Biosystems (Foster City, Calif., USA), which are designed for use with thermostable enzymes, may be utilized.

Thermostable polymerases are typically used in automated processes that effect the denaturation of double stranded extension products by exposing them to elevated temperatures (e.g., about 95° C.) during the PCR cycle. For example, U.S. Pat. No. 4,889,818, entitled "PURIFIED THERMOSTABLE ENZYME," issued to Dec. 26, 1989 to Gelfand et al., which is incorporated by reference, discloses a representative thermostable enzyme isolated from *Thermus aquaticus*. Additional representative thermostable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermatoga neopolitana, Thermosipho africanus, Thermococcus littoralis,* and *Methanothermus fervidus*.

Hybridization of probes to target nucleic acids can be accomplished by choosing appropriate hybridization conditions. The stability of the probe:target nucleic acid hybrid is typically selected to be compatible with the assay and washing conditions so that stable, detectable hybrids form only between the probes and target nucleic acids. Manipulation of one or more of the different assay parameters determines the exact sensitivity and specificity of a particular hybridization assay.

More specifically, hybridization between complementary bases of nucleic acids (e.g., DNA, RNA, PNA, or combinations thereof), occurs under a wide variety of conditions that vary in temperature, salt concentration, electrostatic strength, and buffer composition. Examples of these conditions and methods for applying them are described in, e.g., Tijssen, *Hybridization with Nucleic Acid Probes*, Vol. 24, Elsevier Science (1993), and Hames and Higgins, supra, which are both incorporated by reference. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. Hybridization between nucleic acids may be facilitated using buffers such as Tris-EDTA (TE), Tris-HCl and HEPES, salt solutions (e.g. NaCl, KCl, $MgCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin.

Essentially any available method for detecting target nucleic acids can be used in the present invention. Common approaches include real-time amplification detection with 5'-nuclease probes, hybridization probes, or hairpin probes (e.g., molecular beacons), detection of labels incorporated into the amplification primers or the amplified nucleic acids themselves, e.g., following electrophoretic separation of the amplification products from unincorporated labels, hybridization based assays (e.g., array based assays), and/or detection of secondary reagents that bind to the nucleic acids. These general approaches are also described in, e.g., Sambrook, and Ausubel 1 and 2, supra.

Hairpins probes, such as molecular beacons, are oligonucleotides designed for real-time detection and quantification of target nucleic acids. The 5' and 3' termini of hairpin probes generally comprise the labeling moieties, which confer the detectable properties of the probe. In an exemplary embodiment, one of the termini is attached to a reporter moiety (e.g., a fluorescent dye) and the other terminus is attached to a quencher moiety capable of quenching fluorescent emissions from the reporter moiety. When the hairpin probe is present free in solution, i.e., not hybridized to a second nucleic acid, the stem of the probe is stabilized by complementary base pairing. This self-complementary pairing results in a "hairpin loop" structure for the probe in which the reporter and quencher moieties are proximal to one another. In this confirmation, the quencher moiety quenches the reporter moiety. The loop of a hairpin probe typically comprises a sequence that is complementary to the sequence to be detected in the target nucleic acid, such that hybridization of the loop to its complementary sequence in the target forces disassociation of the stem, thereby distancing the reporter and quencher moieties from each other. This unquenches the reporter moiety, causing an increase in fluorescence from the hairpin probe.

Details regarding standard methods of making and using hairpin probes are generally known to persons of skill in the art and are also described in, e.g., Leone et al. (1995) "Molecular beacon probes combined with amplification by NASBA enable homogenous real-time detection of RNA," *Nucleic Acids Res.* 26:2150-2155, Kostrikis et al. (1998) "Molecular beacons: spectral genotyping of human alleles" *Science* 279:1228-1229, Fang et al. (1999) "Designing a novel molecular beacon for surface-immobilized DNA hybridization studies" *J. Am. Chem. Soc.* 121:2921-2922, and Marras et al. (1999) "Multiplex detection of single-nucleotide variation using molecular beacons" *Genet. Anal. Biomol.*

Eng. 14:151-156, which are each incorporated by reference. A variety of commercial suppliers produce standard and custom hairpin probes that can be adapted for use in the methods described herein, including Oswel Research Products Ltd. (UK), Research Genetics (a division of Invitrogen, Huntsville, Ala., USA), and the Midland Certified Reagent Company (Midland, Tex., USA). A variety of kits that utilize hairpin probes are also commercially available, such as the Sentinel™ Molecular Beacon Allelic Discrimination Kits from Stratagene (La Jolla, Calif., USA) and various kits from Eurogentec SA (Belgium) and Isogen Bioscience BV (Netherlands). These kits are also optionally adapted for use in the methods described herein.

Hybridization probes generally function in pairs and can be used to effect various types of real-time target nucleic acid detection, including quantification, mutation detection, melting temperature ($T_m$) multiplexing, and color multiplexing. Aspects of certain hybridization probe assays are also described in, e.g., Brega et al. (2004) "Real-time PCR for dihydrofolate reductase gene single-nucleotide polymorphisms in *Plasmodium vivax* isolates," *Antimicrob Agents Chemother.* 48(7):2581-2587, Perelle et al. (2004) "A LightCycler real-time PCR hybridization probe assay for detecting food-borne thermophilic Campylobacter," *Mol Cell Probes.* 18(5):321-327, and Whiley et al. (2003) "Detection of *Neisseria Meningitidis* in clinical samples by a duplex real-time PCR targeting the porA and ctrA genes," *Mol Diagn.* 7(3-4): 141-145, which are each incorporated by reference.

Hybridization probe assays typically include hybridizing a pair of labeled probes with a target or template nucleic acid within sufficient proximity to one another for energy transfer to occur between the labeling moieties. More specifically, one hybridization probe (a "donor probe") of the pair generally includes at least one donor moiety, while the other hybridization probe (an "acceptor probe") of the pair includes at least one acceptor moiety (e.g., LC-Red 610, LC-Red 640, LC-Red 670, LC-Red 705, JA-270, CY5, or CY5.5). The fluorescence emitted by the acceptor moieties of hybridization probes can be detected using various known methods, including those that utilize a LightCycler® system (Roche Diagnostics Corporation, Indianapolis, Ind., USA).

In other illustrative embodiments of using the oligonucleotides described herein, labeled primers are used to effect real-time target nucleic acid detection. Primer-based approaches to real-time target nucleic acid detection that can be adapted for use with the oligonucleotides described herein are also described in, e.g., Huang et al. (2004) "Real-time quantitative assay of telomerase activity using the duplex scorpion primer," *Biotechnol Lett.* 26(11):891-895, Asselbergs et al. (2003) "Rapid detection of apoptosis through real-time reverse transcriptase polymerase chain reaction measurement of the small cytoplasmic RNA Y1," *Anal Biochem.* 318(2):221-229, and Nuovo et al. (1999) "In situ amplification using universal energy transfer-labeled primers," *J Histochem Cytochem.* 47(3):273-280, which are each incorporated by reference.

IX. Systems

The invention also provides systems that can be used to perform many different assays. The systems include one or more oligonucleotides comprising 2'-terminator nucleotides. In certain embodiments, the oligonucleotides are arrayed on solid supports, whereas in others, they are provided in one or more containers, e.g., for assays performed in solution. In certain embodiments, the systems also include at least one detector or detection component (e.g., a spectrometer) that is configured to detect detectable signals produced in the container or on the support. In addition, the systems also optionally include at least one thermal modulator (e.g., a thermal cycling device) operably connected to the containers or solid supports to modulate temperature in the containers or on the solid supports, and/or at least one fluid transfer component (e.g., an automated pipettor) that transfers fluid to and/or from the containers or solid supports, e.g., for performing one or more proximity assays in the containers or on the solid supports.

Detectors are typically structured to detect detectable signals produced, e.g., in or proximal to another component of the given assay system (e.g., in a container and/or on a solid support). Suitable signal detectors that are optionally utilized, or adapted for use, herein detect, e.g., fluorescence, phosphorescence, radioactivity, absorbance, refractive index, luminescence, or mass. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, or scanning detectors. More specific exemplary detectors that are optionally utilized in performing the methods of the invention include, e.g., resonance light scattering detectors, emission spectroscopes, fluorescence spectroscopes, phosphorescence spectroscopes, luminescence spectroscopes, spectrophotometers, and photometers. Detectors are also described in, e.g., Skoog et al., *Principles of Instrumental Analysis*, $5^{th}$ Ed., Harcourt Brace College Publishers (1998), Currell, *Analytical Instrumentation: Performance Characteristics and Quality*, John Wiley & Sons, Inc. (2000), Sharma et al., *Introduction to Fluorescence Spectroscopy*, John Wiley & Sons, Inc. (1999), Valeur, *Molecular Fluorescence: Principles and Applications*, John Wiley & Sons, Inc. (2002), and Gore, *Spectrophotometry and Spectrofluorimetry: A Practical Approach*, $2^{nd}$ Ed., Oxford University Press (2000), which are each incorporated by reference.

The systems of the invention also typically include controllers that are operably connected to one or more components (e.g., detectors, thermal modulators, and/or fluid transfer components) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers. Controllers and/or other system components are optionally coupled to an appropriately programmed processor, computer, digital device, information appliance, or other logic device (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display or liquid crystal display), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements.

Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales.

Figure 4:
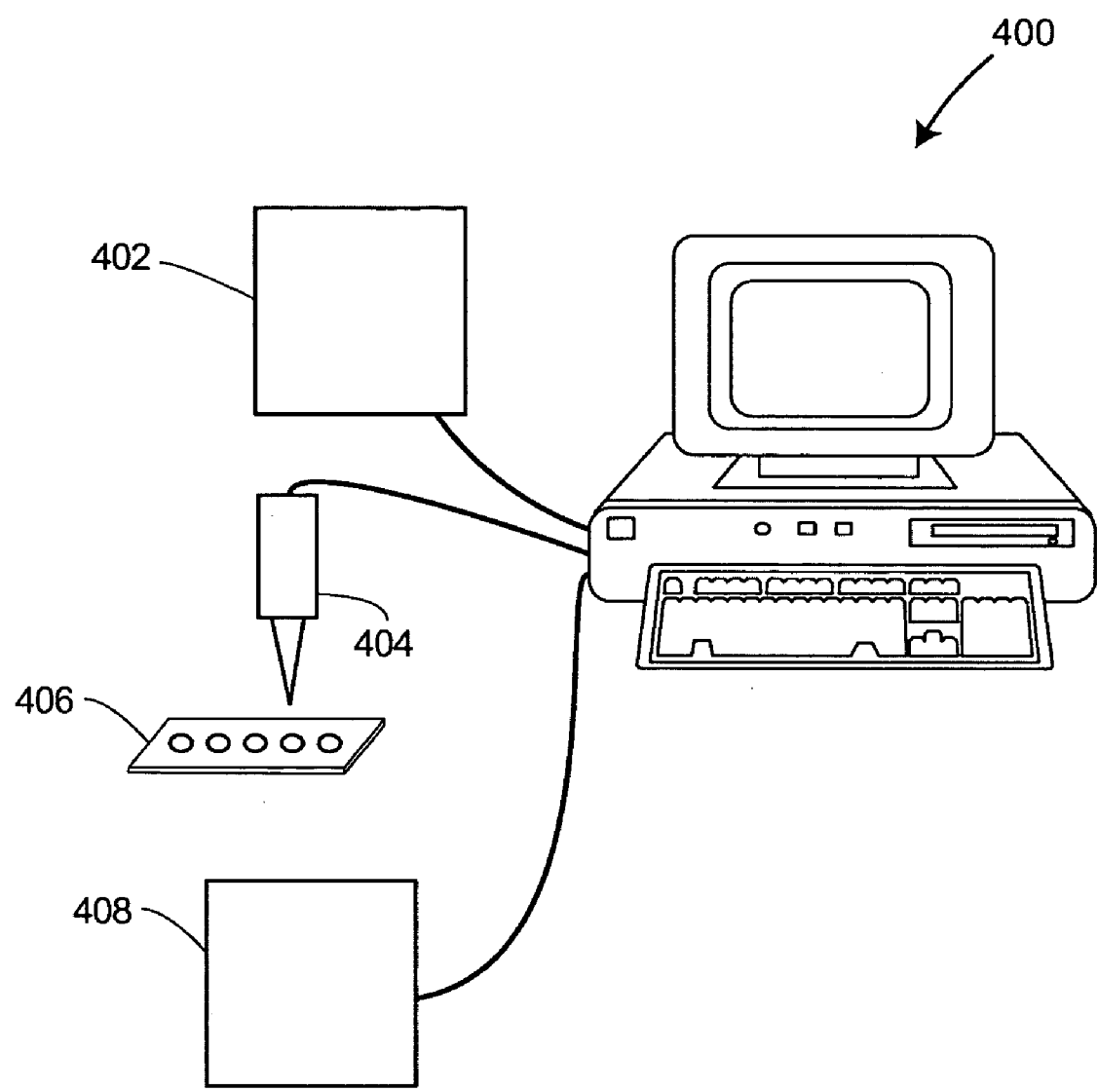
FIG. 4 is a block diagram showing a representative system.

FIG. 4 is a schematic showing a representative system that includes a logic device in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform as desired. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

More specifically, FIG. 4 schematically illustrates computer 400 to which detector 402 (e.g., a spectrometer, such as a spectrofluorometer), fluid transfer component 404, and thermal modulator 408 are operably connected. Optionally, one or more of these components are operably connected to computer 400 via a server (not shown in FIG. 4). During operation, fluid transfer component 404 typically transfers reaction mixtures or components thereof to multi-well container 406. Thermal modulation (e.g., thermal cycling) is typically effected by thermal modulator 408, which thermally communicates with multi-well container 406. Detector 402 typically detects detectable signals (e.g., fluorescent emissions) produced prior to, during, and/or after a given proximity assay is performed in the system. It will be apparent to one of skill in the art that one or more components of the system schematically depicted in FIG. 4 are optionally fabricated integral with one another (e.g., in the same housing).

X. EXAMPLES

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be included within the spirit and purview of this application and scope of the appended claims.

Example I

Synthesis of Blocked Oligonucleotides

Figure 5:
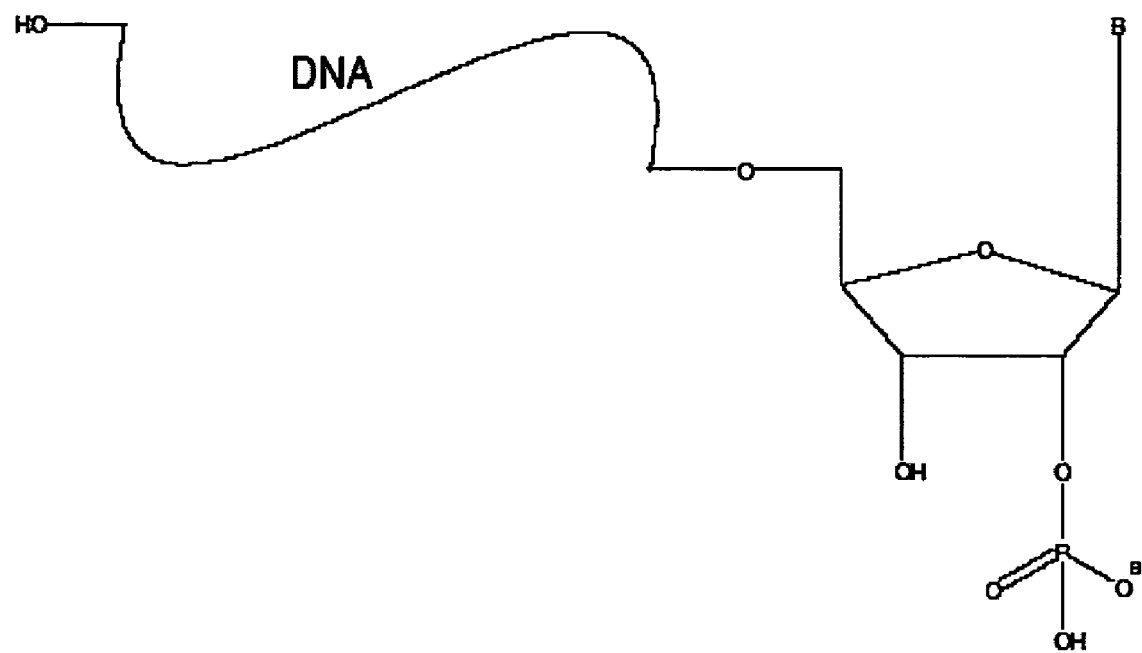
FIG. 5 schematically illustrates a blocked oligonucleotide according to one embodiment of the invention.
Figure 6:
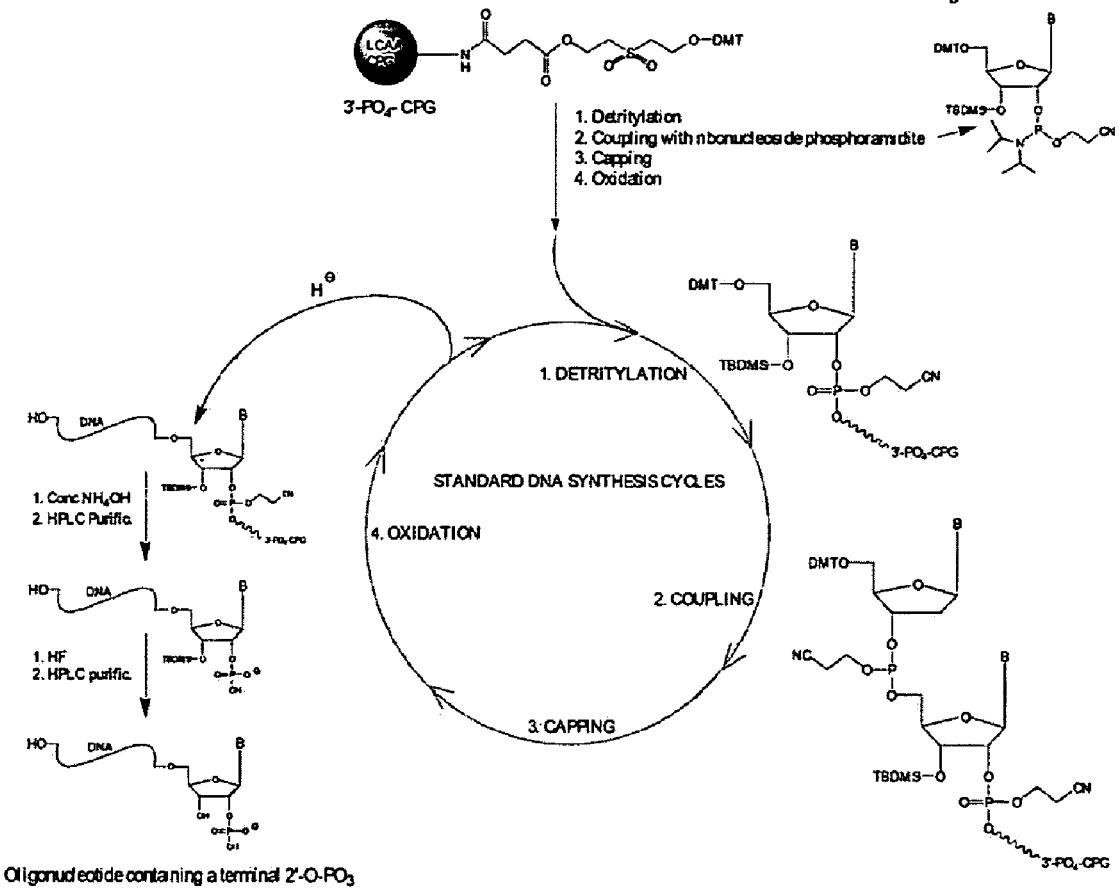
FIG. 6 schematically shows a solid-phase synthesis pathway for blocked oligonucleotides according to one embodiment of the invention.
Figure 7:
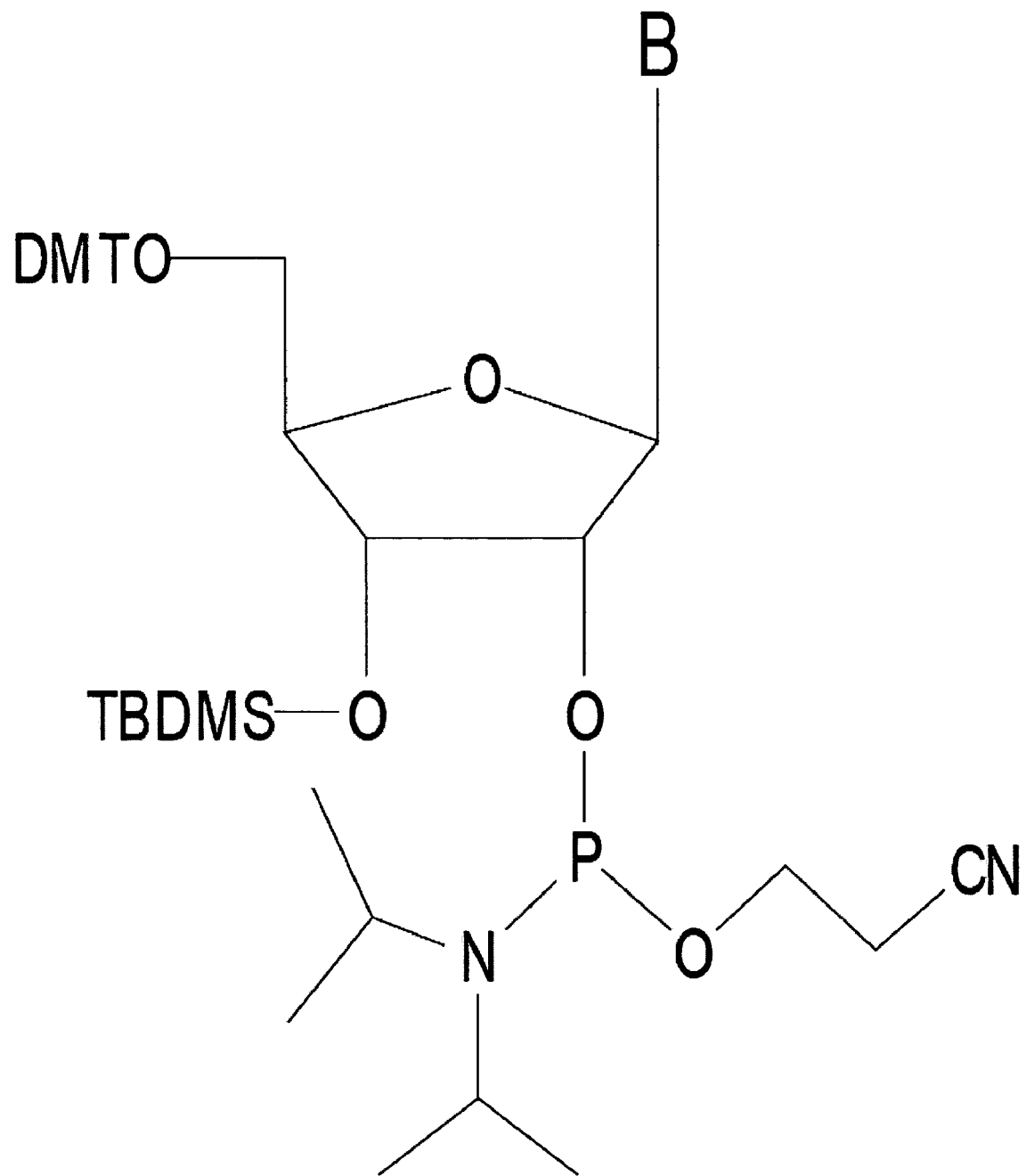
FIG. 7 schematically depicts a 3'-O-TBDMS-2'-O-phosphoramidite.

2'-O-$PO_3$ blocked oligonucleotides (FIG. 5) were synthesized on an automated Applied Biosystems 394 synthesizer using standard β-cyanoethylphosphoramidite chemistry (FIG. 6). The solid support used in the synthesis of these oligonucleotides was 3'-phosphate CPG (from Glen Research, # 20-2900-41), which facilitated the introduction of a phosphate group at the 3'-end of an oligonucleotide. In the first cycle of the synthesis, the ribonucleoside-2'-O-phosphoramidite (FIG. 7, where B=Bases; Adenosine (part # ANP-5681), Cytidine (ANP-5682), Guanosine (ANP-5683) and Uridine (ANP-5684)) purchased from ChemGenes, was used to couple with solid-support. In the second cycle of the synthesis and thereafter, the standard deoxynucleoside phosphoramidites were used. After the synthesis, the oligonucleotides were cleaved from the solid support and deprotected with concentrated ammonium hydroxide at room temperature for 24 to 48 hours. The ammonium hydroxide was then removed by size exclusion chromatography (NAP-10 column; elution with sterile water). The oligonucleotides were then purified by reversed-phase HPLC (PRP-1 column, triethyl ammonium acetate-acetonitrile buffer). The purified oligonucleotides were concentrated and then treated with potassium fluoride to remove the silyl protection of 3'-hydroxyl group at the 3'-end of oligonucleotide. The oligonucleotides were further purified by RP-HPLC (Xterra SB-18 column). The purity and identity of these oligonucleotides was confirmed by ion-exchange HPLC (Dionex, pH 8.0 at 60° C.) and LC-MS analysis.

Example II

HIV DNA Template Titrations

Figure 8:
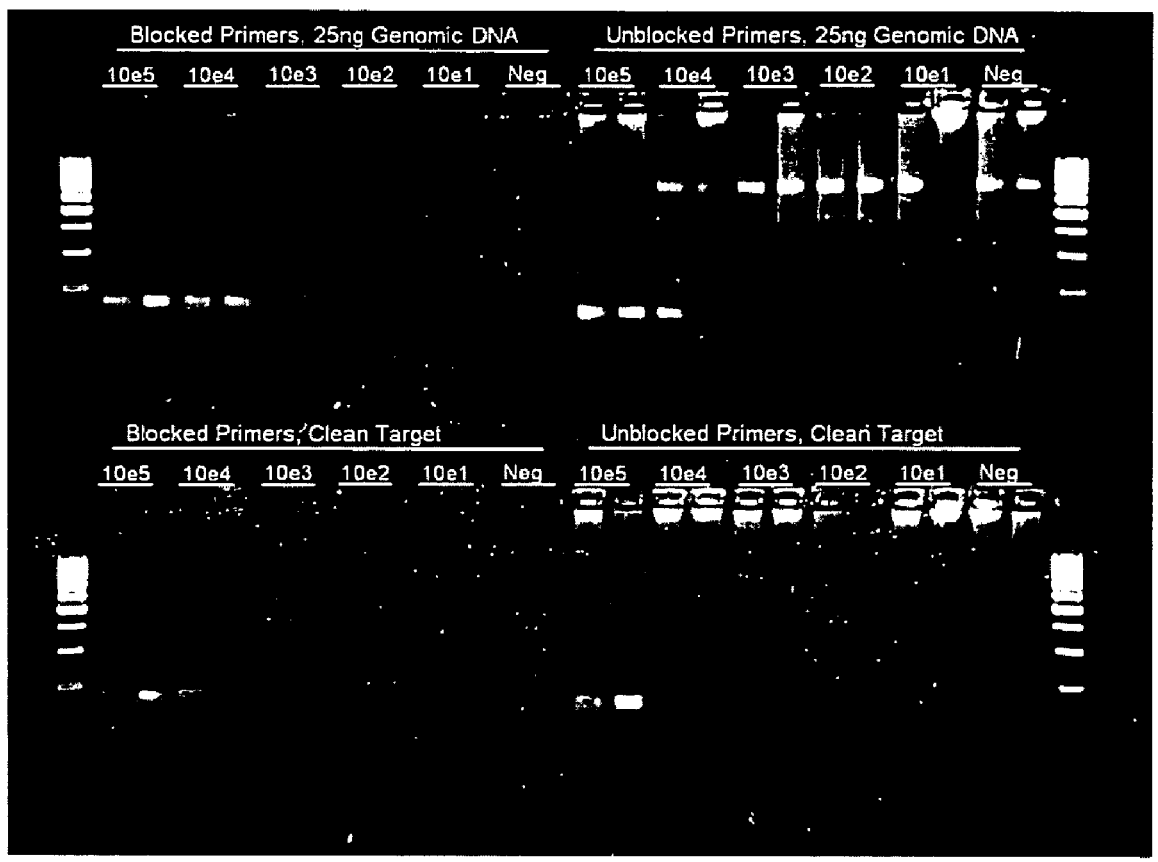
FIG. 8 is a photograph of a gel that shows the detection of PCR products from an analysis that involved PAP-related HIV DNA template titrations.

PAP-related HIV DNA template titrations were performed with and without the presence of genomic DNA. FIG. 8 is a photograph of a gel that shows the detection of the PCR products under the varied reaction conditions utilized in this analysis. This data illustrates, e.g., the improved amplification specificity and sensitivity that can be achieved using the blocked primers described herein relative to reactions not using those primers.

More specifically, the reactions were performed using an ABI 5700 Sequence Detection System with the following temperature profile:
50° C. 2 minutes
93° C. 1 minute
93° C., 15 seconds→52° C., 4 minutes×4 cycles
90° C., 15 seconds→55° C., 4 minutes×56 cycles The following reaction conditions were common to all reactions:

| Master Mix Components | conc. |
| --- | --- |
| Tricine (pH 8.0) | 100 mM |
| dATP | 200 μM |
| dCTP | 200 μM |
| dGTP | 200 μM |

-continued

| Master Mix Components | conc. |
|---|---|
| dTTP | 30 μM |
| dUTP | 300 μM |
| Primer 3 or Primer 1 | 200 nM |
| Primer 4 or Primer 2 | 200 nM |
| KOAc | 110 mM |
| SYBR Green I | 0.2X |
| NaPPi | 225 μM |
| Mg(OAc)$_2$ | 2.5 mM |
| Tth Storage Buffer (0.2% Tween) | 6% v/v |
| GLQDSE CS5 DNA polymerase | 10 nM |

Note, that "GLQDSE CS5 DNA polymerase" refers to a G46E L329A Q601R D640G S671F E678G CS5 DNA polymerase. Note further, that the "Tth Storage Buffer" included 0.2% Tween 20, 20 mM Tris pH8.0, 0.1 mM EDTA, 100 mM KCl, 1 mM DTT, and 50% v/v glycerol. In addition, each reaction volume was brought to 50 μL with diethylpyrocarbonate (DEPC) treated water.

The varied reaction components included the following unblocked primers (see, the reactions denoted "unblocked primers" in FIG. 8):

```
Primer 1
5'-TGAGACACCAGGAATTAGATATCAGTACAATGT-3'
(SEQ ID NO: 1)

Primer 2
5'-CTAAATCAGATCCTACATATAAGTCATCCATGT-3'
(SEQ ID NO: 2)
``` and the following blocked primers (see, the reactions denoted "blocked primers" in FIG. 8):

```
Primer 3
5'-TGAGACACCAGGAATTAGATATCAGTACAATGU*-3'
(SEQ ID NO: 3)

Primer 4
5'-CTAAATCAGATCCTACATATAAGTCATCCATGU*-3'
(SEQ ID NO: 4)
``` where U* refers to a 2'-Phosphate-U (i.e., a 2'-terminator nucleotide comprising a phosphate group at the 2' position). The reactions also either included (see, the reactions denoted "25 ng Genomic DNA" in FIG. 8) or lacked (see, the reactions denoted "Clean Target" in FIG. 8) 25 ng of human genomic DNA added to the mixtures. As further shown in FIG. 8, the reactions also included $10^5$, $10^4$, $10^3$, $10^2$, or $10^1$ copies of linearized plasmid DNA, which included the target nucleic acid, diluted in 1 μl HIV Specimen Diluent (10 mM Tris, 0.1 mM EDTA, 20 μg/mL Poly A, and 0.09% NaN$_3$) or 1 μl HIV Specimen Diluent in "Neg" reactions. The indicated primer pairs amplified a 170 base pair product from the plasmid DNA.

Example III

Figure 9:
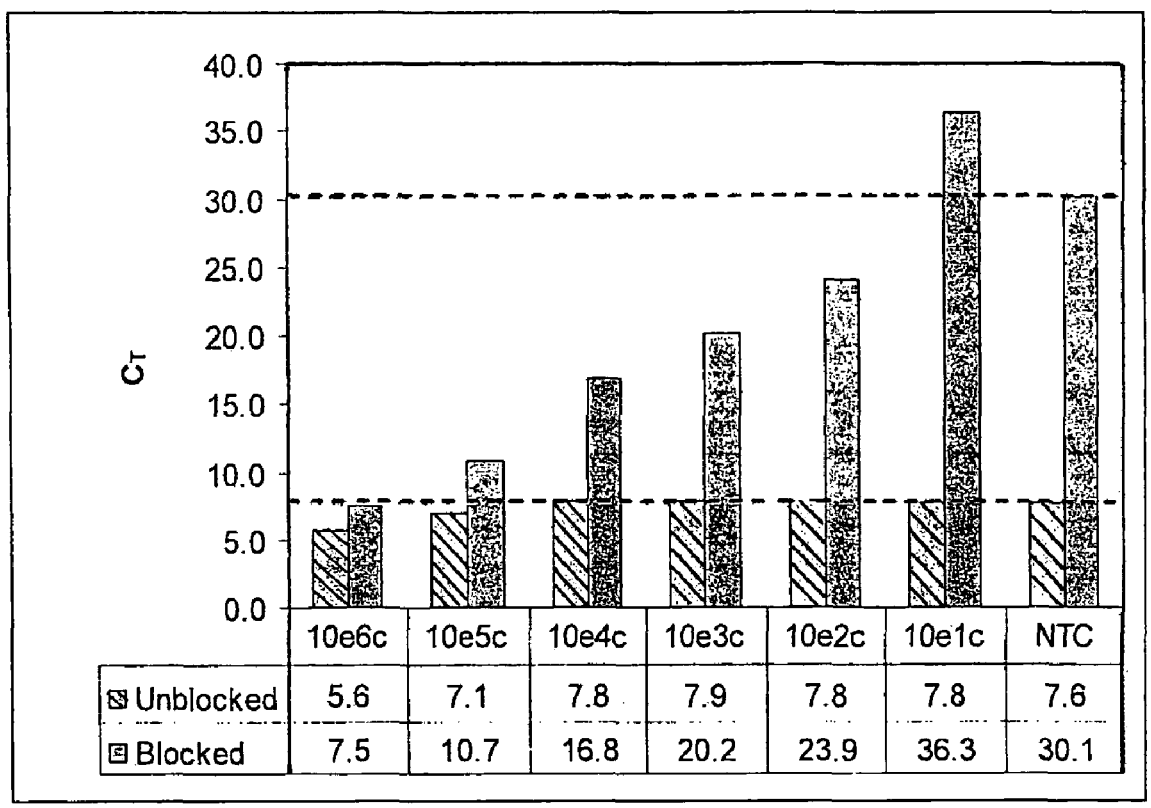
FIG. 9 is a graph that shows threshold cycle ($C_T$) values observed for various mutant K-Ras plasmid template copy numbers utilized in amplifications that involved blocked or unblocked primers.

Amplification of Mutant K-Ras Plasmid Template in a Background of Wild-Type K-Ras Plasmid Template Amplifications involving various copy numbers of mutant K-Ras plasmid template in a background of wild-type K-Ras plasmid template and comparing blocked and unblocked primers were performed. FIG. 9 is a graph that shows threshold cycle ($C_T$) values (y-axis) observed for the various mutant K-Ras plasmid template copy numbers (x-axis) utilized in these reactions. FIG. 9 further illustrates, e.g., the improved discrimination that can be achieved using the blocked primers described herein.

The reactions were performed using an ABI 5700 Sequence Detection System with the following temperature profile:
50° C. 2 minutes
93° C. 1 minute
92° C., 15 seconds→65° C., 2 minutes×60 cycles The following reaction conditions were common to all reactions:

| Master Mix Components | conc. |
|---|---|
| Tricine (pH 8.0) | 100 mM |
| dATP | 200 μM |
| dCTP | 200 μM |
| dGTP | 200 μM |
| dTTP | 30 μM |
| dUTP | 300 μM |
| Primer 7 or Primer 5 | 200 nM |
| Primer 8 or Primer 6 | 200 nM |
| SYBR Green I | 0.1X |
| NaPPi | 225 μM |
| Mg(OAc)$_2$ | 2.5 mM |
| Ung | 2 U |
| Tth Storage Buffer (0.2% Tween) | 6% v/v |
| GDSE CS5 DNA polymerase | 5 nM |
| Linearized Wild-Type Plasmid DNA | $10^6$ copies |

Note, that "GDSE CS5 DNA polymerase" refers to a G46E D640G S671 F E678G CS5 DNA polymerase. Note further, that the "Tth Storage Buffer" included 0.2% Tween 20, 20 mM Tris pH8.0, 0.1 mM EDTA, 100 mM KCl, 1 mM DTT, and 50% v/v glycerol. In addition, each reaction volume was brought to 50 μl with DEPC treated water.

The varied reaction components included the following unblocked primers (see, the reactions denoted "unblocked" in FIG. 9):

```
Primer 5
5'-AAACTTGTGGTAGTTGGAGCTC-3'
(SEQ ID NO: 5)

Primer 6
5'-GTTGGATCATATTCGTCCACAA-3'
(SEQ ID NO: 6)
``` and the following blocked primers (see, the reactions denoted "blocked" in FIG. 9):

```
Primer 7
5'-AAACTTGTGGTAGTTGGAGCTC*-3'
(SEQ ID NO: 7)

Primer 8
5'-GTTGGATCATATTCGTCCACAA*-3'
(SEQ ID NO: 8)
``` where C* refers to a 2'-Phosphate-C and A* refers to a 2'-Phosphate-A (i.e., 2'-terminator nucleotides comprising phosphate groups at 2' positions). In addition, $10^6$, $10^5$, $10^4$, $10^3$, $10^2$, $10^1$ or 0 copies (NTC reactions) (10e6c, 10e5c, 10e4c, 10e3c, 10e2c, 10e1c, and NTC, respectively, in FIG.

9) of linearized mutant K-Ras plasmid DNA were added to the reactions. The relevant subsequences of the mutant plasmid DNA were perfectly matched to both the blocked and unblocked primer sets. Further, the mutant K-Ras plasmid DNA was diluted in 1 µl HIV Specimen Diluent (see, above) or 1 µl HIV Specimen Diluent (see, above) in "NTC" reactions. Additionally, $10^6$ copies of linearized wild-type K-Ras plasmid DNA were present in all reactions. The wild-type K-Ras plasmid DNA was identical in sequence to mutant plasmid DNA except that it creates a C:C mismatch with the ultimate 3' base (dC) in primers 5 and 7. Both blocked and unblocked primer pairs created a 92 base pair amplicon on the mutant linearized plasmid template.

Example IV

Figure 10:
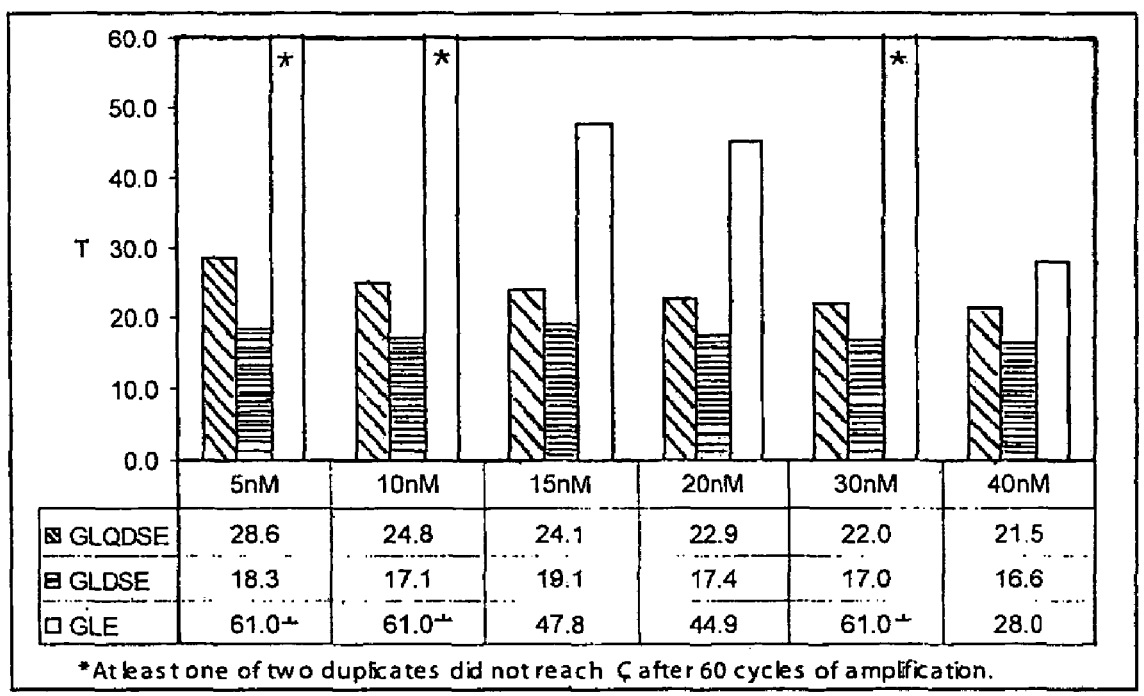
FIG. 10 is a graph that shows threshold cycle ($C_T$) values observed for various enzymes and enzyme concentrations utilized in amplifications that involved a K-Ras plasmid template.

Amplification of K-Ras Plasmid Template with Various Enzymes at Varied Concentrations Amplifications involving K-Ras plasmid template with various enzymes at varied concentrations were performed. FIG. 10 is a graph that shows threshold cycle ($C_T$) values (y-axis) observed for the various enzymes and concentrations (x-axis) utilized in these reactions. The reactions were performed using an ABI 5700 Sequence Detection System with the following temperature profile:

50° C. 2 minutes
93° C. 1 minute
92° C., 15 seconds→60° C., 2 minutes×60 cycles

The following reaction conditions were common to all reactions:

| Master Mix Components | conc. |
|---|---|
| Tricine (pH 8.0) | 100 mM |
| dATP | 200 µM |
| dCTP | 200 µM |
| dGTP | 200 µM |
| dTTP | 30 µM |
| dUTP | 300 µM |
| Primer 9 | 200 nM |
| Primer 10 | 200 nM |
| SYBR Green I | 0.1X |
| NaPPi | 225 µM |
| Mg(OAc)$_2$ | 2.5 mM |
| Ung | 2 U |
| Tth Storage Buffer (0.2% Tween) | 6% v/v |
| Linearized K-Ras Plasmid DNA | $10^4$ copies |

Note, that the "Tth Storage Buffer" included 0.2% Tween 20, 20 mM Tris pH 8.0, 0.1 mM EDTA, 100 mM KCl, 1 mM DTT, and 50% v/v glycerol. In addition, the reaction components included the following blocked primers:

```
Primer 9
5'-AAACTTGTGGTAGTTGGAGCTGU*-3'
(SEQ ID NO: 9)

Primer 10
5'-GTTGGATCATATTCGTCCACAA*-3'
(SEQ ID NO: 10)
``` where U* refers to a 2'-Phosphate-U and A* refers to a 2'-Phosphate-A (i.e., 2'-terminator nucleotides comprising phosphate groups at 2' positions). The primer pairs created a 92 base pair amplicon on the linearized K-Ras plasmid template. In addition, each reaction volume was brought to 50 µl with diethylpyrocarbonate (DEPC) treated water.

The polymerase concentration and KOAc concentrations were optimized for each individual polymerase as follows:

| Polymerase | Polymerase Conc. (nM) | KOAc (mM) |
|---|---|---|
| GLQDSE | 5, 10, 15, 20, 30, or 40 nM | 110 |
| GLDSE | 5, 10, 15, 20, 30, or 40 nM | 25 |
| GLE | 5, 10, 15, 20, 30, or 40 nM | 25 |

Note, that "GLQDSE" refers to a G46E L329A Q601R D640G S671F E678G CS5 DNA polymerase, "GLDSE" refers to a G46E L329A D640G S671F E678G CS5 DNA polymerase, and "GLE" refers to a G46E L329A E678G CS5 DNA polymerase.

Example V

Pap-Related Enzyme Comparisons

The abilities of G46E L329A E678G CS5 DNA polymerase and G46E L329A D640 S671F E678G CS5 DNA polymerase to perform pyrophosphorolysis activated polymerization ("PAP") were compared. The reaction buffer was comprised of 100 mM Tricine pH 8.0, 0 mM (G46E L329A E678G CS5 DNA polymerase) or 50 mM (G46E L329A D640 S671F E678G CS5 DNA polymerase) KOAc, 10% v/v glycerol, 0.04 U/µl UNG, 4 mM Mg(OAc)$_2$, 0.2X SYBR Green I, 2.5% v/v enzyme storage buffer (50% v/v glycerol, 100 mM KCl, 20 mM Tris pH 8.0, 0.1 mM EDTA, 1 mM DTT, 0.5% Tween 20), 0.2 mM each dATP, dCTP, and dGTP, and 0.4 mM dUTP, and 100 µM pyrophosphate. M13 template (GenBank Accession No. X02513) and enzyme were cross-titrated. M13 concentrations used were 0, $10^4$, $10^5$, and $10^6$ copies per 20 µl reaction. Enzyme concentrations used were 2.5 nM, 5 nM, 10 nM, 15 nM, 20 nM, 25 nM, 35 nM, and 50 nM. Reactions were set up in triplicate in a 384-well thermocycler, using the following cycling parameters: 50° C. for 2 minutes; 90° C. for 1 minute; then 46 cycles of: 90° C. for 15 seconds followed by an extension temperature of 62° C. for 60 seconds.

The primer sequences used were 5'-CGCCTGGTCTGTA-CACCGTTXA-3' (SEQ ID NO: 11) (primer 11) and 5'-GGAACGAGGGTAGCAACGGCTACE-3' (SEQ ID NO: 12) (primer 12), where X=2'-amino-C and E=2'-PO$_4$-A (i.e., a 2'-terminator nucleotide). These primers, added to the reaction mix at 0.1 µM each, result in a 348 bp product from M13 template. In order to serve as a primer, primer 12 must be activated by pyrophosphorolytic removal of the terminal residue.

Figure 11:
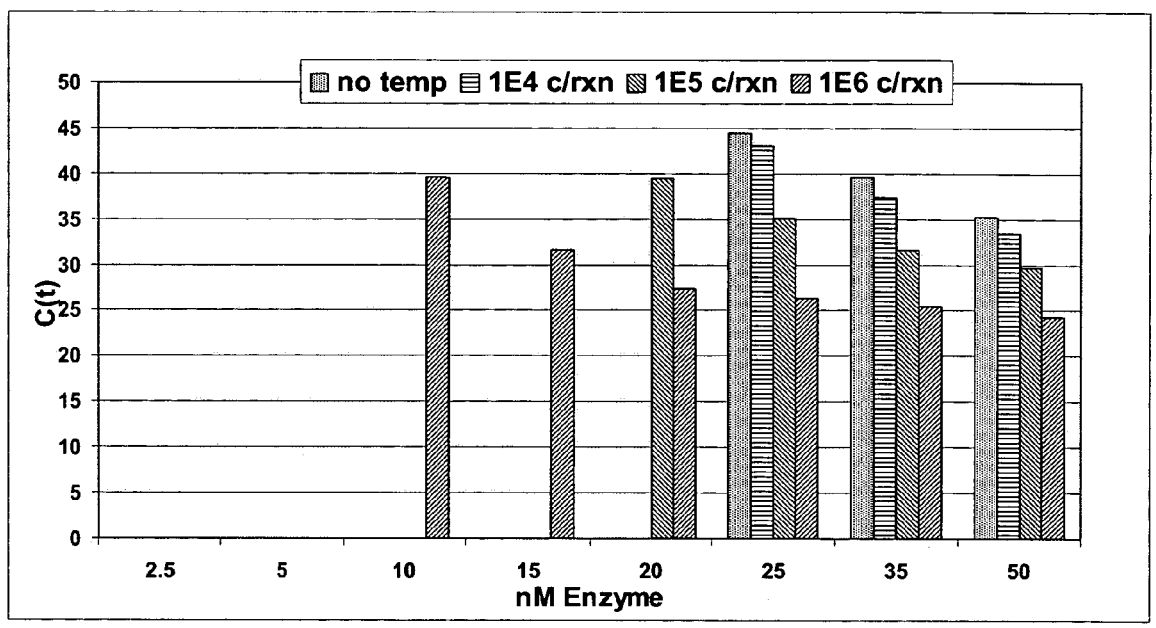
FIG. 11 is a bar graph that shows the effect of enzyme concentration on threshold cycle (Ct) values in pyrophosphorolysis activated polymerization (PAP) reactions utilizing a G46E L329A E678G (GLE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), $1e^4$ copies of the template nucleic acid (1E4/rxn), $1e^5$ copies of the template nucleic acid (1E5/rxn), and $1e^6$ copies of the template nucleic acid (1E6/rxn)).
Figure 12:
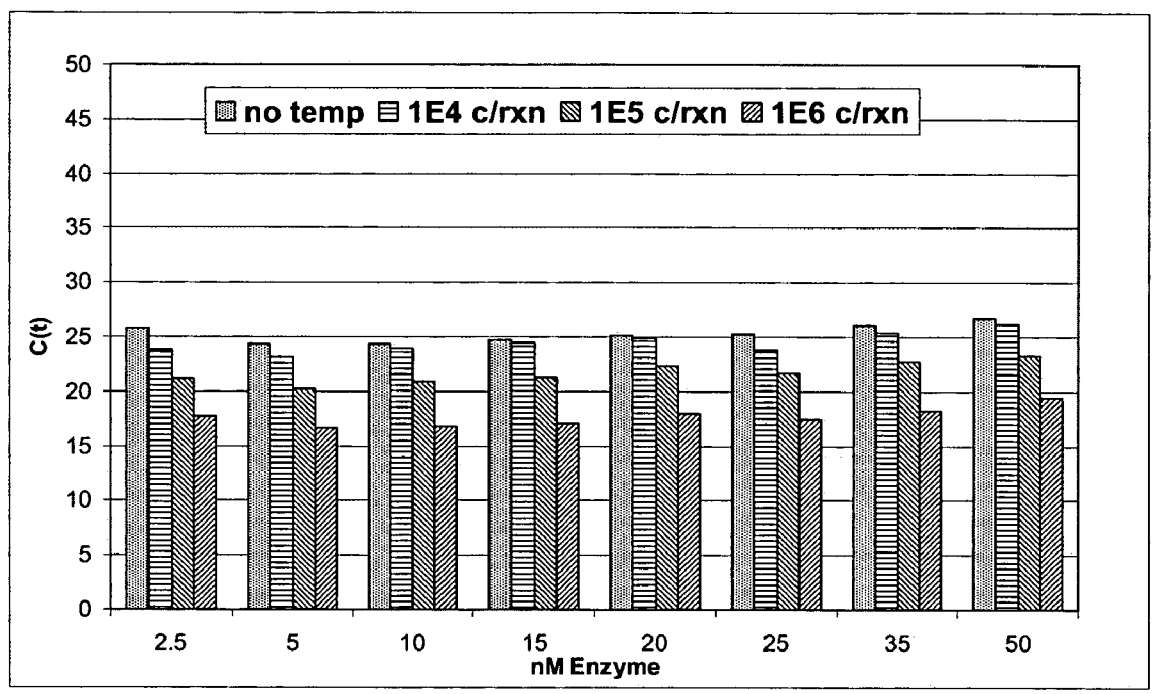
FIG. 12 is a bar graph that shows the effect of enzyme concentration on threshold cycle (Ct) values in pyrophosphorolysis activated polymerization (PAP) reactions utilizing a G46E L329A D640G S671F E678G (GLDSE) CS5 DNA polymerase. The y-axis represents Ct value, while the x-axis represents the enzyme concentration (nM). The legend that accompanies the plot shows the number of copies of the template nucleic acid corresponding to each trace in the graph (no copies of the template nucleic acid (no temp), $1e^4$ copies of the template nucleic acid (1E4/rxn), $1e^5$ copies of the template nucleic acid (1E5/rxn), and $1e^6$ copies of the template nucleic acid (1E6/rxn)).

Fluorescence data was analyzed to determine elbow values (i.e., C(t) (emergence of fluorescence over baseline)). C(t) values for G46E L329A E678G CS5 DNA polymerase are shown in FIG. 11. C(t) values for G46E L329A D640G S671F E678G CS5 DNA polymerase are shown in FIG. 12.

Example VI

Hepatitis C Virus (HCV) RNA to CDNA Reverse Transcription (RT) Comparing Unblocked and Blocked RT Primers The extension of an unblocked HCV RT primer was compared to the extension of a blocked primer on an HCV RNA template in reverse transcription reactions. These RT comparisons were performed using various polymerases. To illustrate, FIG. 13 is a graph that shows threshold cycle (Ct) values (y-axis) observed for the various enzymes (x-axis) utilized in these reactions in which the cDNA was measured using real-time PCR involving 5'-nuclease probes.

The following reaction conditions were common to all RT reactions:

| RT Mix Component | Concentration |
|---|---|
| Tricine pH 8.0 | 100 mM |
| KOAc | 100 mM |
| DMSO | 4% (v/v) |
| Primer 1 or 2 | 200 nM |
| dATP | 200 μM |
| dCTP | 200 μM |
| dGTP | 200 μM |
| dTTP | 30 μM |
| dUTP | 300 μM |
| UNG | 0.2 Unit |
| Mn(OAc)$_2$ | 1 mM |
| PPi | 175 uM |

Figure 13:
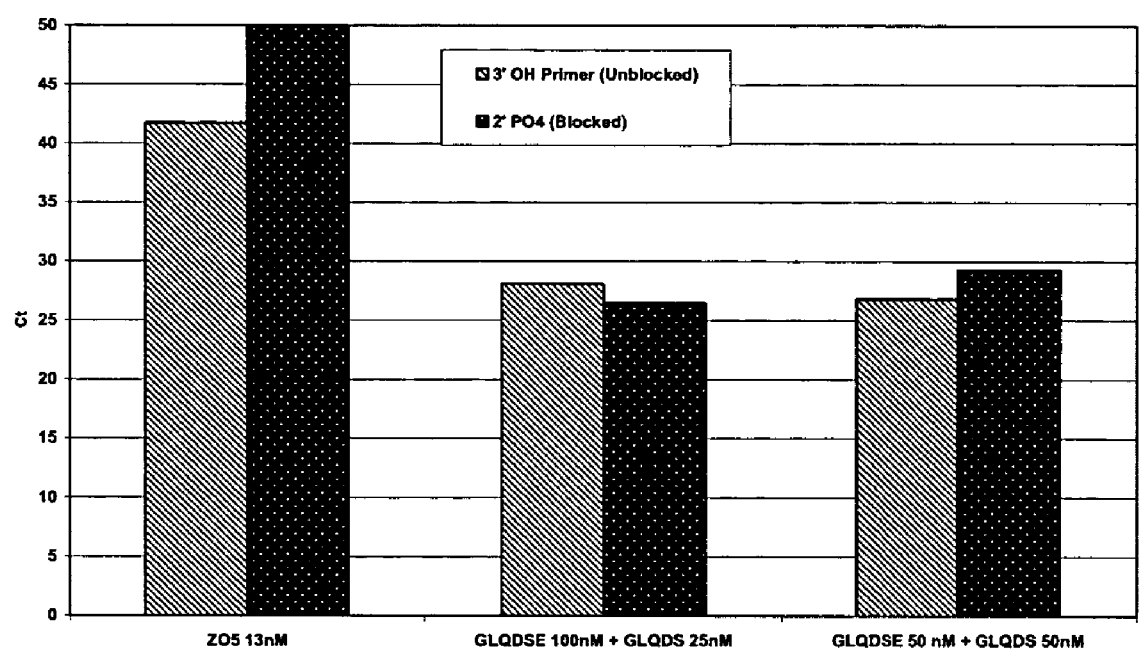
FIG. 13 is a bar graph that shows data for PAP reverse transcription reactions on HCV RNA in which products of the cDNA reaction were measured using a quantitative PCR assay specific for the HCV cDNA. The y-axis represents Ct value, while the x-axis represents the Units of enzyme utilized in the reactions. As indicated, the enzymes used in these reactions were ZO5 DNA polymerase (ZO5) or blends of G46E L329A Q601R D640G S671F E678G (GLQDSE) and G46E L329A Q601R D640G S671F (GLQDS) CS5 DNA polymerases.

The varied reaction components included the following 3'-OH unblocked primer (see, the reactions denoted "3' OH Primer (Unblocked)" in FIG. 13):

```
Primer 1
5'-GCAAGCACCCTATCAGGCAGTACCACAA-3'
(SEQ ID NO: 13)
``` and the following blocked primer (see, the reactions denoted "2' PO4 (Blocked)" in FIG. 13):

```
Primer 2
5'-GCAAGCACCCTATCAGGCAGTACCACAA*-3'
(SEQ ID NO: 14)
``` where A* refers to a 2'-Phosphate-A or a 2'-monophosphate-3'-hydroxyl adenosine nucleotide (i.e., 2' terminator nucleotide comprising a phosphate group at the 2' position). Further, the following polymerase conditions were compared in the cDNA reactions (see, FIG. 13):

ZO5 DNA polymerase (13 nM)

GLQDSE CS5 DNA polymerase (100 nM) combined with GLQDS CS5 DNA polymerase (25 nM)

GLQDSE CS5 DNA polymerase (50 nM) combined with GLQDS CS5 DNA polymerase (50 nM where "GLQDSE CS5 DNA polymerase" refers to a G46E L329A Q601R D640G S67 1F E678G CS5 DNA polymerase and "GLQDS CS5 DNA polymerase" refers to a G46E L329A Q601R D640G S671F CS5 DNA polymerase. In addition, each reaction was brought to 20 μl with diethylpyrocarbonate (DEPC) treated water.

The RT reactions were incubated at 60° C. for 60 minutes in an ABI 9600 Thermal Cycler. After the RT incubation, RT reactions were diluted 100-fold in DEPC treated water. The presence of cDNA was confirmed and quantitated by 5'nuclease probe-based real-time HCV PCR reactions designed to specifically measure the HCV cDNA products of the RT reactions. These reactions were performed using an ABI Prism 7700 Sequence Detector with the following temperature profile:

50° C. 2 minutes
95° C. 15 seconds→60° C. 1 minutes×50 cycles.

Example VII

Bidirectional PAP for BRAF Mutation Detection

Figure 14:
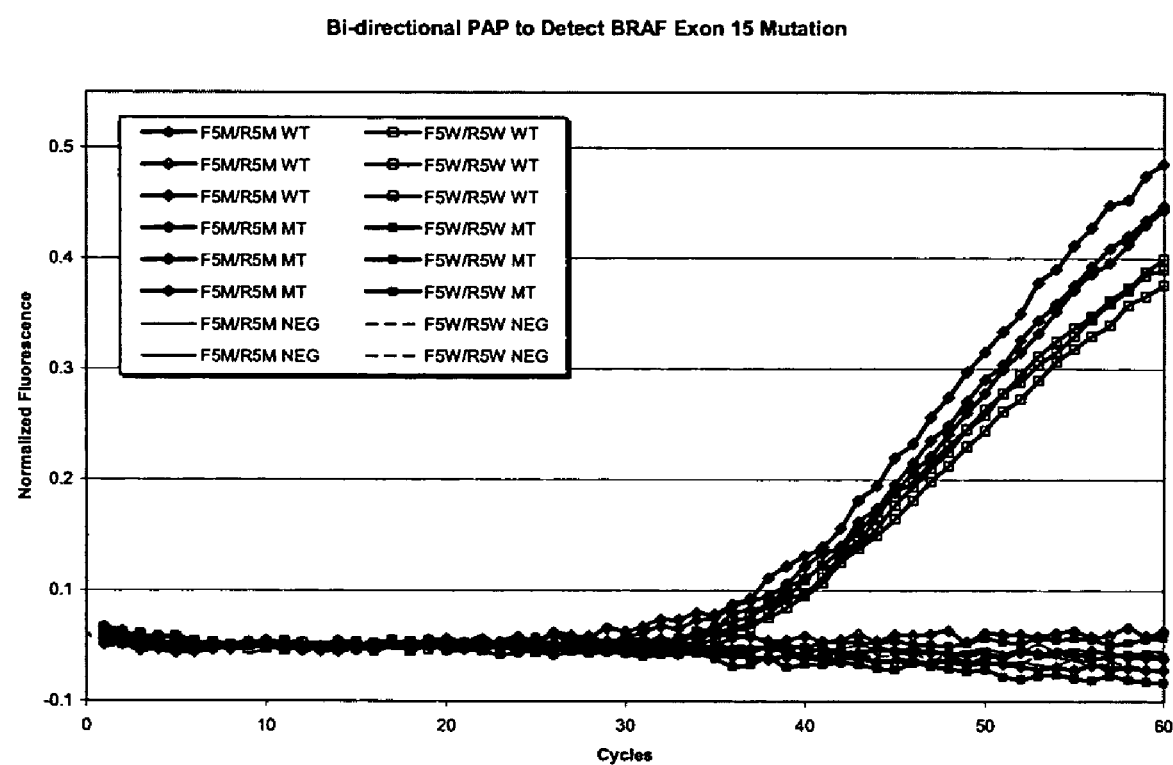
FIG. 14 shows PCR growth curves of BRAF oncogene amplifications that were generated when bidirectional PAP was performed. The x-axis shows normalized, accumulated fluorescence and the y-axis shows cycles of PAP PCR amplification.

FIG. 14 shows PCR growth curves of BRAF oncogene amplifications that were generated when bidirectional PAP was performed. The x-axis shows normalized, accumulated fluorescence and the y-axis shows cycles of PAP PCR amplification. More specifically, these data were produced when mutation-specific amplification of the T→A mutation responsible for the V599E codon change in the BRAF oncogene (see, Brose et al. (2002) *Cancer Res* 62:6997-7000, which is incorporated by reference) was performed using 2'-terminator blocked primers that overlap at their 3'-terminal nucleotide at the precise position of the mutation. When primers specific to wild-type sequence were reacted to wild-type target or mutant target, only wild-type target was detected. Conversely, when primers specific to mutant sequence were reacted to wild-type target or mutant target, only mutant target was detected.

The following reaction conditions were common to all RT reactions:

| Component | Concentration |
|---|---|
| Tricine pH 8.0 | 100 mM |
| KOAc | 100 mM |
| Glycerol | 3.5% v/v |
| Primer F5W or F5M | 200 nM |
| Primer R5W or R5M | 200 nM |
| dATP | 200 μM |
| dCTP | 200 μM |
| dGTP | 200 μM |
| dTTP | 30 μM |
| dUTP | 300 μM |
| UNG | 1 Unit |
| PPi | 175 uM |
| GLQDSE | 15 nM |
| SYBR I/carboxyrhodamine | 1/100,000 (0.1x) |
| Mg(OAc)$_2$ | 3.0 mM | where "GLQDSE" refers to a G46E L329A Q601R D640G S671F E678G CS5 DNA polymerase.

The varied reaction components included the following wild-type BRAF primers (labeled "F5W/R5W" in FIG. 14):

```
F5W
5'-AATAGGTGATTTTGGTCTAGCTACAGU*-3'
(SEQ ID NO: 15)

R5W
5'-GGACCCACTCCATCGAGATTTCA*-3'
(SEQ ID NO: 16)
``` and the following mutant BRAF primers (labeled "F5M/R5M" in FIG. 14):

```
F5M
5'-AATAGGTGATTTTGGTCTAGCTACAGA*-3'
(SEQ ID NO: 17)

R5M
5'-GGACCCACTCCATCGAGATTTCU*-3'
(SEQ ID NO: 18)
``` where A* refers to a 2'-Phosphate-A or a 2'-monophosphate-3'-hydroxyl adenosine nucleotide and U* is a 2'-Phosphate-U or a 2'-monophosphate-3'-hydroxyl uridine nucleotide (i.e., 2' terminator nucleotides comprising a phosphate group at the 2' position).

In addition, each reaction was brought to 50 µl with DEPC treated water. Wild-type reactions (labeled "WT" in FIG. 14) contained linearized DNA plasmid of the BRAF wild-type sequence and mutant reactions (labeled "MT" in FIG. 14) contained linearized DNA plasmid of the BRAF mutant sequence. Negative reactions (labeled "NEG" in FIG. 14) contained HIV specimen diluent (10 mM Tris, 0.1 mM EDTA, 20 µg/mL Poly A, and 0.09% NaN$_3$) with no DNA. Combinations of the primers in PCR produced a 50 bp amplicon. Further, the reactions were performed using an ABI Prism 7700 Sequence Detector with the following temperature profile:

50° C. 1 minute
93° C. 1 minute
90° C. 15 seconds
60° C. 150 seconds→×60 Cycles.

Example VIII

Detection of Fluorescent PAP Release Product

This prophetic example illustrates a real-time monitoring protocol that involves PAP activation in which a blocked primer leads to the production of detectable signal as that primer is activated and extended.

Construction of a 3' Terminated, Dual-labeled Oligonucleotide Primer:

The primer QX below is a DNA oligonucleotide that includes a quenching dye molecule, Black Hole Quencher® (BHQ) (Biosearch Technologies, Inc.) attached to the thirteenth nucleotide (A) from the 3' terminus.

An oligonucleotide primer of the QX is mixed in solution with a complimentary oligonucleotide R1 (see, below) such that they form a hybrid duplex. This duplex is further mixed with the reagents in the Table IV provided below which notably include a fluorescein-labeled deoxyriboadenine tetraphosphate (i.e., a fluorescein-labeled 2'-terminator nucleotide) and DNA polymerase capable of incorporating such labeled tetraphosphate. See, U.S. patent application Ser. No. 10/879,494, entitled "SYNTHESIS AND COMPOSITIONS OF 2'-TERMINATOR NUCLEOTIDES", filed Jun. 28, 2004 and Ser. No. 10/879,493, entitled "2'-TERMINATOR NUCLEOTIDE-RELATED METHODS AND SYSTEMS," filed Jun. 28, 2004, which are both incorporated by reference. Incubation of the mixture at a temperature of 60° C. for, e.g., one hour could causes the 3' terminus of the sequence QX to be extended one nucleotide in a template directed manner, resulting in at least a portion of the QX oligonucleotides being extended at their 3' ends with the fluorescein-labeled deoxyriboadenine 2'-phosphate nucleotides, represented below as Primer QX$^{FAM}$.

TABLE IV

| Mix Component | Concentration |
| --- | --- |
| Tricine pH 8.3 | 50 mM |
| KOAc | 100 mM |
| Glycerol | 8% (w/v) |
| Primer QX | 10 µM |
| Oligonucleotide R1 | 15 µM |
| Fluorescein dA4P | 15 µM |
| G46E L329A E678G CS5 DNA | 50 nM |

TABLE IV-continued

| Mix Component | Concentration |
| --- | --- |
| polymerase | |
| Mg(OAc)$_2$ | 2.5 mM |

The newly elongated Primer QX$^{FAM}$ are purified from the mixture above using any number of purification methods known to persons of skill in the art. An example of such a method capable of purifying Primer QX$^{FAM}$ from the mixture is High Peformance Liquid Chromatography (HPLC). HPLC purification parameters are selected such that the preparation of Primer QX$^{FAM}$ is substantially free of non-extended Primer QX and fluorescein-labeled adenine tetraphosphates. Dual HPLC (Reverse Phase and Anion Exchange HPLC) is known as a method for purifying such molecules.

Once purified, molecules such as Primer QX$^{FAM}$ which contain a BHQ quenching molecule and a fluorescein molecule on the same oligonucleotide generally exhibit a suppressed fluorescein signal due to energy absorbance by the BHQ2 "quencher" molecule.

Optionally, Primer QX$^{FAM}$ is synthesized chemically as described herein.

The sequences referred to in this example are as follows:

```
Primer QX
5'-GCAAGCACCCTATCA^QGGCAGTACCACA-3'
(SEQ ID NO: 19)
```

(Where Q represents the presence of a BHQ molecule)

```
R1
3'-PCGTTCGTGGGATAGTCCGTCATGGTGTT-5'
(SEQ ID NO: 20)
```

(Where P represents 3'phosphate)

```
Primer QX^FAM
5'-GCAAGCACCCTATCA^QGGCAGTACCACA^F-3'
(SEQ ID NO: 21)
```

(Where Q represents the presence of a BHQ molecule, and F represents a fluorescein-labeled 2' phosphate adenine)

```
Primer HC2
5'-GCAGAAAGCGTCTAGCCATGGCTTA-3'.
(SEQ ID NO: 22)
```

Use of the Primer in PCR.

A Primer QX$^{FAM}$ as described above is combined with the reagents in Table V.

TABLE V

| Component | Concentration |
| --- | --- |
| Tricine pH 8.0 | 100 mM |
| KOAc | 100 mM |
| Glycerol | 3.5% (v/v) |
| DMSO | 5% (v/v) |
| Primer QX$^{FAM}$ | 150 nM |
| Primer HC2 | 150 nM |
| dATP | 200 µM |
| dCTP | 200 µM |
| dGTP | 200 µM |
| dTTP | 30 µM |

TABLE V-continued

| Component | Concentration |
| --- | --- |
| dUTP | 300 μM |
| UNG | 1 Unit |
| PPi | 175 μM |
| GLQDSE | 15 nM |
| Target sequence | $10^6$ copies |
| Mg(OAc)$_2$ | 3.0 mM |

In addition each reaction is brought to 50 μl with DEPC treated water. Some reactions contain a target sequence which serves as a substrate for PCR amplification, while others contain no target. For example, the target can be a DNA sequence identical to the 5'UTR region of the HCV genome. Combinations of these primers in PCR are expected to produce an approximately 244 bp amplicon.

The reactions can be performed using an ABI Prism 7700 Sequence Detector with the following temperature profile:
50° C. 1 minute
93° C. 1 minute
90° C. 15 seconds
60° C. 150"→×60 Cycles For such a PCR to progress, PAP activation of the fluorescein-terminated Primer QX$^{FAM}$ is necessary, and would result in the removal of the fluorescein-labeled deoxyadenine tetraphosphate molecule. Such a release is expected to result in an increase in fluorescent signal at approximately 520 nm wavelength. With monitoring of signal at approximately 520 nm wavelength as the PCR progresses, one would expect to observe an increase in fluorescence in those reactions containing target nucleic acid while observing no increased fluorescence in reactions that do not contain target.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of removing a nucleotide from an oligonucleotide, the method comprising:
    incubating at least one target nucleic acid with:
        pyrophosphate;
        at least a first biocatalyst comprising a pyrophosphorolysis activity, and
        at least one oligonucleotide comprising a 2'-terminator nucleotide, which oligonucleotide is at least partially complementary to at least a first subsequence of the target nucleic acid,
    under conditions whereby the first biocatalyst removes at least the 2'-terminator nucleotide from the oligonucleotide to produce a removed 2'-terminator nucleotide and a shortened oligonucleotide, thereby removing the nucleotide from the oligonucleotide.

2. The method of claim 1, wherein the oligonucleotide comprises the 2'-terminator nucleotide at a 3'-terminus.

3. The method of claim 1, wherein the oligonucleotide comprises a primer nucleic acid or a probe nucleic acid.

4. The method of claim 1, wherein the 2'-terminator nucleotide is non-extendible by one or more nucleotide incorporating biocatalysts selected from the group consisting of: a G46E E678G CS5 DNA polymerase, a G46E L329A E678G CS5 DNA polymerase, a G46E L329A D640G S671F CS5 DNA polymerase, a G46E L329A D640G S671F E678G CS5 DNA polymerase, a G46E E678G CS6 DNA polymerase, a ΔZO5R polymerase, a E615G Taq DNA polymerase, a *Thermus flavus* polymerase, a TMA-25 polymerase, a E678G TMA-25 polymerase, a TMA-30 polymerase, a E678G TMA-30 polymerase, a Tth DNA polymerase, a *Thermus* species SPS-17 polymerase, a E615G Taq polymerase, a *Thermus* ZO5R polymerase, a T7 DNA polymerase, a Kornberg DNA polymerase I, a Klenow DNA polymerase, a Taq DNA polymerase, a Micrococcal DNA polymerase, an alpha DNA polymerase, a reverse transcriptase, an AMV reverse transcriptase, an M-MuLV reverse transcriptase, a DNA polymerase, a T4 DNA polymerase, a ribonucleotide analog-incorporating DNA polymerase, and a ribonucleotide incorporating DNA polymerase.

5. The method of claim 1, wherein the target nucleic acid comprises at least one polymorphic nucleotide position, and wherein the method comprises detecting removal of the 2'-terminator nucleotide from the oligonucleotide, which removal correlates with the oligonucleotide comprising at least one nucleotide position that corresponds to the polymorphic nucleotide position.

6. The method of claim 5, wherein the 2'-terminator nucleotide corresponds to the polymorphic nucleotide position.

7. The method of claim 1, wherein the oligonucleotide comprises at least one label, and wherein the method comprises detecting a detectable signal emitted from the label.

8. The method of claim 7, wherein the label comprises a donor moiety and/or an acceptor moiety and the detectable signal comprises light emission, and wherein the method comprises incubating the target nucleic acid with the first biocatalyst, the oligonucleotide, and at least one soluble light emission modifier and detecting the light emission from the donor moiety and/or the acceptor moiety.

9. The method of claim 8, wherein the 2'-terminator nucleotide comprises the donor moiety and/or the acceptor moiety.

10. The method of claim 1, wherein the first biocatalyst comprises a nucleotide incorporating activity, and wherein the method comprises incubating the target nucleic acid with the first biocatalyst, the shortened oligonucleotide, and at least one additional nucleotide under conditions whereby the first biocatalyst incorporates the additional nucleotide at a terminus of the shortened oligonucleotide to produce an extended oligonucleotide; or,
    wherein the method comprises incubating the target nucleic acid with at least a second biocatalyst comprising a nucleotide incorporating activity, the shortened oligonucleotide, and at least one additional nucleotide under conditions whereby the second biocatalyst incorporates the additional nucleotide at a terminus of the shortened oligonucleotide to produce an extended oligonucleotide.

11. The method of claim 10, wherein the first and/or second biocatalyst comprises an enzyme selected from the group consisting of: a polymerase and a reverse transcriptase.

12. The method of claim 10, wherein the nucleotide incorporating activity comprises a polymerase activity and/or a ligase activity.

13. The method of claim 10, wherein one or more nucleotides of the oligonucleotide extend beyond a terminus of the target nucleic acid when the oligonucleotide and the target nucleic acid hybridize to form a hybridized nucleic acid.

14. The method of claim 10, wherein at least one additional oligonucleotide comprises the additional nucleotide.

15. The method of claim 10, wherein the additional nucleotide comprises an extendible nucleotide.

16. The method of claim 10, wherein the first and/or second biocatalyst comprises a CS5 DNA polymerase comprising one or more mutations at amino acid positions selected from the group consisting of: G46, L329, Q601, D640, I669, S671, and E678.

17. The method of claim 16, wherein the mutations comprise a G46E mutation, an L329A mutation, a Q601R mutation, a D640G mutation, an I669F mutation, an S671F mutation, and/or an E678G mutation.

18. The method of claim 10, wherein the additional nucleotide comprises at least one label, and wherein the method comprises detecting a detectable signal emitted from the label.

19. The method of claim 18, wherein the label comprises a donor moiety and/or an acceptor moiety and the detectable signal comprises light emission, and wherein the method comprises incubating the target nucleic acid with at least one soluble light emission modifier and detecting the light emission from the label.

20. The method of claim 10, comprising incubating the target nucleic acid with at least one probe nucleic acid that comprises at least one label, which probe nucleic acid is at least partially complementary to at least a second subsequence of the target nucleic acid, and detecting a detectable signal emitted from the label of the probe nucleic acid or a fragment thereof.

21. The method of claim 20, wherein the detectable signal comprises light emission, and wherein the method further comprises incubating the target nucleic acid with at least one soluble light emission modifier and detecting the light emission from the label.

22. The method of claim 20, wherein the probe nucleic acid comprises a 5'-nuclease probe and the first and/or second biocatalyst extends the shortened oligonucleotide in a 5' to 3' direction and comprises a 5' to 3' exonuclease activity.

23. The method of claim 20, wherein the probe nucleic acid comprises a hybridization probe and/or a hairpin probe.

24. The method of claim 10, wherein the target nucleic acid comprises at least one polymorphic nucleotide position, and wherein the method comprises detecting extension of the shortened oligonucleotide, which extension correlates with the extended oligonucleotide comprising at least one nucleotide position that corresponds to the polymorphic nucleotide position.

25. The method of claim 24, wherein the 2'-terminator nucleotide corresponds to the polymorphic nucleotide position.

26. The method of claim 1, wherein the 2'-terminator nucleotide comprises the formula

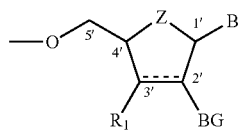

wherein
$R_1$ is H, OH, a hydrophilic group, or a hydrophobic group;
B is at least one homocyclic ring, at least one heterocyclic ring, at least one aryl group, or combinations thereof;
BG is a blocking group;
Z is O or $CH_2$; and ---- represents a single or double bond; and
wherein BG is selected from the group consisting of: CN, $NO_2$, $N_3$, Cl, Br, I, a phosphate group, an aldehyde group, an ester group, an amino group, and combinations thereof.

27. The method of claim 1, wherein the 2'-terminator nucleotide comprises the formula

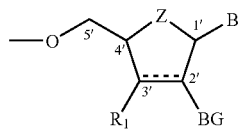

wherein
$R_1$ is H or OH;
B is at least one homocyclic ring, at least one heterocyclic ring, at least one aryl group, or combinations thereof;
BG is a blocking group;
Z is O or $CH_2$; and ---- represents a single or double bond; and wherein BG is selected from the group consisting of: CN, $NO_2$, a phosphate group, an aldehyde group, an amino group, and combinations thereof.

28. The method of claim 1, wherein the 2'-terminator nucleotide comprises the formula

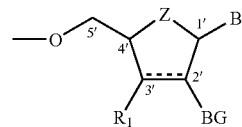

wherein
$R_1$ is OH;
B is at least one homocyclic ring, at least one heterocyclic ring, at least one aryl group, or combinations thereof;
BG is a blocking group;
Z is O or $CH_2$; and ---- represents a single or double bond; and
wherein BG is selected from the group consisting of: CN, $NO_2$, a phosphate group, an aldehyde group, an amino group, and combinations thereof.

29. The method of claim 1, wherein the 2'-terminator nucleotide comprises the formula

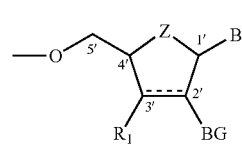

wherein
$R_1$ is H, OH, a hydrophilic group, or a hydrophobic group;
B is at least one homocyclic ring, at least one heterocyclic ring, at least one aryl group, or combinations thereof;
BG is a blocking group;
Z is O or $CH_2$; and ---- represents a single or double bond; and
wherein BG comprises a phosphate group comprising the formula:

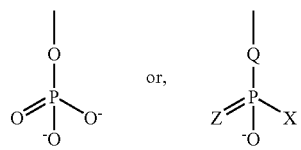

wherein
Q is O, S, or NH;
X is H, OH, $CH_3$, $BH_3$, F, or SeH; and,
Z is O, S, or Se; or,

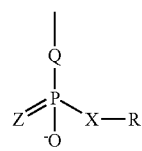

wherein
Q is O, S, or NH;
X is O, S, or NH;

Z is O, S, or Se; and,

R is an alkyl group, an alkenyl group, or an alkynyl group; or,

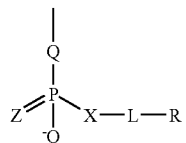

wherein

Q is O, S, or NH;

X is O, S, or NH;

Z is O, S, or Se;

L is —CONH(CH$_2$)$_n$NH—, —CO(CH$_2$)$_n$NH—, or —CONH(CH$_2$CH$_2$O)$_n$CH$_2$CH$_2$NH—;

n is an integer greater than 0; and,

R is NH$_2$, SH, COOH, a quencher moiety, a reporter moiety, biotin, or a affinity moiety.

30. The method of claim 1, wherein the biocatalyst is a DNA polymerase.

31. The method of claim 30, wherein the DNA polymerase has reverse transcriptase activity.

32. The method of claim 10, wherein the additional nucleotide comprises a terminator nucleotide.

* * * * *

SEQUENCE LISTING

<160> NUMBER OF SEQ ID NOS: 22

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgagacacca ggaattagat atcagtacaa tgt                                    33

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ctaaatcaga tcctacatat aagtcatcca tgt                                    33

<210> SEQ ID NO 3
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer
<220> FEATURE:
<221> NAME/KEY: modified_base
<222> LOCATION: (33)
<223> OTHER INFORMATION: 2'-Phosphate-U

<400> SEQUENCE: 3
tgagacacca ggaattagat atcagtacaa tgu                                    33

```
<210> SEQ ID NO 4
<211> LENGTH: 33
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer
<220> FEATURE:
<221> NAME/KEY: modified_base
<222> LOCATION: (33)
<223> OTHER INFORMATION: 2'-Phosphate-U

<400> SEQUENCE: 4
ctaaatcaga tcctacatat aagtcatcca tgu                                    33

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aaacttgtgg tagttggagc tc                                                22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gttggatcat attcgtccac aa                                                22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: 2'-Phosphate-C

<400> SEQUENCE: 7
aaacttgtgg tagttggagc tc                                                22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: 2'-Phosphate-A

<400> SEQUENCE: 8
```

```
gttggatcat attcgtccac aa                                              22

<210> SEQ ID NO 9
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-Phosphate-U

<400> SEQUENCE: 9
aaacttgtgg tagttggagc tgu                                             23

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)
<223> OTHER INFORMATION: 2'-Phosphate-A

<400> SEQUENCE: 10
gttggatcat attcgtccac aa                                              22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)
<223> OTHER INFORMATION: 2'-amino-C

<400> SEQUENCE: 11
cgcctggtct gtacaccgtt ca                                              22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (24)
<223> OTHER INFORMATION: 2'-PO4-A

<400> SEQUENCE: 12
ggaacgaggg tagcaacggc taca                                            24

<210> SEQ ID NO 13
<211> LENGTH: 28
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 13
gcaagcaccc tatcaggcag taccacaa                                              28

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)
<223> OTHER INFORMATION: 2'-Phosphate-A or 2'-monophosphate-3'-
      hydroxyl-A

<400> SEQUENCE: 14
gcaagcaccc tatcaggcag taccacaa                                              28

<210> SEQ ID NO 15
<211> LENGTH: 27
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer
<220> FEATURE:
<221> NAME/KEY: modified_base
<222> LOCATION: (27)
<223> OTHER INFORMATION: 2'-Phosphate-U

<400> SEQUENCE: 15
aataggtgat tttggtctag ctacagu                                               27

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-Phosphate-A

<400> SEQUENCE: 16
ggacccactc catcgagatt tca                                                   23

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (27)
<223> OTHER INFORMATION: 2'-Phosphate-A

<400> SEQUENCE: 17
aataggtgat tttggtctag ctacaga                                               27
```

<210> SEQ ID NO 18
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      primer
<220> FEATURE:
<221> NAME/KEY: modified_base
<222> LOCATION: (23)
<223> OTHER INFORMATION: 2'-Phosphate-U

<400> SEQUENCE: 18
ggacccactc catcgagatt tcu                                           23

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: A(BHQ)

<400> SEQUENCE: 19
gcaagcaccc tatcaggcag taccaca                                       27

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (28)
<223> OTHER INFORMATION: C-3' phosphate

<400> SEQUENCE: 20
ttgtggtact gcctgatagg gtgcttgc                                      28

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)
<223> OTHER INFORMATION: A(BHQ)
<220> FEATURE:
<221> NAME/KEY: modified_base
<222> LOCATION: (27)
<223> OTHER INFORMATION: fluorescein-labeled 2' phosphate-A

<400> SEQUENCE: 21
gcaagcaccc tatcaggcag taccaca                                       27

<210> SEQ ID NO 22
<211> LENGTH: 25
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 22
gcagaaagcg tctagccatg gctta                                              25
```